(12) United States Patent
Cutarelli et al.

(10) Patent No.: US 7,985,860 B2
(45) Date of Patent: Jul. 26, 2011

(54) PROCESS AND INTERMEDIATES FOR THE SYNTHESIS OF 2-(QUINOLIN-5-YL)-4,5 DISUBSTITUTED-AZOLE DERIVATIVES

(75) Inventors: Timothy D. Cutarelli, Basking Ridge, NJ (US); Xiaoyong Fu, Edison, NJ (US); Timothy L. McAllister, Westfield, NJ (US); Michael R. Reeder, Skillman, NJ (US); Jianguo Yin, Plainsboro, NJ (US); Kelvin H. Yong, Lyndhurst, NJ (US); Shuyi Zhang, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 932 days.

(21) Appl. No.: 11/891,348

(22) Filed: Aug. 10, 2007

(65) Prior Publication Data

US 2008/0045718 A1 Feb. 21, 2008

Related U.S. Application Data

(60) Provisional application No. 60/837,567, filed on Aug. 14, 2006, provisional application No. 60/959,252, filed on Jul. 10, 2007.

(51) Int. Cl.
*C07D 215/38* (2006.01)
(52) U.S. Cl. ...................................................... 546/167
(58) Field of Classification Search .................. 546/167
See application file for complete search history.

(56) References Cited

U.S. PATENT DOCUMENTS

| 7,511,062 | B2 * | 3/2009 | Kuang et al. .................. 514/312 |
| 2006/0106062 | A1 | 5/2006 | Kuang et al. |

FOREIGN PATENT DOCUMENTS

WO 2005/116009 * 8/2005

OTHER PUBLICATIONS

International Search Report for PCT/US2007/017796; mailed May 19, 2008.

* cited by examiner

*Primary Examiner* — D. Margaret Seaman
(74) *Attorney, Agent, or Firm* — Patricia A. Shatynski; Valerie J. Camara

(57) ABSTRACT

This application discloses a novel process to synthesize 2-(Quinolin-5yo)-4,5-Disubstituted-Azole derivatives, which may be used, for example, as PDE IV inhibitor compounds in pharmaceutical preparations.

12 Claims, No Drawings

PROCESS AND INTERMEDIATES FOR THE SYNTHESIS OF 2-(QUINOLIN-5-YL)-4,5 DISUBSTITUTED-AZOLE DERIVATIVES

CROSS-REFERENCE TO RELATED APPLICATIONS

The present application claims the priority of each of U.S. Provisional Application Nos. 60/837,567, filed Aug. 14, 2006, and 60/959,252 filed Jul. 10, 2007, each of which is incorporated herein in its entirety by reference.

FIELD OF THE INVENTION

This application discloses a novel process to 2-(Quinolin-5-yl)-4,5 Disubstituted-Azole derivatives, which have utility, for example, as pharmaceutically active compounds, and intermediates useful in the synthesis thereof.

BACKGROUND OF THE INVENTION

As described in Published international application WO 2005/116009 A1 (the '009 publication) and published U.S. patent application no. 2006/0106062 (the '062 publication), each of which was filed on May 16, 2005 (the '009 publication), and each of which is incorporated herein in its entirety by reference, 2-(Quinolin-5-yl)-4,5 Disubstituted-Azole derivatives (Formula I) which have pharmaceutical activity as PDE-4 inhibitor compounds.

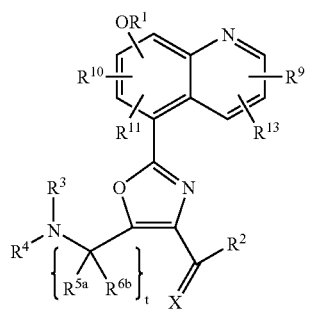

Formula I wherein:
X is O or S
$R^1$ is H, alkyl, cycloalkyl, cycloalkyl($C_1$-$C_4$)alkyl-, —$CH_2F$, —$CHF_2$, —$CF_3$, —C(O)alkyl or —C(O)$NR^{18}R^{19}$;
$R^2$ is —OR* or —N($R^7$)($R^8$), wherein R* is linear, branched, or cyclic alkyl or substituted linear, branched, or cyclic alkyl, and $R^7$ and $R^8$ are defined herein below;
$R^3$ and $R^4$ are independently selected from the group consisting of H, alkyl, hydroxyalkyl and —C(O)Oalkyl;
$R^{5a}$ and $R^{6b}$ are independently selected from the group consisting of H, alkyl, hydroxyalkyl, alkoxyalkyl, mercaptoalkyl, —$CH_2F$, —$CHF_2$, —$CF_3$, —C(O)OH, —C(O)Oalkyl and —C(O)$NR^{43}R^{44}$;
t is 1 or 2;
$R^7$ is H, alkyl, alkenyl, hydroxyalkyl, cycloalkyl, alkoxyalkyl, aminoalkyl, ($R^{17}$-phenyl)alkyl or —$CH_2$—C(O)—O-alkyl;
$R^8$ is H, alkyl, alkenyl, alkoxy, alkoxyalkyl, hydroxyalkyl, dihydroxyalkyl, alkyl-$NR^{18}R^{19}$, cyanoalkyl, $R^{23}$-heteroaryl, $R^{23}$-heteroarylalkyl, ($R^{36}$-heterocycloalkyl)alkyl, $R^{17}$-phenyl, ($R^{17}$-phenyl)alkyl, $R^7$-naphthyl, ($R^{17}$-naphthyl)alkyl, $R^{17}$-benzyloxy, -alkyl-C(O)—$NR^{18}R^{19}$, -alkyl-C(O)—N($R^{30}$)—($R^{23}$-heteroaryl), -alkyl-C(O)—N($R^{30}$)-(cycloalkyl), -alkyl-C(O)—($R^{36}$-heterocycloalkyl); -alkyl-N($R^{30}$)—C(O)Oalkyl, -alkyl-N($R^{30}$)—C(O)—$NR^{18}R^{19}$, -alkyl-N($R^{30}$)—C(O)alkyl, -alkyl-N($R^{30}$)—C(O)-(fluoroalkyl), -alkyl-N($R^{30}$)—C(O)—($R^{39}$-cycloalkyl), -alkyl-N($R^{30}$)—C(O)—($R^{17}$-phenyl), -alkyl-N($R^{30}$)—C(O)—($R^{23}$-heteroaryl), -alkyl-N($R^{30}$)—C(O)-alkylene-($R^{23}$-heteroaryl), -alkyl-NH—$SO_2$—$NR^{18}R^{19}$, -alkyl-N($R^{30}$)—($R^{17}$-phenyl), -alkyl-N($R^{30}$)—($R^{23}$-heteroaryl), -alkyl-O—($R^{17}$-phenyl), -alkyl-O—($R^{23}$-heteroaryl), -alkyl-N($R^{30}$)—$SO_2$-alkyl, $R^{45}$-hydroxyalkyl, dihydroxyalkyl substituted by $R^{17}$-benzyloxy, dihydroxyalkyl substituted by $R^{17}$-phenyl, alkoxyalkyl substituted by $R^{17}$-phenyl, ($R^{17}$-phenyl)alkyl substituted by —$CO_2$alkyl, ($R^{17}$-phenyl)alkyl substituted by —C(O)$NH_2$, alkyl substituted by ($R^{23}$-heteroaryl) and —C(O)$NR^{37}R^{38}$, $R^{12}$-cycloalkyl, ($R^{12}$-cycloalkyl)alkyl,

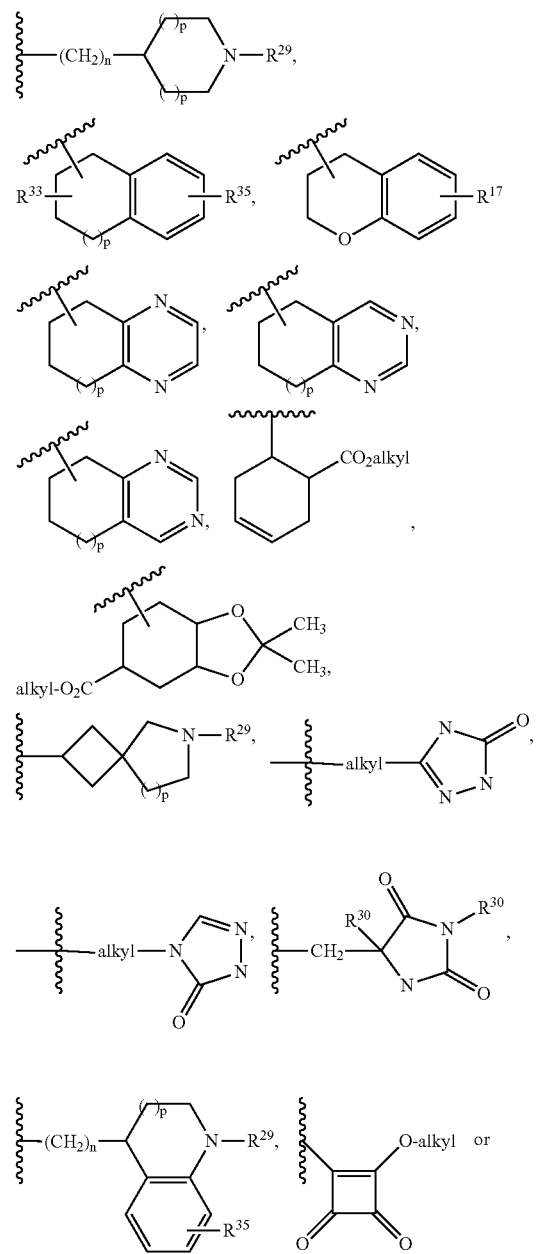

-continued

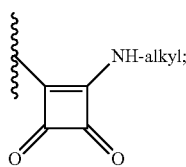

or R⁷ and R⁸ and the nitrogen to which they are attached together form a ring system selected from the group consisting of

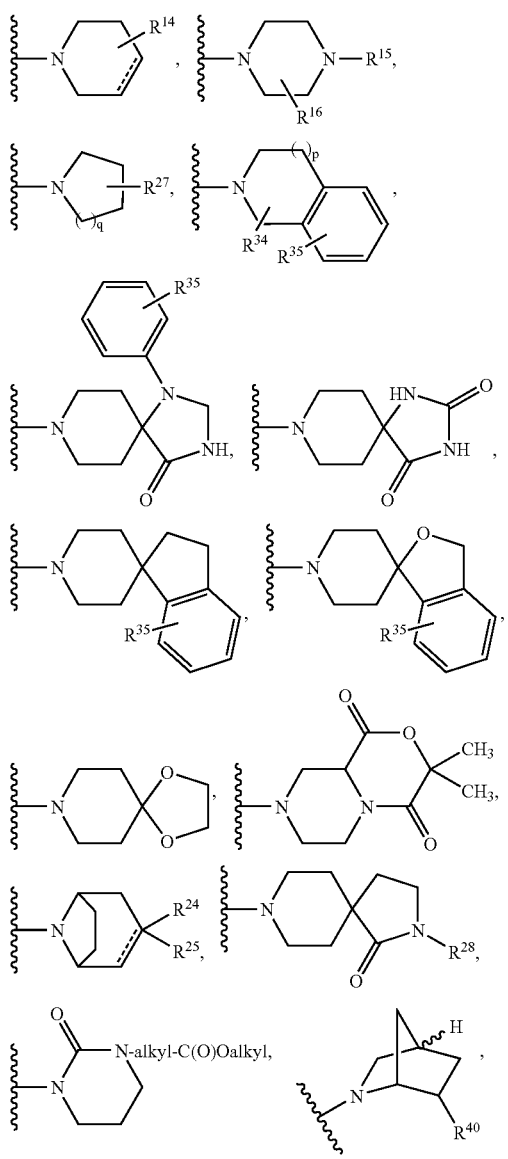

-continued

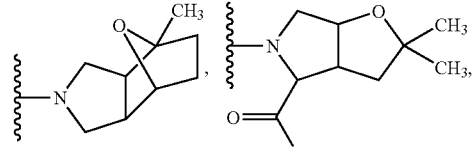

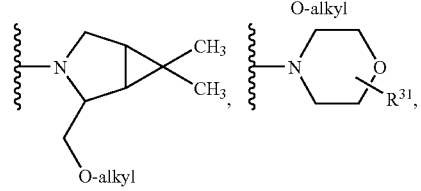

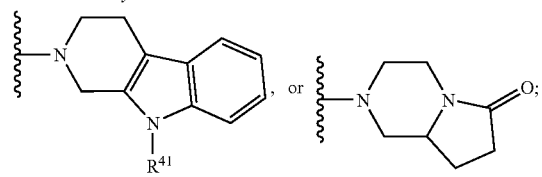

p is 0 or 1;
q is 0 or 1;
the dotted line represents an optional double bond;
$R^9$ is H, halo, alkyl, cycloalkyl, —CH₂F, —CHF₂ or CF₃;
$R^{10}$, $R^{11}$, and $R^{13}$ are independently selected from the group consisting of H and halo;
$R^{12}$ is 1-3 substituents independently selected from the group consisting of H, alkyl, hydroxy, alkoxy, hydroxyalkyl, alkoxyalkyl, —C(O)Oalkyl, —(CH₂)$_n$—N(R³⁰)—C(O)-cycloalkyl, —(CH₂)$_n$—N(R³⁰)—C(O)alkyl, —(CH₂)$_n$—N(R³⁰)—C(O)Oalkyl, —(CH₂)$_n$—N(R³⁰)—(R²³-heteroaryl), —(CH₂)$_n$—N(R³⁰)—C(O)—NR¹⁸R¹⁹ and —(CH₂)$_n$—C(O)—NR¹⁸R¹⁹;
$R^{14}$ is 1 or 2 substituents independently selected from the group consisting of H, OH, halo, alkyl, alkoxy, hydroxyalkyl, alkoxyalkyl, —CF₃, CN, R¹⁷-phenyl, (R¹⁷-phenyl)alkyl, —NR¹⁸R¹⁹, alkyl-NR¹⁸R¹⁹, —(CH₂)$_n$—C(O)OH, —(CH₂)$_n$—C(O)Oalkyl, —(CH₂)$_n$—C(O)alkyl, —(CH₂)$_n$—C(O)(R³⁵-phenyl), —(CH₂)$_n$—C(O)(R²³-heteroaryl), —(CH₂)$_n$—C(O)NR¹⁸R¹⁹, —(CH₂)$_n$—C(O)N(R³⁰)—(CH₂)—(R²³-heteroaryl), —(CH₂)$_n$—N(R³⁰)—C(O)alkyl, —(CH₂)$_n$—N(R³⁰)—C(O)-(fluoroalkyl), —(CH₂)$_n$—N(R³⁰)—C(O)-(cycloalkyl), —(CH₂)$_n$—N(R³⁰)—C(O)(R³⁵-phenyl), —(CH₂)$_n$—N(R³⁰)—C(O)(R²³-heteroaryl), —(CH₂)$_n$—N(R³⁰)C(O)NR¹⁸R¹⁹, —(CH₂)$_n$—N(R³⁰)—C(O)Oalkyl, —(CH₂)$_n$—N(R³⁰)cycloalkyl, —(CH₂)$_n$—N(R³⁰)(R¹⁷-phenyl), —(CH₂)$_n$—N(R³⁰)(R²³-heteroaryl), —(CH₂)$_n$—N(R¹⁸)SO₂alkyl, —(CH₂)$_n$—N(R²⁰)SO₂—(R¹⁷-phenyl), —(CH₂)$_n$—N(R³⁰)SO₂—CF₃, —CH₂S(O)₀₋₂(R³⁵-phenyl), —(CH₂)$_n$—OC(O)N(R²³)alkyl, R²³-heteroaryl, (R²³-heteroaryl)alkyl, (R²³-heteroaryl)oxy, (R²³-heteroaryl)amino, —CH(OH)—(R¹⁷-phenyl), —CH(OH)—(R²³-heteroaryl), —C(=NOR³⁰)—(R¹⁷-phenyl), —C(=NOR³⁰)—(R²³-heteroaryl), morpholinyl, thiomorpholinyl,

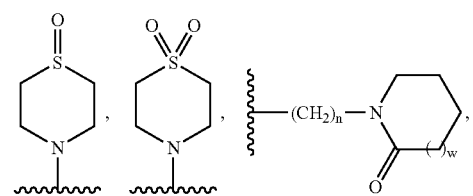

-continued

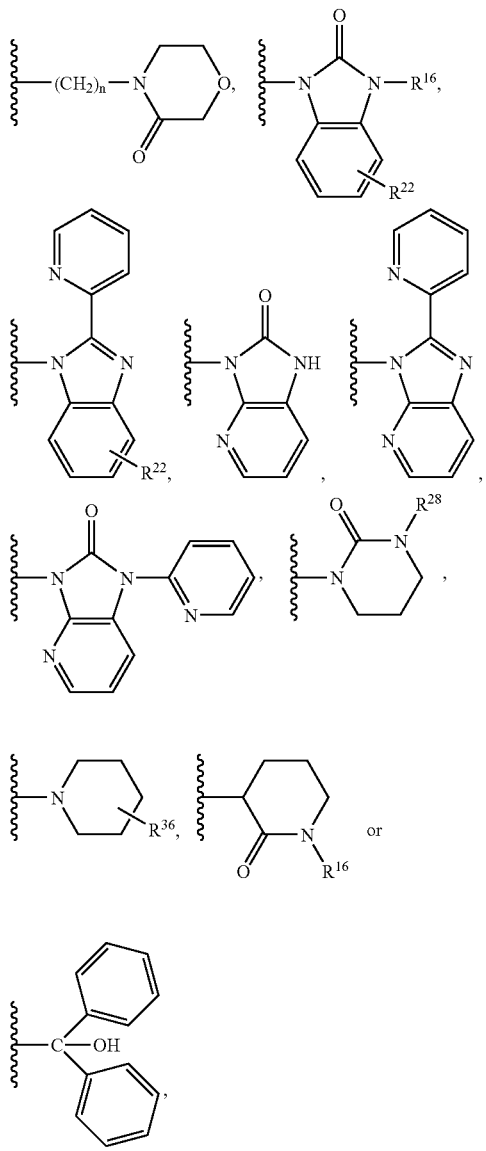

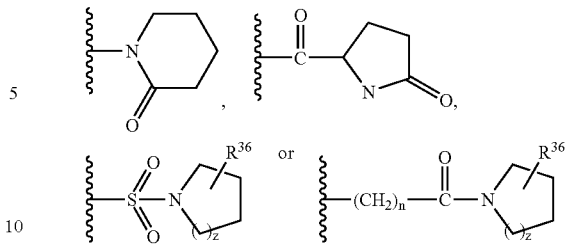

w is 0 or 1;

or two R$^{14}$ substituents and the carbon to which they are both attached form —C(=NOR$^{30}$)— or —C(O)—;

each n is independently 0, 1, 2 or 3;

R$^{15}$ is H, alkyl, cycloalkyl, (cycloalkyl)alkyl, hydroxyalkyl, alkoxyalkyl, —C(O)Oalkyl, —C(O)O(R$^{30}$-cycloalkyl), -alkyl-C(O)O-alkyl, —C(O)O-alkylene-(R$^{35}$-phenyl), R$^{17}$-phenyl, (R$^{17}$-phenyl)alkyl, —CH—(R$^{17}$-phenyl)$_2$, R$^{23}$-heteroaryl, —(CH$_2$)$_n$—C(O)NR$^{18}$R$^{19}$, —SO$_2$-alkyl, —SO$_2$-cycloalkyl, —SO$_2$—CF$_3$, —SO$_2$—(R$^{35}$-phenyl), —SO$_2$—NR$^{18}$R$^{19}$, —C(O)alkyl, —C(O)-(fluoroalkyl), —C(O)—C(CH$_3$)(CF$_3$)$_2$, —C(O)—(R$^{17}$-phenyl), —C(O)—(R$^{23}$-heteroaryl), —C(O)-hydroxyalkyl, —C(O)-alkoxyalkyl, —C(O)—(R$^{39}$-cycloalkyl), —C(O)-alkylene-(R$^{17}$-phenyl), —C(O)-alkylene-(R$^{23}$-heteroaryl), —C(O)-alkylene-S—C(O)alkyl, —C(=S)—(R$^{17}$-phenyl), hydroxyalkyl substituted by R$^{17}$-phenyl, hydroxyalkyl substituted by R$^{23}$-heteroaryl, alkoxyalkyl substituted by R$^{17}$-phenyl, alkoxyalkyl substituted by R$^{23}$-heteroaryl, wherein z is 0, 1 or 2;

R$^{16}$ is 1 to 4 substituents independently selected from the group consisting of H, alkyl, R$^{17}$-phenyl, (R$^{17}$-phenyl)alkyl, (R$^{23}$-heteroaryl)alkyl, hydroxyalkyl, alkoxyalkyl and —C(O)Oalkyl, or two R$^{16}$ groups and the carbon to which they are both attached form —C(O)—;

R$^{17}$ represents 1 to 3 substituents replacing a hydrogen on a phenyl moiety, each of which is independently selected from the group consisting of halo, alkyl, cycloalkyl, —OH, hydroxyalkyl, alkoxy, —CN, —CF$_3$, —OCF$_3$, —OCHF$_2$, —OCH$_2$F, —C(O)OH, —C(O)Oalkyl, —C(O)O—(R$^{35}$-phenyl), —C(O)alkyl, —C(O)—(R$^{35}$-phenyl), —SOalkyl, —SO$_2$alkyl, —SO$_2$—CF$_3$, alkylthio, —NR$^{43}$R$^{44}$, -alkyl-NR$^{43}$R$^{44}$ and heteroaryl; or two R$^{17}$ substituents on adjacent carbon atoms together form —O—CH$_2$—O—, —O—(CH$_2$)$_2$—O—, —(CH$_2$)$_2$—O— or —O—CH$_2$—O—CH$_2$—;

R$^{18}$ and R$^{19}$ are independently selected from the group consisting of H, alkyl, hydroxyalkyl, alkoxyalkyl, R$^{17}$-phenyl and (R$^{17}$-phenyl)alkyl;

R$^{20}$ is H, alkyl, or cycloalkyl;

R$^{22}$ is 1 to 4 substituents independently selected from the group consisting of H, alkyl, hydroxy, alkoxy, halo, —CF$_3$, —NH$_2$ and R$^{35}$-phenyl;

R$^{23}$ is 1 to 4 substituents independently selected from the group consisting of H, alkyl, hydroxy, alkoxy, halo, —CF$_3$, —NR$^{18}$R$^{19}$, —CN, —C(O)Oalkyl, —NHSO$_2$-alkyl and R$^{35}$-phenyl;

R$^{24}$ is H, OH or alkoxy; or when the optional double bond is present, R$^{24}$ and the adjacent carbon atom form the double bond;

R$^{25}$ is H or R$^{35}$ phenyl;

R$^{27}$ is 1 to 3 substituents independently selected from the group consisting of H, halo, OH, alkyl, alkoxy, hydroxyalkyl, alkoxyalkyl, —CF$_3$, —CN, —C(O)OH, —C(O)Oalkyl, —C(O)N(R$^{30}$)(R$^{18}$), —C(O)—(R$^{36}$-heterocycloalkyl), R$^{17}$-phenyl, (R$^{17}$-phenyl)-alkyl, R$^{23}$-heteroaryl, (R$^{23}$-heteroaryl)alkyl, (R$^{23}$-heteroaryl)oxy, (R$^{23}$-heteroaryl)amino NR$^{18}$R$^{19}$, NR$^{18}$R$^{19}$-alkyl, —(CH$_2$)$_n$—N(R$^{30}$)—C(O)alkyl, —(CH$_2$)$_n$—N(R$^{30}$)—C(O)-(fluoroalkyl), —(CH$_2$)$_n$—N(R$^{30}$)—C(O)alkoxyalkyl, —(CH$_2$)$_n$—N(R$^{30}$)—C(O)(cycloalkyl), —(CH$_2$)$_n$—N(R$^{30}$)—(R$^{23}$-heteroaryl), —(CH$_2$)$_n$—N(R$^{30}$)—C(O)—(R$^{23}$-heteroaryl), —(CH$_2$)$_n$—N(R$^{30}$)—C(O)O-alkyl, —(CH$_2$)$_n$—N(R$^{30}$)—C(O)O—(CF$_3$-alkyl), —(CH$_2$)$_n$—N(R$^{30}$)—C(O)O—(R$^{39}$-cycloalkyl), —(CH$_2$)$_n$—N(R$^{30}$)—C(O)O-alkylene-cycloalkyl, —(CH$_2$)$_n$—N(R$^{30}$)—C(O)—N(R$^{30}$)(R$^{20}$), —(CH$_2$)$_n$—N(R$^{30}$)—SO$_2$-alkyl, —(CH$_2$)$_n$—N(R$^{30}$)—SO$_2$—CF$_3$, —(CH$_2$)$_n$—N(R$^{30}$)—SO$_2$—N(R$^{30}$)$_2$ and

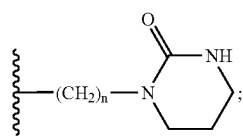

or two $R^{27}$ groups and the carbon to which they are both attached form —C(=NOR$^{30}$)— or —C(O)—;

$R^{28}$ is H, alkyl, $R^{35}$-benzyl or -alkyl-C(O)O-alkyl;

$R^{29}$ is alkyl, —C(O)Oalkyl, —C(O)alkyl, —C(O)cycloalkyl, —C(O)—(R$^{17}$-phenyl), —C(O)—(R$^{23}$-heteroaryl), —SO$_2$-alkyl, —SO$_2$—(R$^{35}$-phenyl), —C(O)NR$^{18}$R$^{19}$, R$^{35}$-phenyl, (R$^{35}$-phenyl)alkyl or R$^{23}$-heteroaryl;

$R^{30}$ is independently selected from the group consisting of H, alkyl and $R^{35}$-benzyl;

$R^{31}$ is H, alkyl, $R^{35}$-benzyl or phenoxyalkyl;

$R^{33}$ is H, OH or alkoxy;

$R^{34}$ is H, alkyl, hydroxyalkyl, alkoxyalkyl or —C(O)Oalkyl;

$R^{35}$ is 1 to 3 substituents independently selected from the group consisting of H, halo, alkyl, OH, —CF$_3$ and alkoxy;

$R^{36}$ is 1 or 2 substituents independently selected from the group consisting of H, alkyl, R$^{17}$-phenyl, alkoxyalkyl and —C(O)Oalkyl; or two $R^{36}$ groups and the carbon to which they are both attached form —C(=NOR$^{30}$)— or —C(O)—;

$R^{37}$ and $R^{38}$ are independently selected from the group consisting of H and alkyl, or $R^{37}$ and $R^{38}$ together are —(CH$_2$)$_3$— or —(CH$_2$)$_4$—, and together with the nitrogen to which they are attached, form a ring;

$R^{39}$ is H, OH, alkyl, alkoxy, or CF$_3$;

$R^{40}$ is —OR$^{30}$ or —NHC(O)alkyl;

$R^{41}$ is H or —SO$_2$alkyl;

$R^{42}$ is —(CH$_2$)$_n$—(R$^{35}$-phenyl), —(CH$_2$)$_n$—(R$^{23}$-heteroaryl), —C(O)Oalkyl or —C(O)alkyl;

$R^{43}$ and $R^{44}$ are independently selected from the group consisting of H and alkyl; and $R^{45}$ is 1 or 2 substituents independently selected from the group consisting of halo, alkoxyalkyl, —CO$_2$alkyl, R$^{17}$-phenyl, R$^{23}$-heteroaryl and cycloalkyl.

Compounds of Formula I can be prepared using synthesis procedures and synthetic schemes described in the above-referenced published applications, for example, on pages 25 to 32 of the '009 publication, and exemplified throughout the '062 and '009 publications. One example is the synthetic scheme shown on pages 26 to 28 of the '009 publication, summarized below as Scheme I.

Scheme I

Step 1

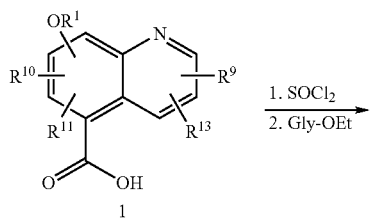

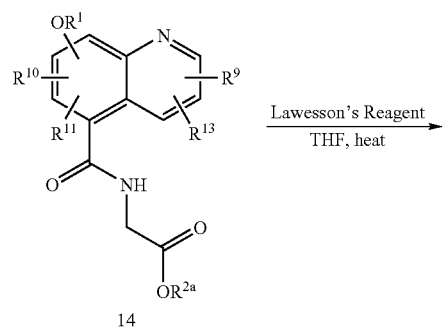

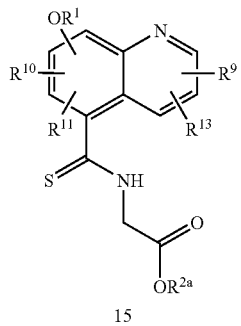

Step 2

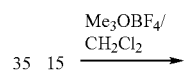

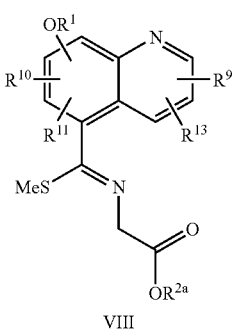

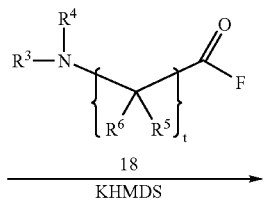

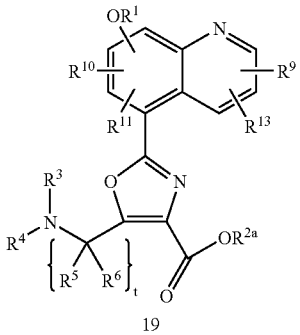

Step 3

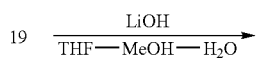

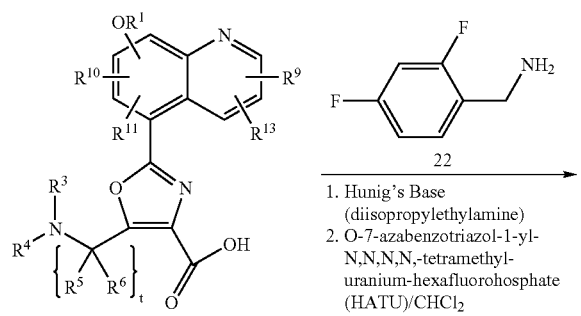

Compounds of Formula I of particular interest include the compounds having the structure of Formulae IXaa and IXab (below), Formula IXaa

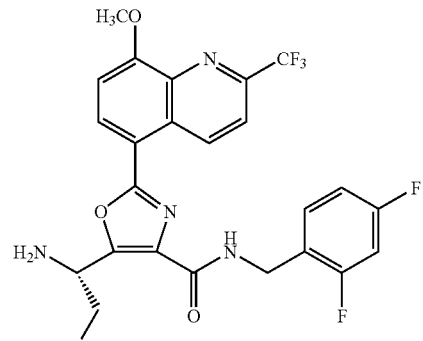

Formula IXab

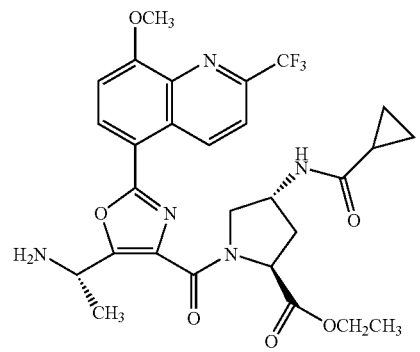

Processes for preparing these compounds are described in, for example, published US patent application No. 2006/0106062 A1, published May 18, 2006 (the above-described '062 publication). In particular, the '062 publication describes a batch process for the preparation of the compound of Formula IXaa on pages 83 to 86 (preparative Examples 5 to 7, in preparation of the example compound 26-347, which is illustrated on page 193) and a process for the preparation of the compound of Formula IXab on pages 380 to 382 (preparative Examples 8 to 11 in preparation of the example compound 38-8, which is illustrated on page 383), each of which process is incorporated by reference herein in its entirety, and each of which is next described in further detail.

In addition, the compound of Formula IXab has been prepared in accordance with Scheme Ia.

Scheme Ia

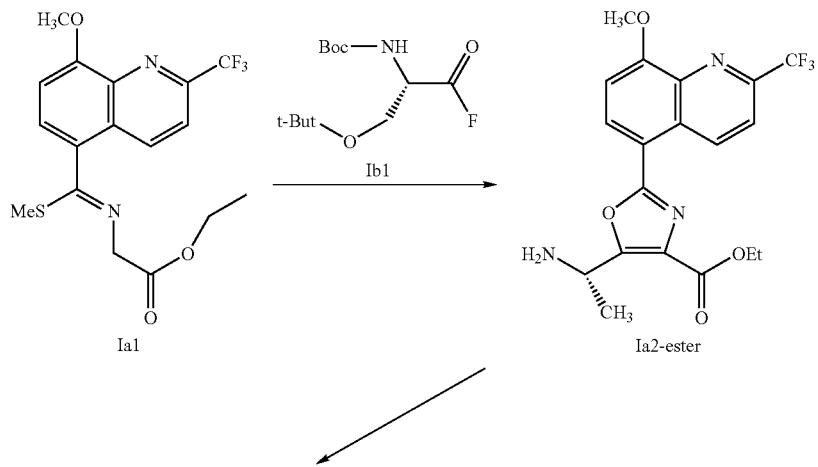

Ia2-acid →

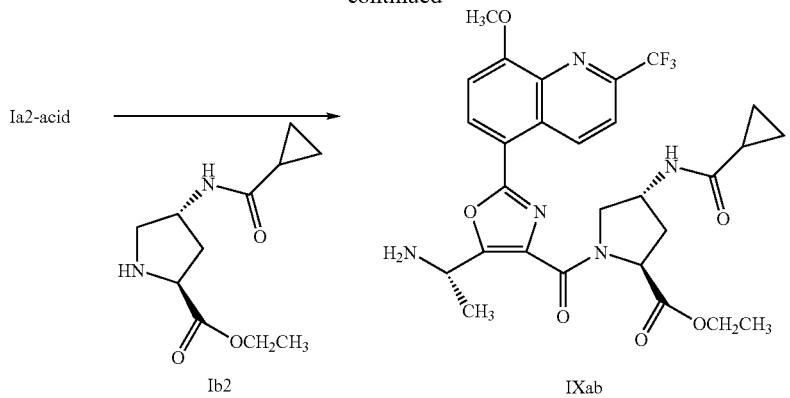

Ib2    IXab

With reference to Scheme Ia, preparation of the tri substituted oxazole of Formula Ia2-ester, by treatment of the compound of Formula Ia1 with the acid halide of Formula Ib1, or its related acid (Ia2-acid) prepared by hydrolyzing the ester functional group of the oxazole of Formula Ia2-ester, provides a product which contains high levels of unwanted side reaction products and shows poor utilization of the starting materials.

In the same manner, the compound of Formula IXaa can be prepared in accordance with Scheme Iaa, as described in the above-reference '009 publication beginning on page 145, Example 8 therein, and with reference to synthesis schemes on pages 26 and 27 therein.

Scheme Iaa

Step 1

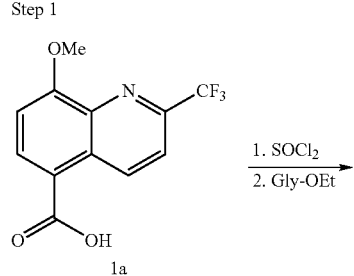

1a

1. SOCl$_2$
2. Gly-OEt

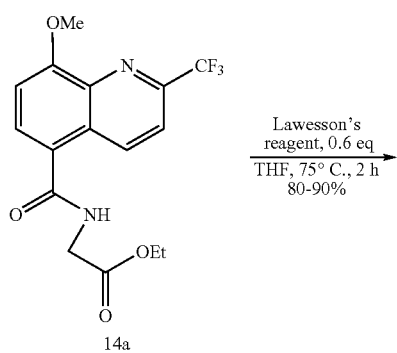

14a

Lawesson's reagent, 0.6 eq
THF, 75° C., 2 h
80-90%

-continued

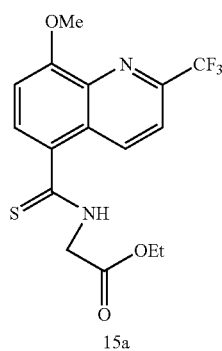

15a

Step 2

15a
Me$_3$OBF$_4$,
CH$_2$Cl$_2$
0°-r.t., 2 h
>90 %

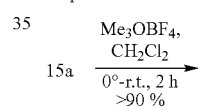

VIIIa

18a
KHMDS, 2.1 eq.
THF, -78° C.-r.t.
1 h, 55%

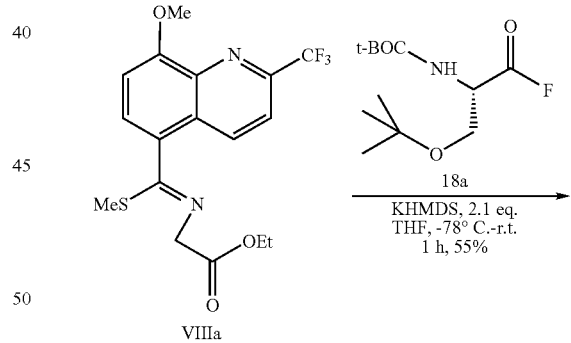

19a

13

-continued

Step 3

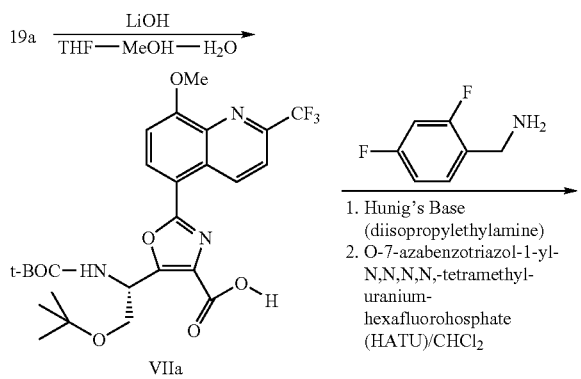

VIIa

1. Hunig's Base (diisopropylethylamine)
2. O-7-azabenzotriazol-1-yl-N,N,N,N,-tetramethyl-uranium-hexafluorophosphate (HATU)/CHCl₂

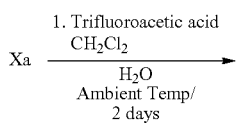

Xa

Step 4

Xa  1. Trifluoroacetic acid CH₂Cl₂ / H₂O Ambient Temp/ 2 days →

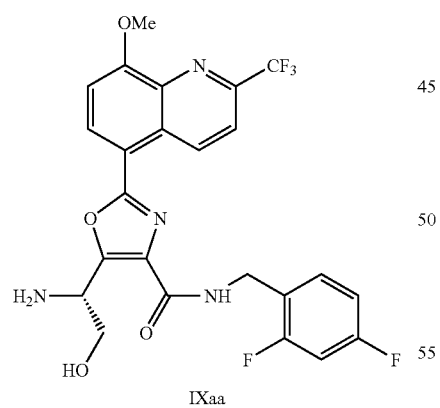

IXaa

As will be appreciated from the foregoing, a key step in the synthesis of PDE IV compounds of Formula I is illustrated in Scheme Ib (below), and shown in Step 2 in any of Synthesis Schemes I, Ia, and Iaa, which is the formation of an oxazole ring by acylating a quinolinyl intermediate compound, with reference to Scheme Ib, compound 10, using an acid fluoride acylating reagent (11) to provide the oxazoline-substituted quinoline compound (IV).

14

Scheme Ib

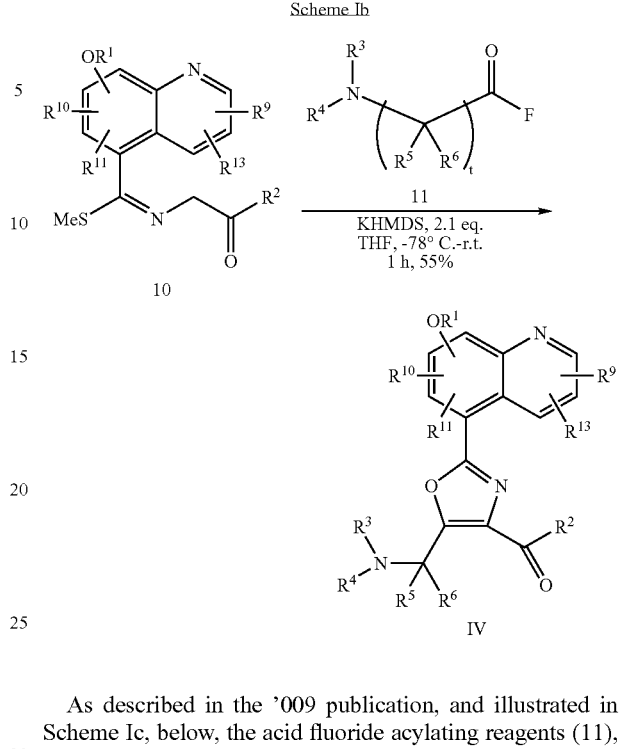

As described in the '009 publication, and illustrated in Scheme Ic, below, the acid fluoride acylating reagents (11), for example, with reference to Scheme Iaa, step 2, the compound of Formula 18a, wherein $R^3$ and $R^5$ are hydrogen, $R^4$ is t-BOC, and $R^6$ is t-butoxymethyl-, that are necessary to prepare these critical intermediates in accordance with these schemes are themselves prepared by treating the corresponding acid with toxic, unstable cyuranic fluoride (9), as illustrated in Scheme Ic.

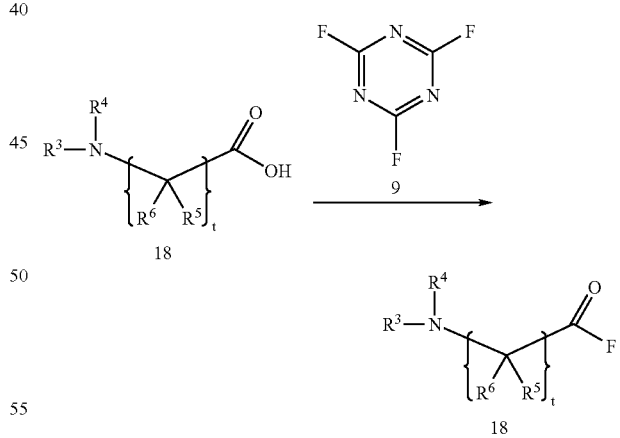

As will be appreciated, when the acylating reagent is to be provided from an acid which contains functional groups that may be sensitive to unwanted side reactions under the conditions used to prepare the acylating reagent or under the acylation conditions, the sensitive functionality is converted to a protecting group before the fluorination and/or subsequent acylation reactions are carried out. This method requires handling of a hazardous and toxic reagent, the cyuranic fluoride. In addition to being a hazardous material, cyuranic fluoride is not available in lot quantities of a size suitable for commercial scale preparation of the acid fluoride intermediate.

OBJECTIVES AND SUMMARY OF THE INVENTION

In view of the foregoing, what is needed is a synthetic scheme useful for preparing the PDE IV inhibitor compounds which utilizes safer materials and provides a synthesis scheme affording practical scale up to a batch size suitable for commercial scale preparation. These and other objectives and/or advantages are provided by the present invention.

On aspect of the present invention is a novel process for preparing intermediates useful in the provision 2-(Quinolin-5-yl)-4,5 Disubstituted-Azole derivative intermediate compounds useful in the preparation of the compounds of Formula I which have pharmaceutical activity as PDE-4 inhibitor compounds:

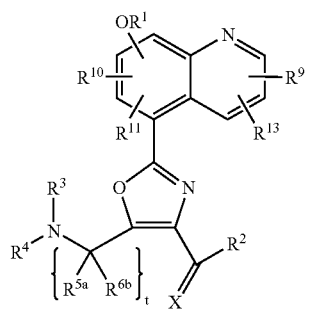

Formula I wherein:

t is 1 or 2;

X is O or S $R^1$ is H, alkyl, cycloalkyl, cycloalkyl($C_1$-$C_4$)alkyl-, —$CH_2F$, —$CHF_2$, —$CF_3$, —C(O)alkyl or —C(O)$NR^{18}R^{19}$;

$R^2$ is —$OR^{2a}$ or —N($R^7$)($R^8$), wherein $R^{2a}$ is linear, branched, or cyclic alkyl or substituted linear, branched, or cyclic alkyl, and $R^7$ and $R^8$ are defined herein below;

$R^3$ and $R^4$ are independently selected from the group consisting of H, alkyl, hydroxyalkyl and —C(O)Oalkyl;

$R^{5a}$ and $R^{6b}$ are independently selected from the group consisting of H, alkyl, hydroxyalkyl, alkoxyalkyl, mercaptoalkyl, —$CH_2F$, —$CHF_2$, —$CF_3$, —C(O)OH, —C(O)Oalkyl and —C(O)$NR^{43}R^{44}$;

$R^7$ is H, alkyl, alkenyl, hydroxyalkyl, cycloalkyl, alkoxyalkyl, aminoalkyl, ($R^{17}$-phenyl)alkyl or —$CH_2$—C(O)—O-alkyl;

$R^8$ is H, alkyl, alkenyl, alkoxy, alkoxyalkyl, hydroxyalkyl, dihydroxyalkyl, alkyl-$NR^{18}R^{19}$, cyanoalkyl, $R^{23}$-heteroaryl, $R^{23}$-heteroarylalkyl, ($R^{36}$-heterocycloalkyl)alkyl, $R^{17}$-phenyl, ($R^{17}$-phenyl)alkyl, $R^{17}$-naphthyl, ($R^{17}$-naphthyl)alkyl, $R^{17}$-benzyloxy, -alkyl-C(O)—$NR^{18}R^{19}$, -alkyl-C(O)—N($R^{30}$)—($R^{23}$-heteroaryl), -alkyl-C(O)—N($R^{30}$)-(cycloalkyl), -alkyl-C(O)—($R^{36}$-heterocycloalkyl); -alkyl-N($R^{30}$)—C(O)Oalkyl, -alkyl-N($R^{30}$)—C(O)—$NR^{18}R^{19}$, -alkyl-N($R^{30}$)—C(O)alkyl, -alkyl-N($R^{30}$)—C(O)-(fluoroalkyl), -alkyl-N($R^{30}$)—C(O)—($R^{39}$-cycloalkyl), -alkyl-N($R^{30}$)—C(O)—($R^{17}$-phenyl), -alkyl-N($R^{30}$)—C(O)—($R^{23}$-heteroaryl), -alkyl-N($R^{30}$)—C(O)-alkylene-($R^{23}$-heteroaryl), -alkyl-NH—$SO_2$—$NR^{18}R^{19}$, -alkyl-N($R^{30}$)—($R^{17}$-phenyl), -alkyl-N($R^{30}$)—($R^{23}$-heteroaryl), -alkyl-O—($R^{17}$-phenyl), -alkyl-O—($R^{23}$-heteroaryl), -alkyl-N($R^{30}$)—$SO_2$-alkyl, $R^{45}$-hydroxyalkyl, dihydroxyalkyl substituted by $R^{17}$-benzyloxy, dihydroxyalkyl substituted by $R^{17}$-phenyl, alkoxyalkyl substituted by $R^{17}$-phenyl, ($R^{17}$-phenyl)alkyl substituted by —$CO_2$alkyl, ($R^{17}$-phenyl)alkyl substituted by —C(O)$NH_2$, alkyl substituted by ($R^{23}$-heteroaryl) and —C(O)$NR^{37}R^{38}$, $R^{12}$-cycloalkyl, ($R^{12}$-cycloalkyl)alkyl,

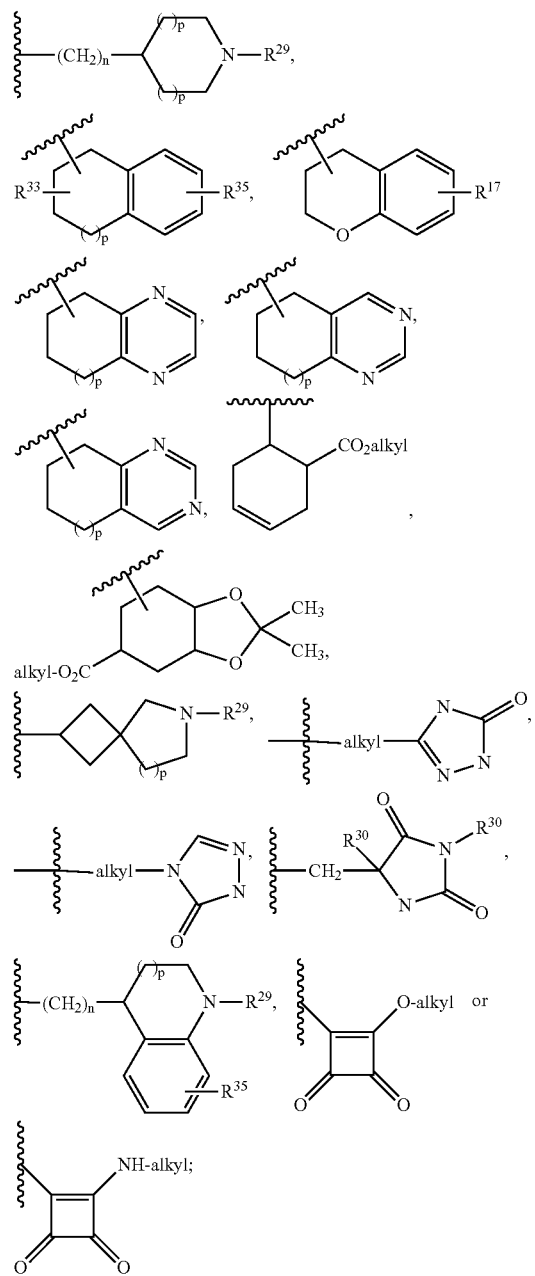

or $R^7$ and $R^8$ and the nitrogen to which they are attached together form a ring system selected from the group consisting of

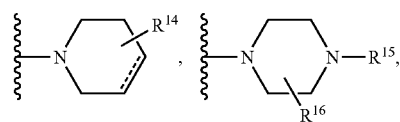

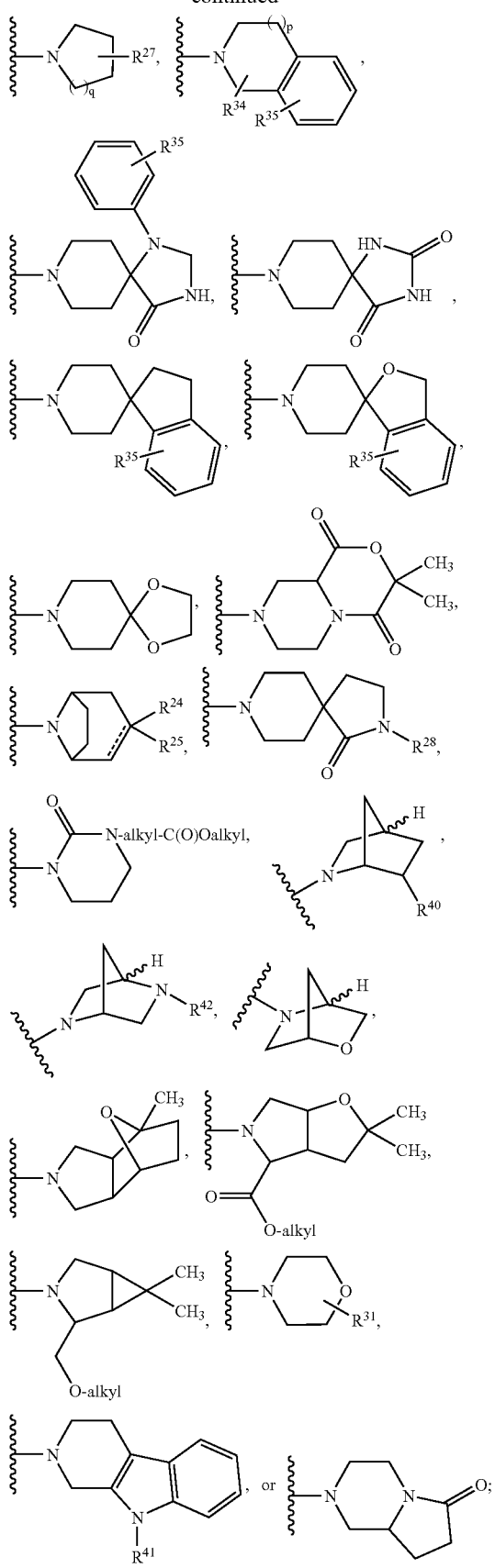

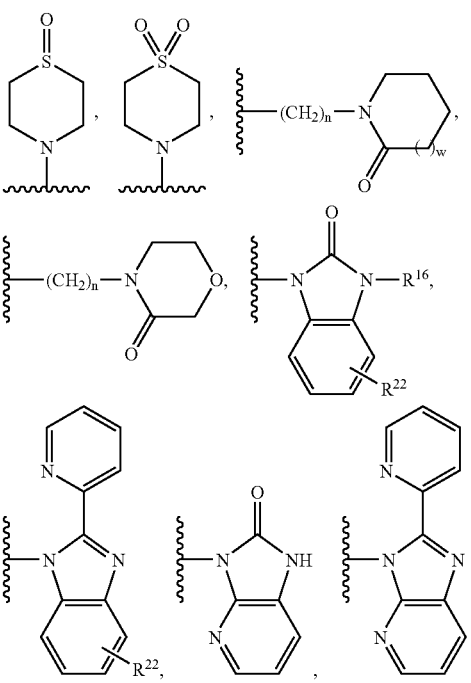

p is 0 or 1;

q is 0 or 1;

the dotted line represents an optional double bond;

$R^9$ is H, halo, alkyl, cycloalkyl, —$CH_2F$, —$CHF_2$ or $CF_3$;

$R^{10}$, $R^{11}$, and $R^{13}$ are independently selected from the group consisting of H and halo;

$R^{12}$ is 1-3 substituents independently selected from the group consisting of H, alkyl, hydroxy, alkoxy, hydroxyalkyl, alkoxyalkyl, —C(O)Oalkyl, —$(CH_2)_n$—N($R^{30}$)—C(O)-cycloalkyl, —$(CH_2)_n$—N($R^{30}$)—C(O)alkyl, —$(CH_2)_n$—N($R^{30}$)—C(O)Oalkyl, —$(CH_2)_n$—N($R^{30}$)—($R^{23}$-heteroaryl), —$(CH_2)_n$—N($R^{30}$)—C(O)—$NR^{18}R^{19}$ and —$(CH_2)_n$—C(O)—$NR^{18}R^{19}$;

$R^{14}$ is 1 or 2 substituents independently selected from the group consisting of H, OH, halo, alkyl, alkoxy, hydroxyalkyl, alkoxyalkyl, —$CF_3$, CN, $R^{17}$-phenyl, ($R^{17}$-phenyl)alkyl, —$NR^{18}R^{19}$, alkyl-$NR^{18}R^{19}$, —$(CH_2)_n$—C(O)OH, —$(CH_2)_n$—C(O)Oalkyl, —$(CH_2)_n$—C(O)alkyl, —$(CH_2)_n$—C(O)($R^{35}$-phenyl), —$(CH_2)_n$—C(O)($R^{23}$-heteroaryl), —$(CH_2)_n$—C(O)$NR^{18}R^{19}$, —$(CH_2)_n$—C(O)N($R^{30}$)—$(CH_2)_n$—($R^{23}$-heteroaryl), —$(CH_2)_n$—N($R^{30}$)—C(O)alkyl, —$(CH_2)_n$—N($R^{30}$)—C(O)-(fluoroalkyl), —$(CH_2)_n$—N($R^{30}$)—C(O)-(cycloalkyl), —$(CH_2)_n$—N($R^{30}$)—C(O)($R^{35}$-phenyl), —$(CH_2)_n$—N($R^{30}$)—C(O)($R^{23}$-heteroaryl), —$(CH_2)_n$—N($R^{30}$)C(O)$NR^{18}R^{19}$, —$(CH_2)_n$—N($R^{30}$)—C(O)Oalkyl, —$(CH_2)_n$—N($R^{30}$)cycloalkyl, —$(CH_2)_n$—N($R^{30}$)($R^{17}$-phenyl), —$(CH_2)_n$—N($R^{30}$)($R^{23}$-heteroaryl), —$(CH_2)_n$—N($R^{18}$)$SO_2$alkyl, —$(CH_2)_n$—N($R^{23}$)$SO_2$—($R^{17}$-phenyl), —$(CH_2)_n$—N($R^{30}$)$SO_2$—$CF_3$, —$CH_2S(O)_{0-2}$($R^{35}$-phenyl), —$(CH_2)_n$—OC(O)N($R^{23}$)alkyl, $R^{23}$-heteroaryl, ($R^{23}$-heteroaryl)alkyl, ($R^{23}$-heteroaryl)oxy, ($R^{23}$-heteroaryl)amino, —CH(OH)—($R^{17}$-phenyl), —CH(OH)—($R^{23}$-heteroaryl), —C(=$NOR^{30}$)—($R^{17}$-phenyl), —C(=$NOR^{30}$)—($R^{23}$-heteroaryl), morpholinyl, thiomorpholinyl,

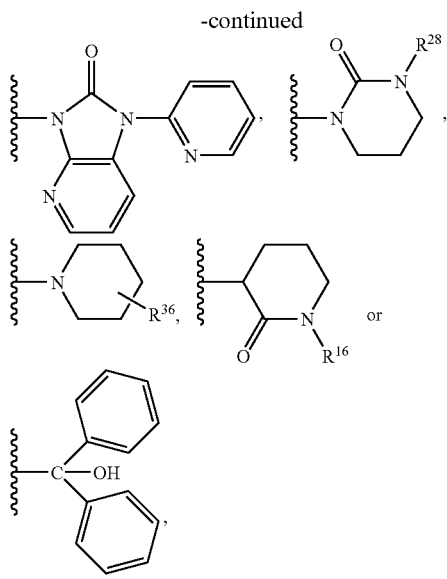

w is 0 or 1;

or two $R^{14}$ substituents and the carbon to which they are both attached form —C(=NOR$^{30}$)— or —C(O)—;

each n is independently 0, 1, 2 or 3;

$R^{15}$ is H, alkyl, cycloalkyl, (cycloalkyl)alkyl, hydroxyalkyl, alkoxyalkyl, —C(O)Oalkyl, —C(O)O(R$^{30}$-cycloalkyl), -alkyl-C(O)O-alkyl, —C(O)O-alkylene-(R$^{35}$-phenyl), R$^{17}$-phenyl, (R$^{17}$-phenyl)alkyl, —CH—(R$^{17}$-phenyl)$_2$, R$^{23}$-heteroaryl, —(CH$_2$)$_n$—C(O)NR$^{18}$R$^{19}$, —SO$_2$-alkyl, —SO$_2$-cycloalkyl, —SO$_2$—CF$_3$, —SO$_2$—(R$^{35}$-phenyl), —SO$_2$—NR$^{18}$R$^{19}$, —C(O)alkyl, —C(O)-(fluoroalkyl), —C(O)—C(CH$_3$)(CF$_3$)$_2$, —C(O)—(R$^{17}$-phenyl), —C(O)—(R$^{23}$-heteroaryl), —C(O)-hydroxyalkyl, —C(O)-alkoxyalkyl, —C(O)—(R$^{39}$-cycloalkyl), —C(O)-alkylene-(R$^{17}$-phenyl), —C(O)-alkylene-(R$^{23}$-heteroaryl), —C(O)-alkylene-S—C(O)alkyl, —C(=S)—(R$^{17}$-phenyl), hydroxyalkyl substituted by R$^{17}$-phenyl, hydroxyalkyl substituted by R$^{23}$-heteroaryl, alkoxyalkyl substituted by R$^{17}$-phenyl, alkoxyalkyl substituted by R$^{23}$-heteroaryl,

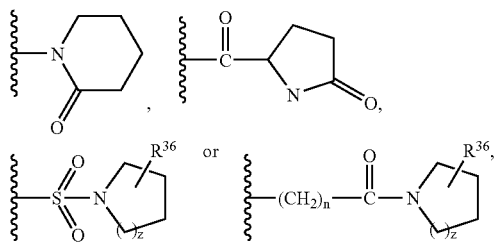

wherein z is 0, 1 or 2;

$R^{16}$ is 1 to 4 substituents independently selected from the group consisting of H, alkyl, R$^{17}$-phenyl, (R$^{17}$-phenyl)alkyl, (R$^{23}$-heteroaryl)alkyl, hydroxyalkyl, alkoxyalkyl and —C(O)Oalkyl, or two R$^{16}$ groups and the carbon to which they are both attached form —C(O)—;

$R^{17}$ represents 1 to 3 substituents replacing a hydrogen on a phenyl moiety, each of which is independently selected from the group consisting of halo, alkyl, cycloalkyl, —OH, hydroxyalkyl, alkoxy, —CN, —CF$_3$, —OCF$_3$, —OCHF$_2$, —OCH$_2$F, —C(O)OH, —C(O)Oalkyl, —C(O)O—(R$^{35}$-phenyl), —C(O)alkyl, —C(O)—(R$^{35}$-phenyl), —SOalkyl, —SO$_2$alkyl, —SO$_2$—CF$_3$, alkylthio, —NR$^{43}$R$^{44}$, -alkyl-NR$^{43}$R$^{44}$ and heteroaryl; or two R$^{17}$ substituents on adjacent carbon atoms together form —O—CH$_2$—O—, —O—(CH$_2$)$_2$—O—, —(CH$_2$)$_2$—O— or —O—CH$_2$—O—CH$_2$—;

$R^{18}$ and $R^{19}$ are independently selected from the group consisting of H, alkyl, hydroxyalkyl, alkoxyalkyl, R$^{17}$-phenyl and (R$^{17}$-phenyl)alkyl;

$R^{20}$ is H, alkyl, or cycloalkyl;

$R^{22}$ is 1 to 4 substituents independently selected from the group consisting of H, alkyl, hydroxy, alkoxy, halo, —CF$_3$, —NH$_2$ and R$^{35}$-phenyl;

$R^{23}$ is 1 to 4 substituents independently selected from the group consisting of H, alkyl, hydroxy, alkoxy, halo, —CF$_3$, —NR$^{18}$R$^{19}$, —CN, —C(O)Oalkyl, —NHSO$_2$-alkyl and R$^{35}$-phenyl;

$R^{24}$ is H, OH or alkoxy; or when the optional double bond is present, R$^{24}$ and the adjacent carbon atom form the double bond;

$R^{25}$ is H or R$^{35}$-phenyl;

$R^{27}$ is 1 to 3 substituents independently selected from the group consisting of H, halo, OH, alkyl, alkoxy, hydroxyalkyl, alkoxyalkyl, —CF$_3$, —CN, —C(O)OH, —C(O)Oalkyl, —C(O)N(R$^{30}$)(R$^{18}$), —C(O)—(R$^{36}$-heterocycloalkyl), R$^{17}$-phenyl, (R$^{17}$-phenyl)-alkyl, R$^{23}$-heteroaryl, (R$^{23}$-heteroaryl)alkyl, (R$^{23}$-heteroaryl)oxy, (R$^{23}$-heteroaryl)amino NR$^{18}$R$^{19}$, NR$^{18}$R$^{19}$-alkyl, —(CH$_2$)$_n$—N(R$^{30}$)—C(O)alkyl, —(CH$_2$)$_n$—N(R$^{30}$)—C(O)-(fluoroalkyl), —(CH$_2$)$_n$—N(R$^{30}$)—C(O)alkoxyalkyl, —(CH$_2$)$_n$—N(R$^{30}$)—C(O)(cycloalkyl), —(CH$_2$)$_n$—N(R$^{30}$)—(R$^{23}$-heteroaryl), —(CH$_2$)$_n$—N(R$^{30}$)—C(O)—(R$^{23}$-heteroaryl), —(CH$_2$)$_n$—N(R$^{30}$)—C(O)O-alkyl, —(CH$_2$)$_n$—N(R$^{30}$)—C(O)O—(CF$_3$-alkyl), —(CH$_2$)$_n$—N(R$^{30}$)—C(O)O—(R$^{39}$-cycloalkyl), —(CH$_2$)$_n$—N(R$^{30}$)—C(O)O-alkylene-cycloalkyl, —(CH$_2$)$_n$—N(R$^{30}$)—C(O)—N(R$^{30}$)(R$^{20}$), —(CH$_2$)$_n$—N(R$^{30}$)—SO$_2$-alkyl, —(CH$_2$)$_n$—N(R$^{30}$)—SO$_2$—CF$_3$, —(CH$_2$)$_n$—N(R$^{30}$)—SO$_2$—N(R$^{30}$)$_2$ and

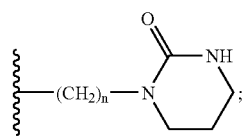

or two $R^{27}$ groups and the carbon to which they are both attached form —C(=NOR$^{30}$)— or —C(O)—;

$R^{28}$ is H, alkyl, R$^{35}$-benzyl or -alkyl-C(O)O-alkyl;

$R^{29}$ is alkyl, —C(O)Oalkyl, —C(O)alkyl, —C(O)cycloalkyl, —C(O)—(R$^{17}$-phenyl), —C(O)—(R$^{23}$-heteroaryl), —SO$_2$-alkyl, —SO$_2$—(R$^{35}$-phenyl), —C(O)NR$^{18}$R$^{19}$, R$^{35}$-phenyl, (R$^{35}$-phenyl)alkyl or R$^{23}$-heteroaryl;

$R^{30}$ is independently selected from the group consisting of H, alkyl and R$^{35}$-benzyl;

$R^{31}$ is H, alkyl, R$^{35}$-benzyl or phenoxyalkyl;

$R^{33}$ is H, OH or alkoxy;

$R^{34}$ is H, alkyl, hydroxyalkyl, alkoxyalkyl or —C(O)Oalkyl;

$R^{35}$ is 1 to 3 substituents independently selected from the group consisting of H, halo, alkyl, OH, —CF$_3$ and alkoxy;

$R^{36}$ is 1 or 2 substituents independently selected from the group consisting of H, alkyl, R$^{17}$-phenyl, alkoxyalkyl and —C(O)Oalkyl; or two R$^{36}$ groups and the carbon to which they are both attached form —C(=NOR$^{30}$)— or —C(O)—;

$R^{37}$ and $R^{38}$ are independently selected from the group consisting of H and alkyl, or R$^{37}$ and R$^{38}$ together are —(CH$_2$)$_3$— or —(CH$_2$)$_4$—, and together with the nitrogen to which they are attached, form a ring;

R$^{39}$ is H, OH, alkyl, alkoxy, or CF$_3$;

R$^{40}$ is —OR$^{30}$ or —NHC(O)alkyl;

R$^{41}$ is H or —SO$_2$alkyl;

R$^{42}$ is —(CH$_2$)$_n$—(R$^{35}$-phenyl), —(CH$_2$)$_n$—(R$^{23}$-heteroaryl), —C(O)Oalkyl or —C(O)alkyl;

R$^{43}$ and R$^{44}$ are independently selected from the group consisting of H and alkyl; and R$^{45}$ is 1 or 2 substituents independently selected from the group consisting of halo, alkoxyalkyl, —CO$_2$alkyl, R$^{17}$-phenyl, R$^{23}$-heteroaryl and cycloalkyl, wherein said intermediate from which the compounds of Formula I are prepared comprises the compound of Formula IV,

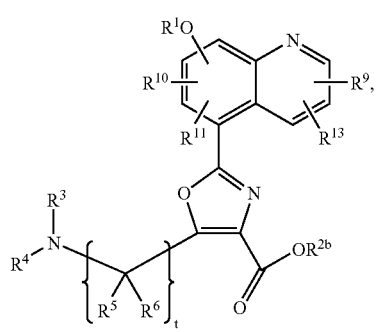

Formula IV wherein R$^1$, R$^3$, R$^4$, R$^9$, R$^{10}$, R$^{11}$, and R$^{13}$ are as defined above, and R$^{2b}$ is selected from linear, branched, or cyclic alkyl and benzyl, wherein the selected group is optionally substituted with one or more electron withdrawing groups, and wherein the selected group permits or promotes base hydrolysis of the adjacent carbonyl carbon, preferably R$^{2b}$ is a linear alkyl of 4 carbon atoms or less, more preferably R$^{2b}$ is ethyl, and R$^5$ and R$^6$ are selected independently from the group consisting of H, alkyl, hydroxyalkyl, alkoxyalkyl, mercaptoalkyl, —CH$_2$F, —CHF$_2$, —CF$_3$, —C(O)O-alkyl and —C(O)NR$^{43a}$R$^{44a}$ where R$^{43a}$ and R$^{44a}$ are independently selected for each occurrence from the group of H, alkyl, and a nitrogen protecting group, the intermediate making process comprising:

(a) reacting a compound of Formula II

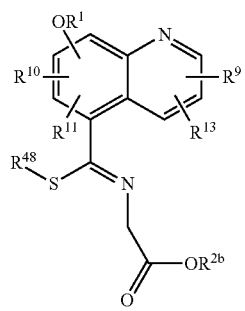

Formula II with an acylation reagent selected from:

(a) an acid anhydride compound of Formula III

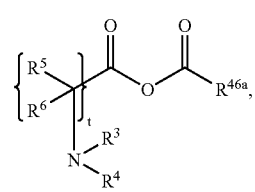

Formula III (b) an alkylestercarbonic acid anhydride compound of Formula IIIs

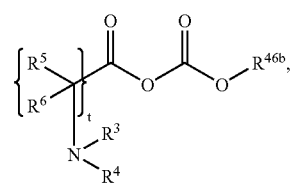

Formula IIIs (d) an N-alkoxyamide compound of Formula IIIq

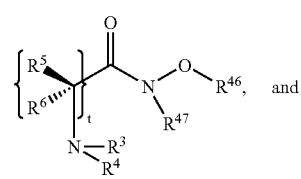

Formula IIIq and (e) an ester of Formula IIIr

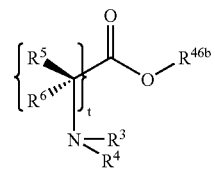

Formula IIIr wherein:

R$^{2b}$ is as defined above;

R$^5$ and R$^6$ are selected independently from the group consisting of H, alkyl, hydroxyalkyl, alkoxyalkyl, mercaptoalkyl, —CH$_2$F, —CHF$_2$, —CF$_3$, —C(O)O-alkyl and —C(O)NR$^{43a}$R$^{44a}$, where R$^{43a}$ and R$^{44a}$ are independently selected for each occurrence from the group of H, alkyl, and a nitrogen protecting group, preferably one of R$^5$ and R$^6$ is hydrogen and the other is t-butoxymethyl-;

one of R$^3$ and R$^4$ is an acid labile nitrogen protecting group and the other of R$^3$ and R$^4$ is selected from H, and linear, branched or cyclic, saturated or unsaturated alkyl;

R$^{46a}$ is a linear, branched or cyclic alkyl, optionally substituted with electron withdrawing substituents, for example, chlorine, preferably R$^{46a}$ is selected to provide stearic hinderance to nucleophilic attack on the adjacent acyl carbon, more preferably R$^{46a}$ is a t-butyl group;

R$^{46b}$ is a linear, branched, or cyclic, saturated or unsaturated alkyl, alkylaryl, or aryl group, each of which is optionally substituted with electron withdrawing groups, when substituted, preferably the substituents are selected from halogen, for example chlorine, and NO$_2$;

$R^{46}$ is selected independently for each occurrence from linear, branched, or cyclic, saturated or unsaturated alkyl, aryl, and alkaryl, each of which is optionally substituted with a halogen and —$NO_2$;

$R^{47}$ is selected independently for each occurrence from linear, branched, or cyclic, saturated or unsaturated alkyl, aryl, and alkaryl, each of which is optionally substituted with an electron withdrawing group preferably $R^{47}$ is an alkyl of 5 carbon atoms or less;

$R^{48}$ is selected independently for each occurrence from linear, branched, or cyclic electrophylic alkyl; and $R^1$, $R^9$, $R^{10}$, $R^{11}$, and $R^{13}$ are as defined above, in the presence of a Lewis base having sufficient proton affinity to abstract a proton from the carbon bonded to the nitrogen of the thioamidic acid methyl ester functional group present in the compound of Formula II.

In some embodiments it is preferred for the Lewis base used to be selected from metal amides, for example sodium amides and lithium amides; metal alkoxides, for example sodium methoxide, and metal alkyls, for example, alkyl lithium.

In some embodiments it is preferred for the acylating reagent reacted with a compound of Formula II in the presence of a Lewis base (as defined above) to be an acid anhydride of Formula IIIp,

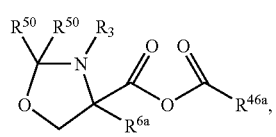

Formula IIIp where $R^3$ and $R^{46a}$ are as defined above, $R^{50}$ is selected independently for each occurrence and is selected from linear, branched, or cyclic alkyl, or taken together the two $R^{50}$ substituents form a cyclic alkyl spirocycle, preferably each $R^{50}$ is $H_3C$-(methyl) and $R^{6a}$ is selected from H and linear, branched or cyclic alkyl, to form a compound of the structure of Formula IVa:

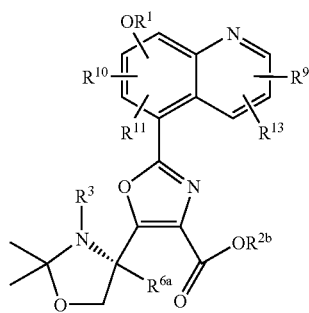

Formula IVa wherein $R^1$, $R^{2b}$, $R^3$, $R^{6a}$, $R^9$, $R^{10}$, $R^{11}$, and $R^{13}$ are as defined above.

In some embodiments using an anhydride having the structure of Formula IIIp, it is preferred for $R^3$ to be the substituent:

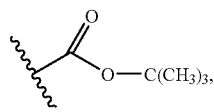

thus the compound has the structure of Formula IIIpa:

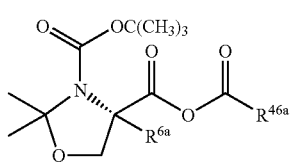

Formula IIIpa where $R^{6a}$ and $R^{46a}$ are defined above, preferably $R^{6a}$ is H and $R^{46a}$ is t-butyl, thus, the compound of Formula IIIpa has the structure of Formula IIIpa1

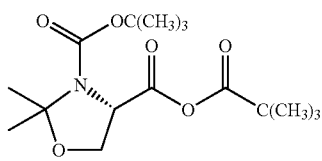

Formula IIIpa1 and produces a compound of Formula IVa having the structure of Formula IVa1,

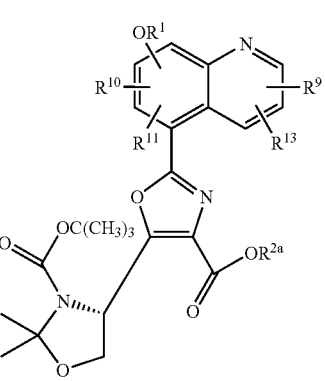

Formula IVa1

It will be appreciated that when placed in hydrolysis conditions for example, the conditions of Step 4 of Scheme IV described below, which, as described in the referenced scheme, includes, prior to Step 4, derivatizing the ester group (—O—$R^{2b}$) to an "$R^2$" group as defined above, the oxazolidine moiety on the left side of the compounds of Formula IVa (as depicted) undergo ring-opening and loss of the nitrogen protecting group to form compounds of Formula IVb.

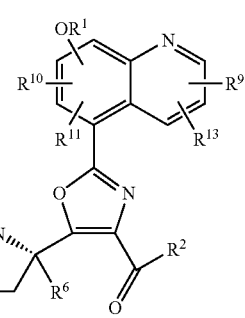

Formula IVb where $R^1$, $R^2$, $R^6$, $R^9$, $R^{10}$, $R^{11}$, and $R^{13}$ are as defined above. It will be appreciated that the intermediate compounds of Formula IV and Formula IVa provided by the above-described processes can be utilized in the various reaction schemes described throughout the '009 publication which employ oxazoline-substituted quinoline compounds having similar oxazoline substituents. Accordingly, it will be appreciated that the various substituents on the oxazoline ring of the intermediate compounds provided by the present methods can be utilized in schemes and reactions described in the '009 publication to provide equivalent oxazoline-substituted quinoline compounds, for example, the amidization reactions converting the ester moiety on the right side of the compound of Formula IVa to an amide. One example of this is described in the '009 application beginning on page 145.

In some embodiments of the present invention it is preferred for the compound of Formula II to be an 8-methoxy-2-trifluoromethyl quinoline substituted at carbon 5 with a sulfanyl-methyl-amino-acetic acid ester substituent (the compound of Formula V), wherein, $R^{2b}$ and $R^{48}$ are as defined above and are independently selected for each occurrence,

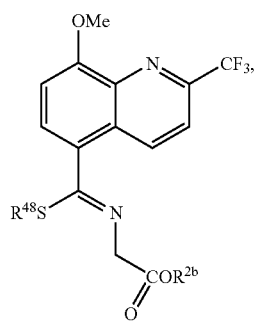

Formula V and to be reacted with an acylating reagent selected from the acylating reagents of Formula III, Formula IIIq, Formula IIIr, Formula IIIs, Formula IIIp, and Formula IIIpa as described above.

In some embodiments of the present invention, in the compound of Formula V preferably the $R^{48}$ substituent is methyl and the $R^{2a}$ substituent is ethyl.

In some embodiments of the present invention it is preferred to use an acylating reagent of Formula III, more preferably "t"=1, $R^{46a}$ is t-butyl, one of $R^3$ or $R^4$ is t-butoxycarbonyl ([$(CH_3)_3C$—O—(O)C—]) and the other is H, and one of $R^5$ or $R^6$ is t-butoxymethylene- and the other of $R^5$ and $R^6$ is H. In some embodiments, the acylating reagent of Formula III is the compound having the structure of Formula VI, a protected serine acid anhydride derivative of Formula VI,

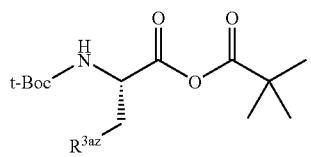

Formula VI wherein t-Boc is t-butoxycarbonyl and $R^{3az}$ is tertiarybutoxy or hydrogen.

In some embodiments of the present invention, in the acylation reaction it is preferred to use a Lewis base comprising a sterically hindered metal amide. In some embodiments it is preferred to use a Lewis base selected from lithium diisopropyl amide and sodium bistrimethylsilyl amide. In some embodiments it is preferred to employ two equivalents of the Lewis base in the acylation reaction.

In some embodiments of the present invention, preferably the oxazoline ring-forming reaction (acylation reaction) of the invention is incorporated into a larger reaction scheme, for example, it is Step II of Synthesis Scheme II, which illustrates the preparation of a PDE IV inhibitor compound of Formula 15.

Scheme II

Step 1

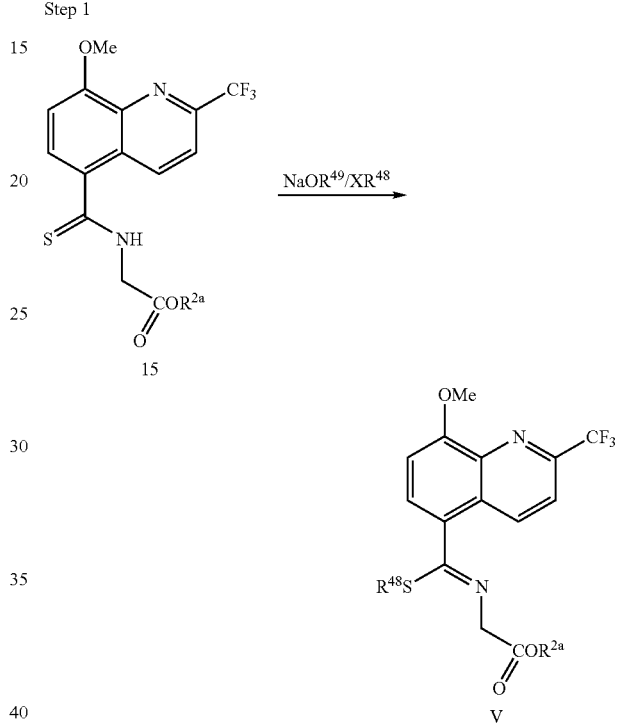

wherein $R^{48}$ is a linear, branched, or cyclic electrophilic alkyl group, preferably a linear alkyl of four carbon atoms or less, more preferably a methyl group, attached to a nucleophilic leaving group "X" selected from sulfonyl, halide, and sulfate, preferably halide, more preferably iodide, $R^{49}$ is a linear, branched, or cyclic alkyl group, preferably a linear alkyl group of 4 carbon atoms or less, more preferably ethyl (—$CH_2CH_3$) and $R^{2a}$ is as defined above;

Step 2

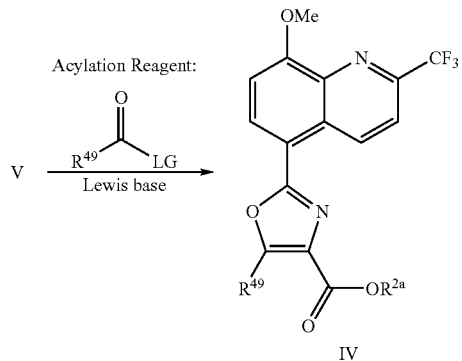

wherein $R^{49}$ and "LG" (leaving group) of the acylation reagent are selected such that the acylation reagent is:

(a) an anhydride of Formula III,

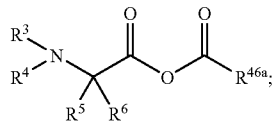

Formula III (b) an alkylestercarbonic acid anhydride compound of Formula IIIs1,

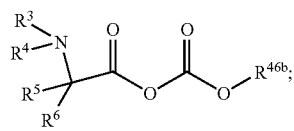

Formula IIIs1

(c) an N-alkoxyamide compound of Formula IIIq1,

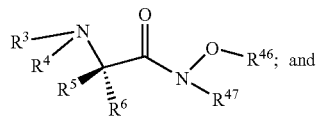

Formula IIIq1

(d) an ester of Formula IIIr1,

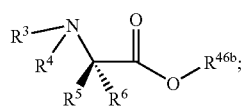

Formula IIIr1 wherein:
$R^{2b}$ is selected from linear, branched, or cyclic alkyl and benzyl, wherein the selected group is optionally substituted with one or more electron withdrawing groups, and wherein the selected group permits or promotes base hydrolysis of the adjacent carbonyl carbon, preferably $R^{2b}$ is a linear alkyl of 4 carbon atoms or less, more preferably $R^{2b}$ is ethyl;

$R^5$ and $R^6$ are selected independently from the group consisting of H, alkyl, hydroxyalkyl, alkoxyalkyl, mercaptoalkyl, —$CH_2F$, —$CHF_2$, —$CF_3$, —C(O)O-alkyl and —C(O)$NR^{43a}R^{44a}$, where $R^{43a}$ and $R^{44a}$ are independently selected for each occurrence from the group of H, alkyl, and a nitrogen protecting group, preferably one of $R^5$ and $R^6$ is hydrogen and the other is t-butoxymethyl-;

one of $R^3$ and $R^4$ is an acid labile nitrogen protecting group and the other of $R^3$ and $R^4$ is selected from H, and linear, branched or cyclic, saturated or unsaturated alkyl;

$R^{46a}$ is a linear, branched or cyclic alkyl, optionally substituted with electron withdrawing substituents, for example, chlorine, preferably $R^{46a}$ is selected to provide stearic hinderance to nucleophilic attack on the adjacent acyl carbon, more preferably $R^{46a}$ is a t-butyl group;

$R^{46b}$ is a linear, branched, or cyclic, saturated or unsaturated alkyl, alkylaryl, or aryl group, each of which is optionally substituted with electron withdrawing groups, when substituted, preferably the substituents are selected from halogen, for example chlorine, and $NO_2$;

$R^{46}$ is selected independently for each occurrence from linear, branched, or cyclic, saturated or unsaturated alkyl, aryl, and alkaryl, each of which is optionally substituted with a halogen and —$NO_2$;

$R^{47}$ is selected independently for each occurrence from linear, branched, or cyclic, saturated or unsaturated alkyl, aryl, and alkaryl, each of which is optionally substituted with an electron withdrawing group preferably $R^{47}$ is an alkyl of 5 carbon atoms or less;

$R^{48}$ is selected independently for each occurrence from linear, branched, or cyclic electrophylic alkyl; and $R^1$, $R^9$, $R^{10}$, $R^{11}$, and $R^{13}$ are as defined above;

Step 3

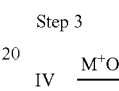

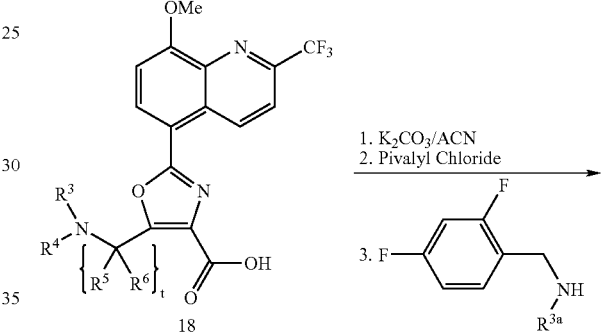

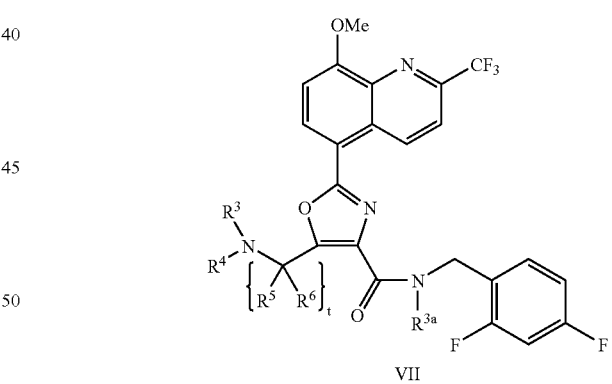

OPTIONAL Step 3

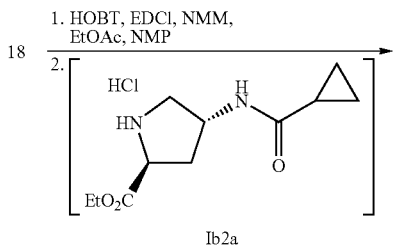

-continued

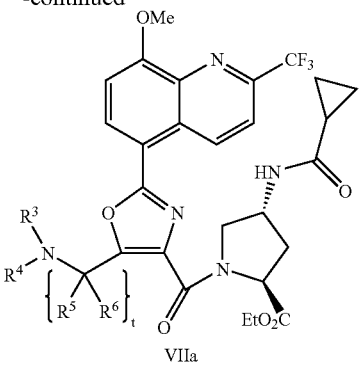
VIIa wherein M⁺ is an alkali metal, preferably Li and $R^{3a}$ is H, linear, branched, or cyclic alkyl, or a nitrogen protecting group, and $R^3$, $R^4$, $R^5$, and $R^6$ are as defined above.

In some embodiments of the process of Scheme II, it is preferred to use an acid anhydride acylation reagent in Step 2 which has the structure of Formula IIIpa1

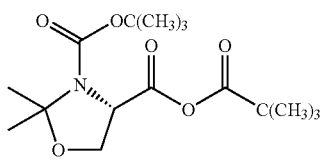
Formula IIIpa1 and produces a compound of Formula IV having the structure of Formula IVb,

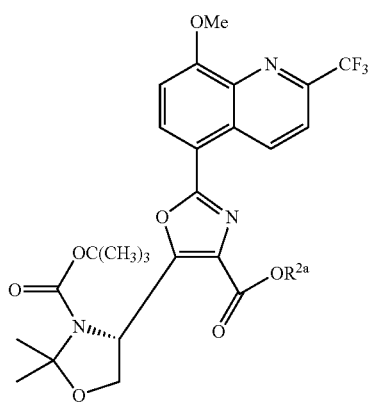
Formula IVb

With reference to Step 1 of Reaction Scheme II, in some embodiments of the present invention the conversion of [(8-Methoxy-2-trifluoromethyl-quinoline-5-carbothioyl)-amino]-acetic acid ester (15) to an alkylsulfanyl-methylene amino-acetic ester of Formula V, is preferably carried out using sodium methoxide as the alkoxide base and methyl iodide as the electrophilic alkyl group and nucleophilic leaving group.

With reference to Scheme II, in Step 2, the Lewis base used in the acylation reaction is preferably a sterically hindered metal amide base, more preferably selected from Lithium diisopropyl amide and sodium bis-trimethylsilyl amide.

In some embodiments of the present invention, illustrated in Step 3 of Scheme II, the quinolin-5-yl-oxazoline-acetic acid ester compound of Formula IV is treated with a hydroxide base, for example, LiOH, to convert the —C(O)OR$^{2a}$ ester functionality pendent on the oxazoline 4-carbon to the corresponding acid, yielding compound (18), thus providing a reactive (acid) functional group which can be further derivatized. Derivatization of the acid functional group is exemplified in Step 3 also, for example, amidation using 2,4 difluorobenzylamine.

In some embodiments using an anhydride acylation reagent, the acylation reagent is prepared from the corresponding salt of the acid, thus providing a more stable reactant. Accordingly, as shown in Scheme IIa, the anhydride is prepared by treating the acid reactant with an amine to form an ammonium salt complex. Preferably the amine used is a secondary amine, more preferably it is dicyclohexylamine. (DCHA). Subsequent treatment of the complex with an acid chloride provides the anhydride. In some embodiments, the anhydride acylating reagent thus formed can be further reacted with an alcohol, for example, 4-nitrophenol, to provide an activated ester acylating reagent.

Scheme IIa

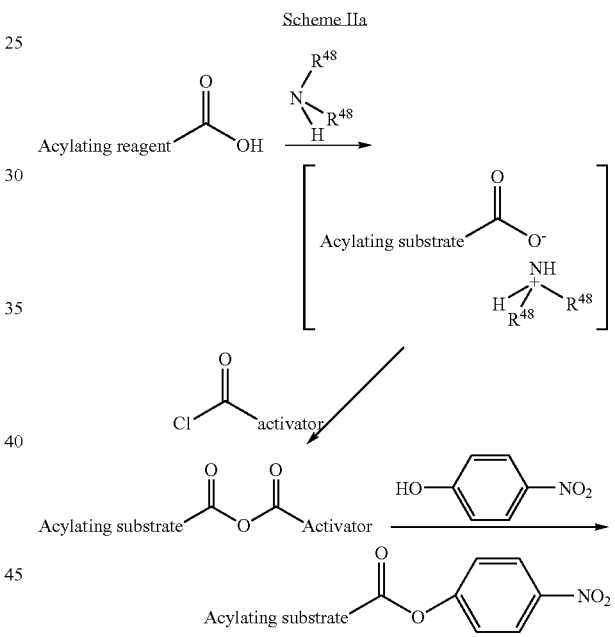

In some preferred embodiments, $R^{48}$ is

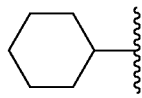

(cyclohexyl), the substrate is the moiety of Formula XX and the activator is a t-butyl moiety, thus the acid chloride is pivalyl chloride, providing, respectively, an anhydride acylating reagent of Formula IIIa1 and an ester acylating reagent of Formula IIIra1 from reaction Scheme IIa. It will be appreciated that other alcohols can be employed, preferably an alkyl alcohol selected from those comprising 4 carbon atoms or less, optionally substituted with electron withdrawing groups, or an aryl or benzyl substituted with one or more electron withdrawing groups, for example 4-nitrophenol.

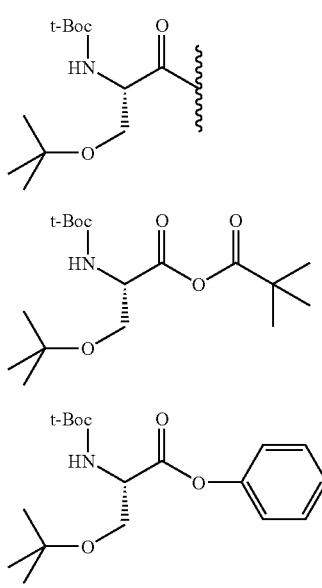
Formula XX
Formula III a1
Formula IIIra1
In some preferred embodiments, Synthesis Scheme II is carried out as shown in Synthesis Scheme III.
Scheme III
Step 1
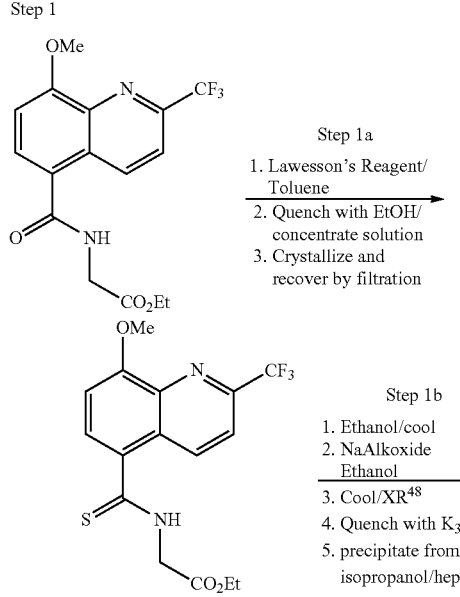
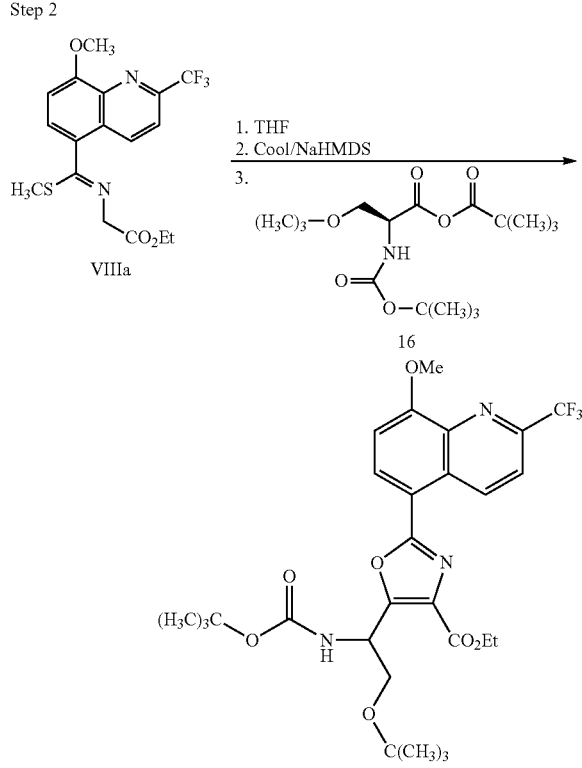
Step 3
Step 4

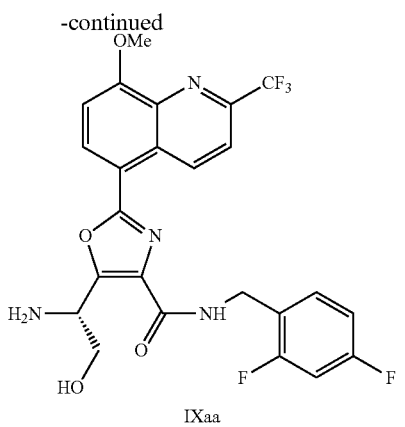

IXaa

In some embodiments of Scheme III in Step 1a: (a) it is preferred to heat the reaction mixture containing Lawesson's Reagent and toluene to a temperature of from about 80° C. to about 90° C. to carry out the reaction; (b) in Step 1 it is preferred to cool the reaction mixture to a temperature of from about 40° C. to about 60° C. to carry out the quench with ethanol; (c) it is preferred to concentrate the reaction mixture to a volume of about 20% of the initial volume; and/or (d) it is preferred to precipitate the product at a temperature of from about 0° C. to about 5° C. In some embodiments of Scheme III in Step 1b: (a) it is preferred to initially cool the reaction mixture to a temperature of from about 0° C. to about −10° C. and add the ethanolic solution of metal alkoxide, preferably sodium ethoxide, over a period of at least about 15 minutes; (b) it is preferred to cool the reaction mixture to a temperature of from about −10° C. to about −20° C. prior to adding R—X, and it is preferred to use Me-I as the R—X reagent added over a 15 minute period; (c) after addition of R—X it is preferred to warm the reaction mixture to a temperature of from about −5° C. to about +5° C. over a period of about 2.5 hours; (d) it is preferred to quench the reaction with a 3 wt % aqueous solution of $K_2CO_3$; and/or (e) it is preferred to extract the reaction mixture with a mixed solvent comprising ethylacetate and heptane and to precipitate the product from heptane.

In some embodiments of Scheme III in Step 2 it is preferred to cool the reaction mixture to a temperature of from about −60° C. to about −70° C. prior to adding the sodium amide. In some embodiments of Scheme III in Step 2 it is preferred to use at least about 2 equivalents of amide based on the amount of the compound of Formula VIII present in the reaction mixture. In some embodiments of Scheme III in Step 2 it is preferred to use a total of about 1.2 equivalents of the acylating reagent. In some embodiments of Scheme III in Step 2 it is preferred to add sequentially the base and then the acylating reagent, each in aliquots of from about 0.2 equivalents to about 0.3 equivalents based upon the amount of the compound of Formula VIII present in the reaction mixture.

In some embodiments of Scheme III in Step 3a: (a) it is preferred to use at least about 2 equivalents of LiOH based on the starting amount of the compound of Formula XII; (b) it is preferred to combine the reactants at ice bath temperature and carry out the de-esterification reaction at room temperature; (c) at the end of the reaction period it is preferred to acidify the reaction mixture to a pH of about pH=3 by titrating it with HCl; (c) it is preferred to extract the acid product from the reaction mixture with ethylacetate; and/or (e) it is preferred to dry the extracted reaction mixture by distillation after mixing in THF until the reaction mixture indicates a water content of less than about 0.05% by Karl Fischer titration. In some embodiments of Scheme III in Step 3b: (a) it is preferred to neutralize the acid product with at least 1.5 equivalents of $K_2CO_3$ and to maintain the reaction mixture at a temperature of about 15° C.; (b) it is preferred to convert the salt to an acid anhydride by treating the salt with at least about 1 equivalent of an acid chloride, preferably trimethylacetyl chloride; (c) it is preferred to react the acid anhydride with about 1 equivalent of an amine, preferably a primary amine, more preferably 2,4-difluorobenzylamine; and/or (d) it is preferred to precipitate the amidized product by adding water to the reaction mixture.

In some embodiments of Scheme III in Step 3b: (a) it is preferred to cool the reaction mixture to a temperature of from about 10° C. to about 0° C. prior t adding trifluoroacetic acid to remove protecting groups and after the addition to warm the reaction mixture to ambient temperature (about 20° C. to about 25° C.); (b) it is preferred to 4 equivalents of trifluoroacetic acid, concentrate the reaction mixture after a reaction period, preferably 12 hours, and add 2 additional equivalents of trifluoroacetic acid; (c) it is preferred to neutralize the reaction mixture by titrating into it an aqueous potassium carbonate solution; and/or (d) at the neutralization end-point, it is preferred to precipitate the product by adding water to the reaction mixture and cooling the mixture.

Another aspect of the present invention is a process for preparing a compound of Formula IXab in accordance with Scheme Ia2

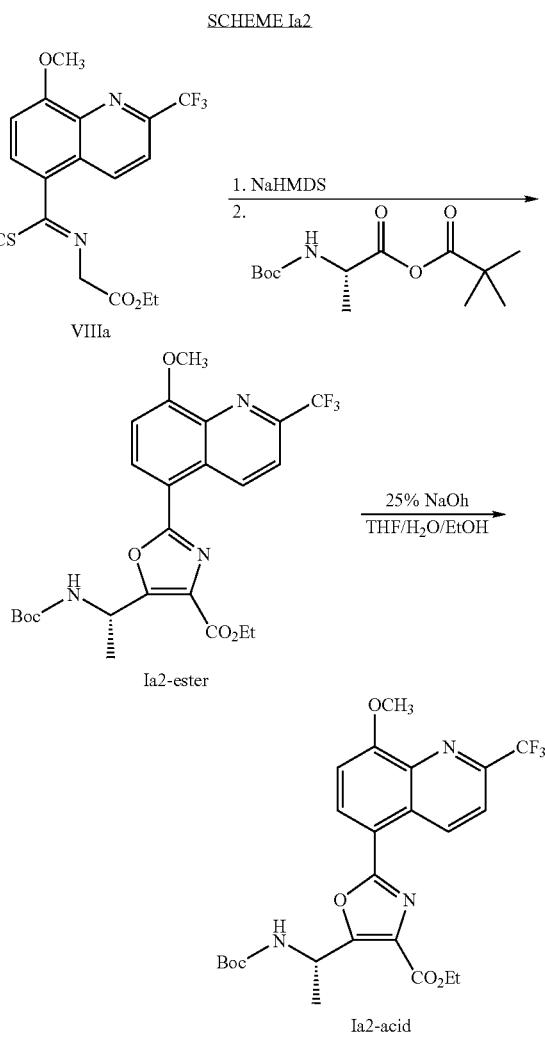

-continued

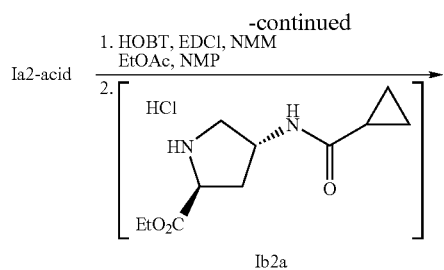
Ia2-acid

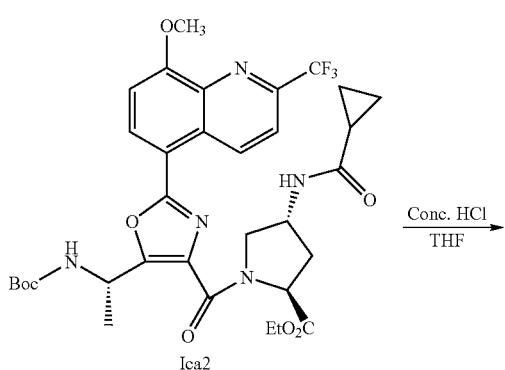
Ica2

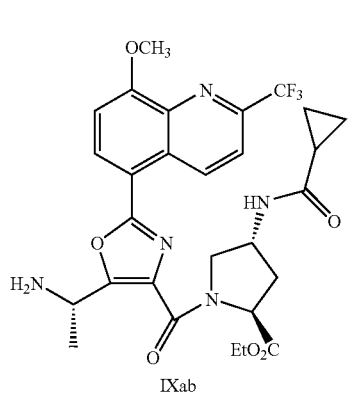
IXab the process comprising:
(a) providing the anhydride of Formula Ib1a;
(b) reacting the compound of the Formula VIIIa with an alkali metal amide base, preferably sodium bis(trimethylsilyl)amide (NaHMDS), and reacting that product with the anhydride provided in Step "a" to provide the compound of Formula Ia2-ester;
(c) converting the compound of Formula Ia2-ester to the acid of Formula Ia2-acid by treatment with aqueous base;
(d) reacting the compound of Formula Ia2-acid with the amino salt compound of the Formula Ib2a to form the compound of Formula Ic2a; and
(e) deprotecting the compound of Formula Ic2a to form the compound of Formula IXab.

In some embodiments it is preferred to carry out the provision of the anhydride of Formula Ib1a in step "a" by a process comprising reacting the compound of Formula Ib1b (N-Boc-L-alanine),

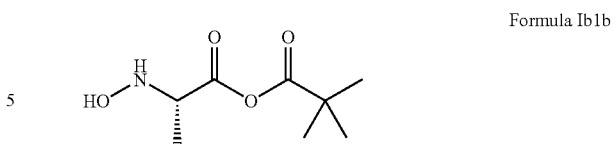
Formula Ib1b with trimethylacetylchloride in the presence of dicyclohexylamine.

In some embodiments of the inventive process, step "b" is carried out by placing the compound of Formula Ia1 in a reaction mixture, adding an aliquot of an alkali metal amide base in an amount which is less than required to react with all of the compound of Formula Ia1 present, then add an equivalent amount of the anhydride compound of Formula Ib1a, and repeat the addition of amide followed by anhydride until substantially all of the compound of Formula Ia1 has been reacted. In some embodiments of the inventive process it is preferred to add the required amount of amide in 10 separate aliquots.

In some embodiments of the inventive process it is preferred to provide the compound of Formula Ib2a by deprotecting the t-BOC-N protected precursor of Formula Ib2a1 provided by reacting the compound of Formula Ib2a1 with gaseous HCl in the presence of N-methylpyrrolidine (NMP) and ethylacetate.

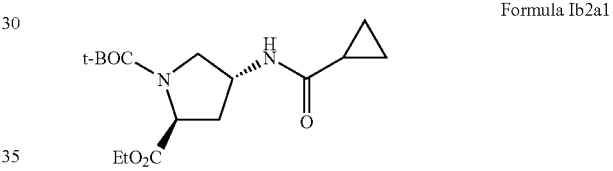
Formula Ib2a1

Other aspects and advantages of the present invention will become apparent from following Detailed Description.

DETAILED DESCRIPTION OF THE INVENTION

As mentioned above, and described in the '009 publication, compounds of Formula I (as defined herein) are useful compounds having PDE-IV inhibitor properties.

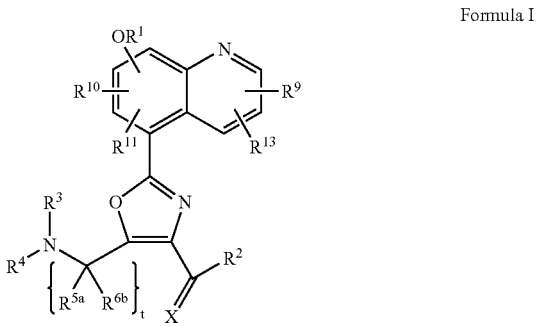
Formula I wherein:
X is O or S
$R^1$ is H, alkyl, cycloalkyl, cycloalkyl($C_1$-$C_4$)alkyl-, —$CH_2F$, —$CHF_2$, —$CF_3$, —C(O)alkyl or —C(O)$NR^{18}R^{19}$;
$R^2$ is —$OR^{2a}$ or —N($R^7$)($R^8$), wherein $R^{2a}$ is linear, branched, or cyclic alkyl or substituted linear, branched, or cyclic alkyl, and $R^7$ and $R^8$ are defined herein below;

R³ and R⁴ are independently selected from the group consisting of H, alkyl, hydroxyalkyl and —C(O)Oalkyl;

R$^{5a}$ and R$^{6b}$ are independently selected from the group consisting of H, alkyl, hydroxyalkyl, alkoxyalkyl, mercaptoalkyl, —CH$_2$F, —CHF$_2$, —CF$_3$, —C(O)OH, —C(O)Oalkyl and —C(O)NR$^{43}$R$^{44}$;

t is 1 or 2;

R$^7$ is H, alkyl, alkenyl, hydroxyalkyl, cycloalkyl, alkoxyalkyl, aminoalkyl, (R$^{17}$-phenyl)alkyl or —CH$_2$—C(O)—O-alkyl;

R$^8$ is H, alkyl, alkenyl, alkoxy, alkoxyalkyl, hydroxyalkyl, dihydroxyalkyl, alkyl-NR$^{18}$R$^{19}$, cyanoalkyl, R$^{23}$-heteroaryl, R$^{23}$-heteroarylalkyl, (R$^{36}$-heterocycloalkyl)alkyl, R$^{17}$-phenyl, (R$^{17}$-phenyl)alkyl, R$^{17}$-naphthyl, (R$^{17}$-naphthyl)alkyl, R$^{17}$-benzyloxy, -alkyl-C(O)—NR$^{18}$R$^{19}$, -alkyl-C(O)—N(R$^{30}$)—(R$^{23}$-heteroaryl), -alkyl-C(O)—N(R$^{30}$)-(cycloalkyl), -alkyl-C(O)—(R$^{36}$-heterocycloalkyl); -alkyl-N(R$^{30}$)—C(O)Oalkyl, -alkyl-N(R$^{30}$)—C(O)—NR$^{18}$R$^{19}$, -alkyl-N(R$^{30}$)—C(O)alkyl, -alkyl-N(R$^{30}$)—C(O)-(fluoroalkyl), -alkyl-N(R$^{30}$)—C(O)—(R$^{39}$-cycloalkyl), -alkyl-N(R$^{30}$)—C(O)—(R$^{17}$-phenyl), -alkyl-N(R$^{30}$)—C(O)—(R$^{23}$-heteroaryl), -alkyl-N(R$^{30}$)—C(O)-alkylene-(R$^{23}$-heteroaryl), -alkyl-NH—SO$_2$—NR$^{18}$R$^{19}$, -alkyl-N(R$^{30}$)—(R$^{17}$-phenyl), -alkyl-N(R$^{30}$)—(R$^{23}$-heteroaryl), -alkyl-O—(R$^{17}$-phenyl), -alkyl-O—(R$^{23}$-heteroaryl), -alkyl-N(R$^{30}$)—SO$_2$-alkyl, R$^{45}$-hydroxyalkyl, dihydroxyalkyl substituted by R$^{17}$-benzyloxy, dihydroxyalkyl substituted by R$^{17}$-phenyl, alkoxyalkyl substituted by R$^{17}$-phenyl, (R$^{17}$-phenyl)alkyl substituted by —CO$_2$alkyl, (R$^{17}$-phenyl)alkyl substituted by —C(O)NH$_2$, alkyl substituted by (R$^{23}$-heteroaryl) and —C(O)NR$^{37}$R$^{38}$, R$^{12}$-cycloalkyl, (R$^{12}$-cycloalkyl)alkyl,

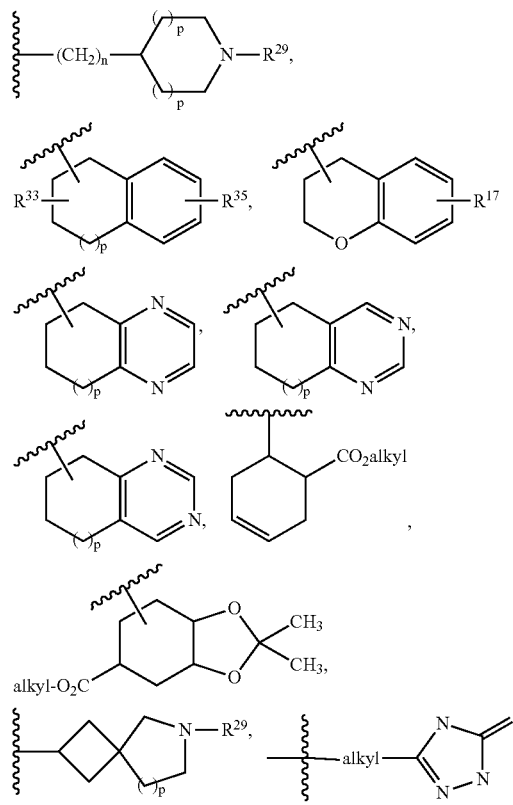

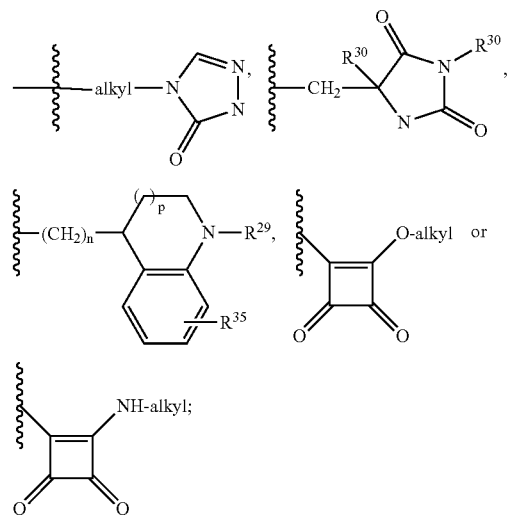

or R$^7$ and R$^8$ and the nitrogen to which they are attached together form a ring system selected from the group consisting of

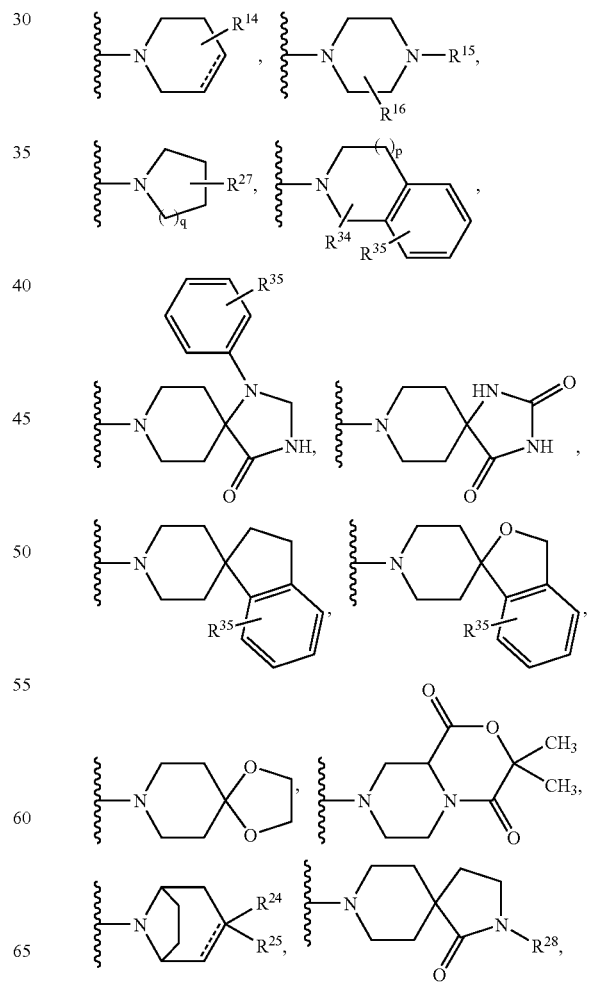

-continued

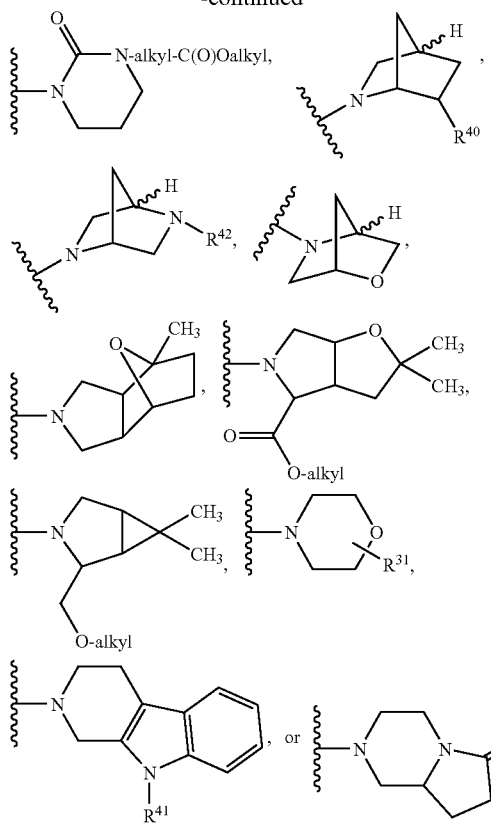

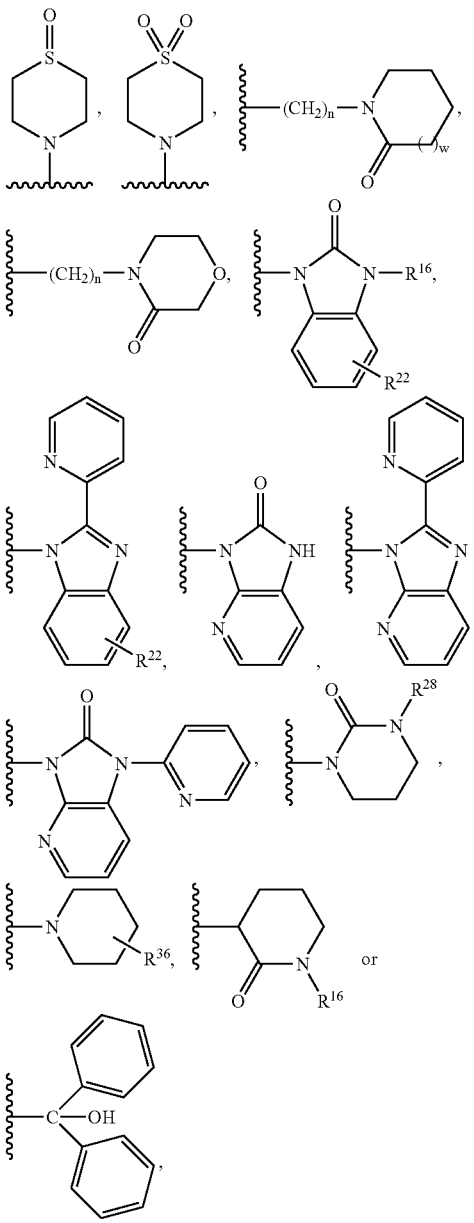

p is 0 or 1;
q is 0 or 1;
the dotted line represents an optional double bond;
$R^9$ is H, halo, alkyl, cycloalkyl, —CH$_2$F, —CHF$_2$ or CF$_3$;
$R^{10}$, $R^{11}$, and $R^{13}$ are independently selected from the group consisting of H and halo;
$R^{12}$ is 1-3 substituents independently selected from the group consisting of H, alkyl, hydroxy, alkoxy, hydroxyalkyl, alkoxyalkyl, —C(O)Oalkyl, —(CH$_2$)$_n$—N(R$^{30}$)—C(O)-cycloalkyl, —(CH$_2$)$_n$—N(R$^{30}$)—C(O)alkyl, —(CH$_2$)$_n$—N(R$^{30}$)—C(O)Oalkyl, —(CH$_2$)$_n$—N(R$^{30}$)—(R$^{23}$-heteroaryl), —(CH$_2$)$_n$—N(R$^{30}$)—C(O)—NR$^{18}$R$^{19}$ and —(CH$_2$)$_n$—C(O)—NR$^{18}$R$^{19}$;
$R^{14}$ is 1 or 2 substituents independently selected from the group consisting of H, OH, halo, alkyl, alkoxy, hydroxyalkyl, alkoxyalkyl, —CF$_3$, CN, R$^{17}$-phenyl, (R$^{17}$-phenyl)alkyl, —NR$^{18}$R$^{19}$, alkyl-NR$^{18}$R$^{19}$, —(CH$_2$)$_n$—C(O)OH, —(CH$_2$)$_n$—C(O)Oalkyl, —(CH$_2$)$_n$—C(O)alkyl, —(CH$_2$)$_n$—C(O)(R$^{35}$-phenyl), —(CH$_2$)$_n$—C(O)(R$^{23}$-heteroaryl), —(CH$_2$)$_n$—C(O)NR$^{18}$R$^{19}$, —(CH$_2$)$_n$—C(O)N(R$^{30}$)—(CH$_2$)—(R$^{23}$-heteroaryl), —(CH$_2$)$_n$—N(R$^{30}$)—C(O)alkyl, —(CH$_2$)$_n$—N(R$^{30}$)—C(O)-(fluoroalkyl), —(CH$_2$)$_n$—N(R$^{30}$)—C(O)-(cycloalkyl), —(CH$_2$)$_n$—N(R$^{30}$)—C(O)(R$^{35}$-phenyl), —(CH$_2$)—N(R$^{30}$)—C(O)(R$^{23}$-heteroaryl), —(CH$_2$)$_n$—N(R$^{30}$)C(O)NR$^{18}$R$^{19}$, —(CH$_2$)$_n$—N(R$^{30}$)—C(O)Oalkyl, —(CH$_2$)$_n$—N(R$^{30}$)cycloalkyl, —(CH$_2$)—N(R$^{30}$)(R$^{17}$-phenyl), —(CH$_2$)$_n$—N(R$^{30}$)(R$^{23}$-heteroaryl), —(CH$_2$)$_n$—N(R$^{18}$)SO$_2$alkyl, —(CH$_2$)$_n$—N(R$^{20}$)SO$_2$—(R$^{17}$-phenyl), —(CH$_2$)$_n$—N(R$^{30}$)SO$_2$—CF$_3$, —CH$_2$S(O)$_{0-2}$(R$^{35}$-phenyl), —(CH$_2$)$_n$—OC(O)N(R$^{30}$)alkyl, R$^{23}$-heteroaryl, (R$^{23}$-heteroaryl)alkyl, (R$^{23}$-heteroaryl)oxy, (R$^{23}$-heteroaryl)amino, —CH(OH)—(R$^{17}$-phenyl), —CH(OH)—(R$^{23}$-heteroaryl), —C(=NOR$^{30}$)—(R$^{17}$-phenyl), —C(=NOR$^{30}$)—(R$^{23}$-heteroaryl), morpholinyl, thiomorpholinyl, w is 0 or 1;
or two R$^{14}$ substituents and the carbon to which they are both attached form —C(=NOR$^{30}$)— or —C(O)—;
each n is independently 0, 1, 2 or 3;
$R^{15}$ is H, alkyl, cycloalkyl, (cycloalkyl)alkyl, hydroxyalkyl, alkoxyalkyl, —C(O)Oalkyl, —C(O)O(R$^{30}$-cycloalkyl), -alkyl-C(O)O-alkyl, —C(O)O-alkylene-(R$^{35}$-phenyl), R$^{17}$-phenyl, (R$^{17}$-phenyl)alkyl, —CH—(R$^{17}$-phenyl)$_2$, R$^{23}$-heteroaryl, —(CH$_2$)$_n$—C(O)NR$^{18}$R$^{19}$, —SO$_2$-alkyl, —SO$_2$-cycloalkyl, —SO$_2$—CF$_3$, —SO$_2$—(R$^{35}$-phenyl), —SO$_2$—NR$^{18}$R$^{19}$, —C(O)alkyl, —C(O)-(fluoroalkyl), —C(O)—C(CH$_3$)(CF$_3$)$_2$, —C(O)—(R$^{17}$-phenyl), —C(O)—(R$^{23}$-heteroaryl), —C(O)-hydroxyalkyl, —C(O)-alkoxyalkyl, —C(O)—(R$^{39}$-cycloalkyl), —C(O)-alkylene-(R$^{17}$-phenyl), —C(O)-alkylene-(R$^{23}$-heteroaryl), —C(O)- alkylene-S—C(O)alkyl, —C(=S)—(R$^{17}$-phenyl), hydroxyalkyl substituted by R$^{17}$-phenyl, hydroxyalkyl substituted by R$^{23}$-heteroaryl, alkoxyalkyl substituted by R$^{17}$-phenyl, alkoxyalkyl substituted by R$^{23}$-heteroaryl,

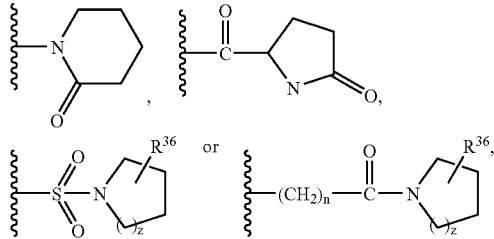

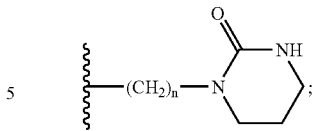

wherein z is 0, 1 or 2;

R$^{16}$ is 1 to 4 substituents independently selected from the group consisting of H, alkyl, R$^{17}$-phenyl, (R$^{17}$-phenyl)alkyl, (R$^{23}$-heteroaryl)alkyl, hydroxyalkyl, alkoxyalkyl and —C(O)Oalkyl, or two R$^{16}$ groups and the carbon to which they are both attached form —C(O)—;

R$^{17}$ represents 1 to 3 substituents replacing a hydrogen on a phenyl moiety, each of which is independently selected from the group consisting of halo, alkyl, cycloalkyl, —OH, hydroxyalkyl, alkoxy, —CN, —CF$_3$, —OCF$_3$, —OCHF$_2$, —OCH$_2$F, —C(O)OH, —C(O)Oalkyl, —C(O)O—(R$^{35}$-phenyl), —C(O)alkyl, —C(O)—(R$^{35}$-phenyl), —SOalkyl, —SO$_2$alkyl, —SO$_2$—CF$_3$, alkylthio, —NR$^{43}$R$^{44}$, -alkyl-NR$^{43}$R$^{44}$ and heteroaryl; or two R$^{17}$ substituents on adjacent carbon atoms together form —O—CH$_2$—O—, —O—(CH$_2$)$_2$—O—, —(CH$_2$)$_2$—O— or —O—CH$_2$—O—CH$_2$—;

R$^{18}$ and R$^{19}$ are independently selected from the group consisting of H, alkyl, hydroxyalkyl, alkoxyalkyl, R$^{17}$-phenyl and (R$^{17}$-phenyl)alkyl;

R$^{20}$ is H, alkyl, or cycloalkyl;

R$^{22}$ is 1 to 4 substituents independently selected from the group consisting of H, alkyl, hydroxy, alkoxy, halo, —CF$_3$, —NH$_2$ and R$^{35}$-phenyl;

R$^{23}$ is 1 to 4 substituents independently selected from the group consisting of H, alkyl, hydroxy, alkoxy, halo, —CF$_3$, —NR$^{18}$R$^{19}$, —CN, —C(O)Oalkyl, —NHSO$_2$-alkyl and R$^{35}$-phenyl;

R$^{24}$ is H, OH or alkoxy; or when the optional double bond is present, R$^{24}$ and the adjacent carbon atom form the double bond;

R$^{25}$ is H or R$^{35}$ phenyl;

R$^{27}$ is 1 to 3 substituents independently selected from the group consisting of H, halo, OH, alkyl, alkoxy, hydroxyalkyl, alkoxyalkyl, —CF$_3$, —CN, —C(O)OH, —C(O)Oalkyl, —C(O)N(R$^{30}$)(R$^{18}$), —C(O)—(R$^{36}$heterocycloalkyl), R$^{17}$-phenyl, (R$^{17}$-phenyl)-alkyl, R$^{23}$-heteroaryl, (R$^{23}$-heteroaryl)alkyl, (R$^{23}$-heteroaryl)oxy, (R$^{23}$-heteroaryl)amino NR$^{18}$R$^{19}$, NR$^{18}$R$^{19}$-alkyl, —(CH$_2$)$_n$—N(R$^{30}$)—C(O)alkyl, —(CH$_2$)$_n$—N(R$^{30}$)—C(O)-(fluoroalkyl), —(CH$_2$)$_n$—N(R$^{30}$)—C(O)alkoxyalkyl, —(CH$_2$)$_n$—N(R$^{30}$)—C(O)(cycloalkyl), —(CH$_2$)$_n$—N(R$^{30}$)—(R$^{23}$-heteroaryl), —(CH$_2$)$_n$—N(R$^{30}$)—C(O)—(R$^{23}$-heteroaryl), —(CH$_2$)$_n$—N(R$^{30}$)—C(O)O-alkyl, —(CH$_2$)$_n$—N(R$^{30}$)—C(O)O—(CF$_3$-alkyl), —(CH$_2$)$_n$—N(R$^{30}$)—C(O)O—(R$^{39}$-cycloalkyl), —(CH$_2$)$_n$—N(R$^{30}$)—C(O)O-alkylene-cycloalkyl, —(CH$_2$)$_n$—N(R$^{30}$)—C(O)—N(R$^{30}$)(R$^{20}$), —(CH$_2$)$_n$—N(R$^{30}$)—SO$_2$-alkyl, —(CH$_2$)$_n$—N(R$^{30}$)—SO$_2$—CF$_3$, —(CH$_2$)$_n$—N(R$^{30}$)—SO$_2$—N(R$^{30}$)$_2$ and or two R$^{27}$ groups and the carbon to which they are both attached form —C(=NOR$^{30}$)— or —C(O)—;

R$^{28}$ is H, alkyl, R$^{35}$-benzyl or -alkyl-C(O)O-alkyl;

R$^{29}$ is alkyl, —C(O)Oalkyl, —C(O)alkyl, —C(O)cycloalkyl, —C(O)—(R$^{17}$-phenyl), —C(O)—(R$^{23}$-heteroaryl), —SO$_2$-alkyl, —SO$_2$—(R$^{35}$-phenyl), —C(O)NR$^{18}$R$^{19}$, R$^{35}$-phenyl, (R$^{35}$-phenyl)alkyl or R$^{23}$-heteroaryl;

R$^{30}$ is independently selected from the group consisting of H, alkyl and R$^{35}$-benzyl;

R$^{31}$ is H, alkyl, R$^{35}$-benzyl or phenoxyalkyl;

R$^{33}$ is H, OH or alkoxy;

R$^{34}$ is H, alkyl, hydroxyalkyl, alkoxyalkyl or —C(O)Oalkyl;

R$^{35}$ is 1 to 3 substituents independently selected from the group consisting of H, halo, alkyl, OH, —CF$_3$ and alkoxy;

R$^{36}$ is 1 or 2 substituents independently selected from the group consisting of H, alkyl, R$^{17}$-phenyl, alkoxyalkyl and —C(O)Oalkyl; or two R$^{36}$ groups and the carbon to which they are both attached form —C(=NOR$^{30}$)— or —C(O)—;

R$^{37}$ and R$^{38}$ are independently selected from the group consisting of H and alkyl, or R$^{37}$ and R$^{38}$ together are —(CH$_2$)$_3$— or —(CH$_2$)$_4$—, and together with the nitrogen to which they are attached, form a ring;

R$^{39}$ is H, OH, alkyl, alkoxy, or CF$_3$;

R$^{40}$ is —OR$^{30}$ or —NHC(O)alkyl;

R$^{41}$ is H or —SO$_2$alkyl;

R$^{42}$ is —(CH$_2$)$_n$—(R$^{35}$-phenyl), —(CH$_2$)$_n$—(R$^{23}$-heteroaryl), —C(O)Oalkyl or —C(O)alkyl;

R$^{43}$ and R$^{44}$ are independently selected from the group consisting of H and alkyl; and R$^{45}$ is 1 or 2 substituents independently selected from the group consisting of halo, alkoxyalkyl, —CO$_2$alkyl, R$^{17}$-phenyl, R$^{23}$-heteroaryl and cycloalkyl.

One preferred example of a compound of Formula I, which is known to have PDE-IV inhibition properties is the compound of Formula IXaa wherein, with reference to the compound of Formula I, "t" is 1, X is O, each of R$^3$, R$^4$, and R$^5$ are H, R$^6$ is hydroxy, and R$^2$ is 2,4 difluorobenzylamide.

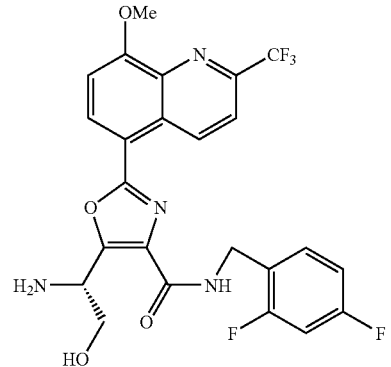

Formula IXaa

One aspect of the present invention is a novel process for the provision of compounds of Formula I, including the compound of Formula IXaa, in accordance with Scheme IV below. The process of the present invention method provides an improved procedure, for example, eliminating column chromatography and utilizing less aggressive reagents, and/or more available reagents, and/or provides a synthetic process which is more amenable to scale-up to a size suitable for the preparation of commercial quantities of these compounds.

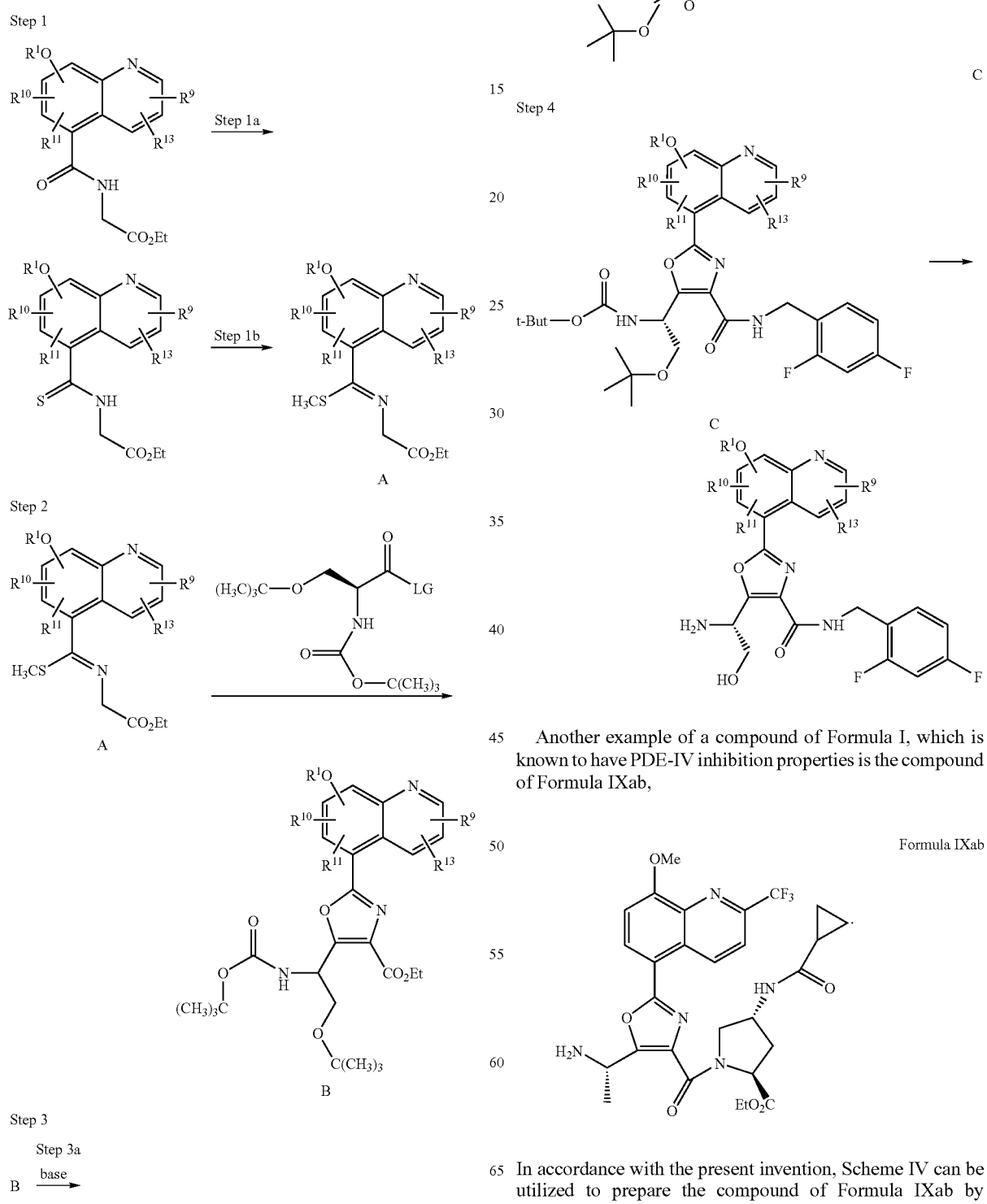

Another example of a compound of Formula I, which is known to have PDE-IV inhibition properties is the compound of Formula IXab, In accordance with the present invention, Scheme IV can be utilized to prepare the compound of Formula IXab by employing in step 2 an acylating reagent having the structure

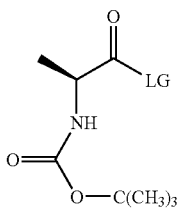

in place of the acylating reagent shown, and in step 3 an amine salt having the structure,

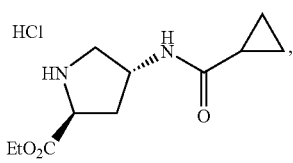

in place of the amine shown.

The novel methods and intermediates of the present invention are described and illustrated below using various reaction schemes and terms.

In some of the synthesis schemes herein illustrating some aspects of the invention there appears substrates having a quinolyl portion bearing methoxy and trifluoromethyl substituents in accordance with the quinolyl fragment of Formula XIa:

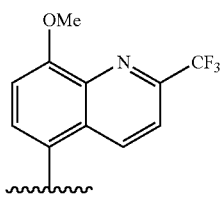

Formula XIa however, it will be appreciated that the synthesis schemes of the present invention illustrated with such oxazoline-substituted quionlines can be carried out also using substrates having a quinolyl portion bearing the various substituents (or a protected form or precursors thereof occupying the appropriate position where reactivity would preclude the direct presence of such a substituent) described above for the compounds of Formulae I and IV. With reference to, for example, Synthesis Scheme III (above), it will be appreciated also that the synthesis of some preferred compounds of Formula I, for example, a compounds of Formulae IXaa and IXab, shown herein, are prepared from substrates possessing substituents prone to unwanted reaction under the conditions of the synthesis, for example, the hydroxy-amine substituent on the oxazoline ring. Accordingly, it will be appreciated that the synthesis of compounds utilizing substrates having certain sensitive substituents may require that the sensitive substituents be protected with known protecting groups to preserve them and avoid unwanted side reactions during various synthetic steps. It will be appreciated also that providing a desired compound utilizing the synthesis steps of the present invention may require additional steps to be carried out to arrive at the final desired product in which reactive functional groups are derivatized. Examples of such additional steps include, but are not limited to, reduction of a reducible functional group and the oxidation of an oxidizable functional group. Examples include also derivitization of reactive functional groups to provide compounds with the desired substituent such as are described in the '009 publication, which description is incorporated herein by reference.

Abbreviations used herein both in the general schemes and in the examples and throughout the specification, are as follows: Me (methyl); Bu (butyl); t-But (tertiary butyl); Et (ethyl); Ac (acetyl); t-Boc or t-BOC (t-butoxycarbonyl); DMF (dimethyl-formamide); THF (tetrahydrofuran); DIPEA (diisopropylethylamine); RT (room temperature, generally 25° C.); HOBt (hydroxybenzotriazole); TFA (trifluoroaceticacid); TEA (triethylamine); KHMDS (potassium bis(trimethylsilyl)amide); TLC (thin layer chromatography); EDC (1-(3-dimethylaminopropyl)-3-ethyl-carbodiimide hydrochloride); HMPA (hexamethylphosphoramide); DMPU (1,3-dimethyl-3,4,5,6-tetrahydro-2(1H)-pyrimidinone); TMEDA (N,N,N',N'-tetramethyletheylenediamine); HATU (O-(7-azabenzotriazol-1-yl)-N,N,N',N'tetramethyl uranium hexafluoro-phosphate); NBS (N-bromosuccinimide); DCC (1,3-dicyclohexylcarbodiimide); DEC (1,2-diethylaminoethyl chloride hydrochloride); TMSCN (trimethylsilylcyanide); CDI (carbonyldiimidazole); PyBOP (benzotriazol-1-yloxytripyrrolidinophosphonium hexafluorophosphate).

As used herein the following terms, unless otherwise indicated, are understood to have the following meanings:

The term "substituted" means that one or more hydrogens on the designated atom or group of atoms in a structure is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

"Patient" includes both humans and animals.

"Mammal" means humans and other mammalian animals.

"Alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

"Alkenyl" means an aliphatic hydrocarbon group containing at least one carbon-carbon double bond and which may be straight or branched and comprising about 2 to about 6 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methyl-but-2-enyl and n-pentenyl.

"Alkylene" means a difunctional group obtained by removal of a hydrogen atom from an alkyl group that is defined above. Non-limiting examples of alkylene include methylene (i.e., —CH$_2$—), ethylene (i.e., —CH$_2$—CH$_2$—) and branched chains such as —CH(CH$_3$)—CH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyridopyrimidinyl and 7-azaindolyl. Examples of benzofused heteroaryl groups are indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl. The term $R^{23}$-heteroaryl refers to such groups wherein substitutable ring carbon atoms have a substituent as defined above. When the heteroaryl group is a benzofused ring, the substituents can be attached to either or both the phenyl ring portion and the heteroaromatic ring portion, and the heteroaryl group can be attached to the rest of the molecule either through the phenyl ring portion or the heteroaromatic ring portion.

"Cycloalkyl" means a non-aromatic mono- or multicyclic ring system comprising about 3 to about 10 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Monocyclic rings are preferred.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above; in particular, fluoroalkyl refers to an alkyl chain substituted by one or more fluoro atoms.

"Aminoalkyl" means an alkyl as defined above wherein a hydrogen atom on the alkyl is replaced by an amino (i.e., $-NH_2$) group.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain 5 to 6 ring atoms. The prefix aza, oxa or thia before the heterocycloalkyl root name means that at least a nitrogen, oxygen or sulfur atom respectively is present as a ring atom. The nitrogen or sulfur atom of the heterocyclyl can be optionally oxidized to the corresponding N-oxide, S-oxide or S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"(Heterocycloalkyl)alkyl" means a heterocycloalkyl-alkyl group in which the heterocycloalkyl and alkyl groups are as defined above. The bond to the parent is through the alkyl.

"(Heteroaryl)alkyl" means a heteroaryl-alkyl-group in which the heteroaryl and alkyl are as previously described. Non-limiting examples of suitable heteroarylalkyl groups include pyridylmethyl, 2-(furan-3-yl)ethyl and quinolin-3-ylmethyl. The bond to the parent moiety is through the alkyl.

"(Phenyl)alkyl and "(naphthyl)alkyl similarly mean phenyl-alkyl and naphthyl-alkyl groups wherein the bond to the parent moiety is through the alkyl.

"Hydroxyalkyl" means a HO-alkyl-group in which alkyl is as previously defined. Non-limiting examples of suitable hydroxyalkyl groups include hydroxymethyl and 2-hydroxyethyl. Similarly, "dihydroxyalkyl" refers to a straight or branched alkyl chain substituted by two hydroxy groups.

"Alkoxy" means an alkyl-O— group in which the alkyl group is as previously described. Non-limiting examples of suitable alkoxy groups include methoxy, ethoxy, n-propoxy, isopropoxy, t-butoxy, and n-butoxy. The bond to the parent moiety is through the ether oxygen.

"Alkylthio" means an alkyl-S— group in which the alkyl group is as previously described. Non-limiting examples of suitable alkylthio groups include methylthio, ethylthio and isopropylthio. The bond to the parent moiety is through the sulfur.

Alkylsulfuryl means an —C(—S-alkyl)=N— group, for example, in the methyl-sulfuryl substituted quinolinyl precursor described herein in the formation of the oxazoline ring:

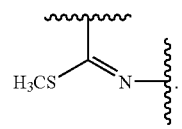

"Heteroarylamino" means an heteroaryl-NH— group in which the heteroaryl group is as previously described. Non-limiting examples of suitable heteroarylamino groups include pyrimidinyl-amino and pyrazinyl-amino. The bond to the parent moiety is through the amino nitrogen.

"Heteroaryloxy" means an heteroaryl-O— group in which the heteroaryl group is as previously described. Non-limiting examples of suitable heteroaryloxy groups include pyrimidinyl-O— and pyrazinyl-O—. The bond to the parent moiety is through the ether oxygen.

The term "hydroxyalkyl substituted by $CO_2$alkyl" means an alkyl chain substituted by a hydroxy group and a $CO_2$alkyl group. Similarly, terms such as "hydroxyalkyl substituted by $R^{17}$-phenyl" means an alkyl chain substituted by a hydroxy group and a $R^{17}$-phenyl group; "hydroxyalkyl substituted by $R^{17}$-phenyl and alkoxy" means an alkyl group substituted by a hydroxy group, a $R^{17}$-phenyl, and an alkoxy group. In each of these substituents and other similar substituents listed in the definitions, the alkyl chains can be branched.

Examples of moieties formed when two adjacent $R^{17}$ groups form a ring with the carbons on the phenyl ring to which they are attached are:

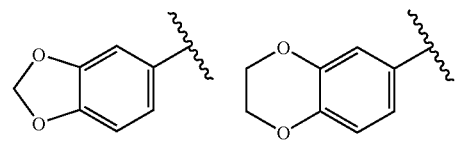

-continued

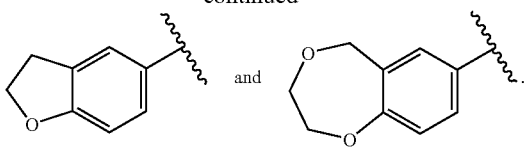

When R⁷ and R⁸ together form

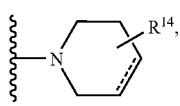

the dotted line indicates an optional double bond as defined above. When the double bond is absent, i.e., when a single bond is present, the one or two R¹⁴ substituents can be attached to the same or different ring carbons. When the double bond is present, only one R¹⁴ substituent can be attached to a carbon that is part of the double bond.

When R⁷ and R⁸ together form

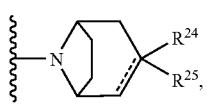

the dotted line indicates an optional double bond as defined above. When the double bond is absent, i.e., when a single bond is present, R²⁴ can be H, OH or alkoxy and R²⁵ can be H or R³⁵-phenyl, but when the double bond is present, R²⁴ forms the double bond with the adjacent carbon and R²⁵ is H or R³⁵-phenyl. That is, the moiety has the structural formula

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

A wavy line ∿∿∿ appearing on a structure and joining a functional group to the structure in the position of a bond generally indicates a mixture of, or either of, the possible isomers, e.g., containing (R)- and (S)-stereochemistry. For example,

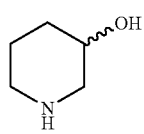

means containing both

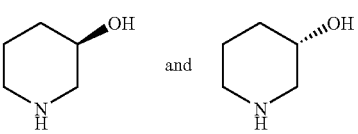

A wavy line which terminates a bond indicates that the portion of the structure depicted is attached to a larger structure at the indicated bond, for example,

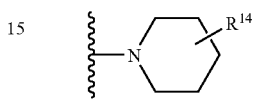

implies that the nitrogen of the substituted piperdyl group depicted is bonded to an undipicted structure on which it is a substituent.

Lines drawn into the ring systems, for example:

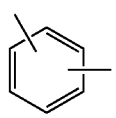

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

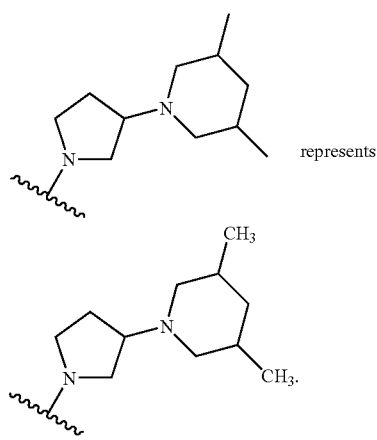

represents

However, sometimes in the examples herein, the CH₃ moiety is explicitly included in a structure. As used herein, the use of either convention for depicting methyl groups is meant to be equivalent and the conventions are used herein interchangeably for convenience without intending to alter the meaning conventionally understood for either depiction thereby.

It should also be noted that any carbon or heteroatom with unsatisfied valences in the text, schemes, examples, structural formulae, and any Tables herein is assumed to have the hydrogen atom or atoms to satisfy the valences.

It should also be noted that any heteroatom with unsatisfied valences is assumed to have the hydrogen atom(s) to satisfy the valences.

When any variable (e.g., aryl, heterocycle, $R^2$, etc.) occurs more than one time in any constituent or in a formula, unless otherwise noted, its definition on each occurrence is independent of its definition at every other occurrence.

There follows a discussion in greater detail of each of the steps of the inventive method (in numerical order) presented in Scheme IV above.

Step 1—Formation of {(Quinolin-5-yl)-Alkyl-Sulfanyl-Methylene]-Amino}-Acetic Acid Ester (Compound VIII Shown in Scheme III, Above)

The process of the present invention provides quinolin-5-yl-alkyl-sulfanyl-methylene-amino-acetic acid ester compounds, useful intermediates in the provision of the compounds of Formula I, in accordance with the process schematically presented above in Scheme IIa and in Scheme Iva below.

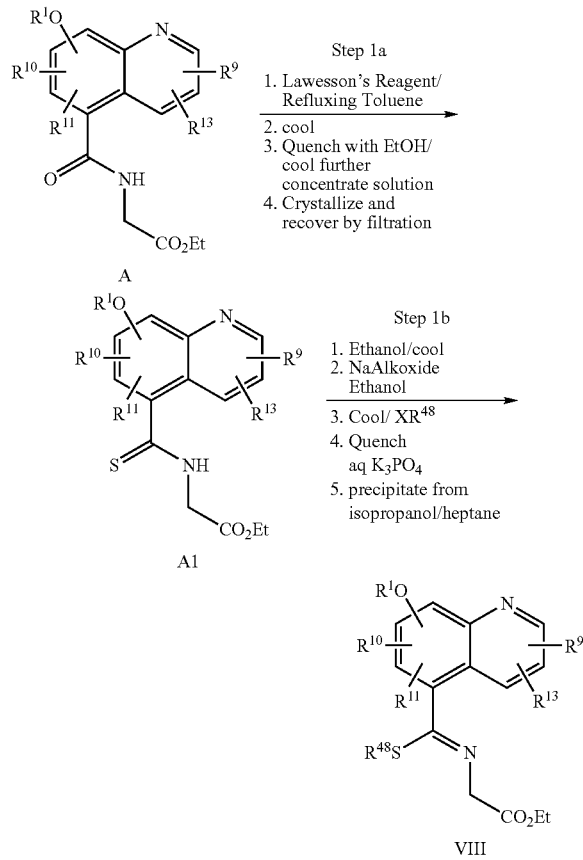

In some embodiments, the process of the present invention utilizes, in Step 1a of Step 1, Lawesson's reagent in toluene at a temperature of from about 85° C. to about 90° C. to convert [(quinoline-5-carbonyl)-amino]-acetic acid ethyl ester compounds (A, Schemes IIb and IVa) to the corresponding [(quinoline-5-carbothioyl)-amino]-acetic acid ethyl ester compound (A1). When the conversion is complete, the reaction mixture is cooled, at least to a temperature below the boiling point of ethanol, preferably to a temperature of about 60° C. or lower, and ethanol is added to quench the reaction. In some embodiments it is preferred to use at least about 2 equivalents of ethanol based on the amount of Lawesson's reagent employed, preferably about 2.2 equivalents based on the amount of Lawesson's reagent employed) to quench the reaction. Following quenching, it is preferred to further cool the reaction mixture, preferably to a temperature of about 40° C. or less, and concentrate the reaction mixture by vacuum distillation. The process described in the '009 publication utilizes Lawesson's reagent in THF with no quench. The inventors have been the first to recognize that these modifications to the reaction conditions render the byproducts from Lewesson's reagent soluble in the reaction medium (toluene), and accordingly, the desired product sulfanyl compound can be crystallized from the concentrated reaction medium, providing the product in a form suitable for use in Step 1b without further purification. Accordingly, the inventive reaction conditions permit the product to be isolated in a suitably pure form without the use of a chromatography step taught in the '009 publication.

In some embodiments, the process of the invention, in Step 1b, utilizes an electrophilic alkylating agent, preferably an alkyl halide, in the presence of a strong base, preferably a metal alkoxide, to convert the sulfanyl compound produced in Step 1a to the corresponding alkylsulfuryl compound (A2). This is depicted schematically in Scheme IIb, Step Ib as treatment with sodium alkoxide and electrophilic alkylating reagent $XR^{48}$. To carry out this step, it will be appreciated that any metal alkoxide which will abstract the proton from the nitrogen of the thioacetamide group of Formula A1a, present in the sulfanyl compound can be employed,

Formula A1a initiating reaction between the sulfur atom of the thioacetamide group and the alkylating reagent. Suitable metal alkoxides include any that are prepared from alcohols containing 6 carbon atoms or less, for example sodium, lithium, and potassium alkoxides, more preferably the alkoxides of alcohol compounds having 5 carbon atoms or less, and more preferably, sodium ethoxide. Preferably, when a metal alkoxide is employed, an alkoxide is selected having an alkoxy-substituent such that, if it should undergo exchange with $R^{2a}$ during the reaction, mixed ester products will not be produced.

In the electrophilic alkylating reagent $R^{48}X$, $R^{48}$ comprises an alkyl moiety, preferably an alkyl moiety having 6 carbon atoms or less, more preferably —$CH_3$. The "X" portion of the $R^{48}$ alkylating group comprises a good leaving group, for example a halide, for example iodine, a sulfanyl, and a sulfate. Preferably the electrophilic alkylating reagent is methyl iodide.

As mentioned above, the '009 publication teaches using a Meerwein's Salt alkylating reagent, for example ($Me_3O^-$ $BF_4^+$), to provide an alkyl-sulfanyl-quinolinyl intermediate compound from the carbo-thioyl intermediate compound. As is known, Meerwein's Salts are highly unstable reagents and not available commercially in quantities suitable for commercial scale preparation of intermediate compounds.

The inventors have been the first to recognize that substituting an alkoxide base and an alkylating reagent for the Meerwein salt alkylating agent eliminates from the alkylating step reactive and difficult to handle Meerwein salts. Moreover elimination of the Meerwein salt in accordance with the present invention provides a solid intermediate instead of the unstable oil intermediate yielded in the reaction following the Meerwein salt route. Additionally, the product contains a cleaner mix of isomers permitting isolation of the desired product purity and ee purity without the need for column separation necessitated by the Meerwin salt route. Accordingly, this change improves the scalablity of this step to a scale of a size suitable for the provision of commercial quantities of the intermediate (multiple Kg quantity of product) using ordinary production equipment.

Step 2—Oxazoline Ring Formation (Compounds of Formula A3)

As mentioned above, oxazoline ring formation in the intermediate compound from which compounds of Formula I are synthesized is a critical step in the provision of the compounds of Formula I. The oxazoline ring formation in accordance with the present invention process is shown below in the scheme labeled Step 2.

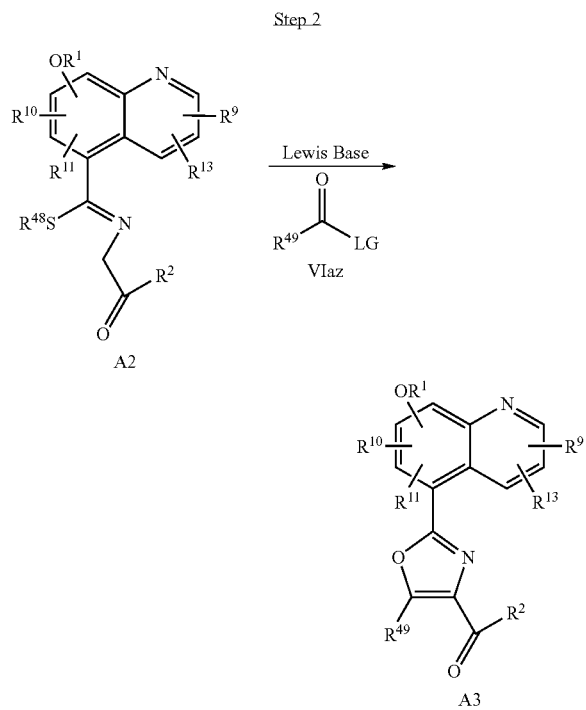

As mentioned above, the '009 publication teaches the formation of an oxazoline ring by a process utilizing an acid fluoride derivative of protected serine acid, which is itself prepared from toxic, unstable cyuranic fluoride. With reference to the portion of the process of the present invention presented above schematically as Step 2, the inventors have been the first to recognize that formation of the oxazoline ring can be carried out under milder conditions than are available in the acid fluoride route described in the '009 publication. Accordingly, in some embodiments the process of the present invention utilizes more easily prepared acylating reagents (described in detail below) in the presence of a Lewis base. For the purposes of the present invention, a Lewis base is defined as a base having an electron pair having sufficient base strength to abstract a proton from acetyl carbon in the methylene-amino acetyl functional region of the compound of Formula A2, which carbon is pointed out in Scheme IIc below.

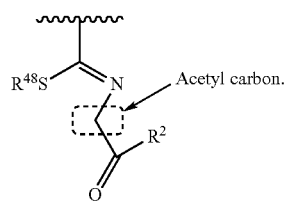

Scheme IIc

In carrying out Step 2 in accordance with the present invention, suitable Lewis bases are preferably selected from metal amides, for example, lithium diisopropyl amide (LDA) and sodium bis(trimethylsilyl)amide (NaHMDS (HexaMethylDiSilizane)). Other Lewis bases which can be employed include metal alkoxide bases, for example, sodium alkoxide, for example sodium methoxide and lithium alkoxide, for example, lithium t-butoxide, each of which can be prepared by contacting the corresponding anhydrous alcohol to the metal under inert atmospheric conditions. Other Lewis bases which can be employed include metal alkyls, for example, lithium alkyl, for example, butyl lithium, the preparation of which is known. It will be appreciated that other members of these classes of compounds can be employed as well as other bases know to have sufficient proton affinity. In some embodiments of the present invention, preferably hindered Lewis bases are employed, for example, lithium diisopropyl amide and sodium hexamethyldisilizane (NaH DS), which is also known as sodium bis(trimethylsilyl)amide. The preparation of these amides is known, and each is available commercially as an article of commerce. One method of preparation of sodium amide bases in commercial scale quantities is treatment of a solution of the corresponding secondary amine with an excess of sodium metal.

In some embodiments, the oxazoline-ring formation aspect of the present invention is carried out also using an acylating agent (compound of Formula VIaz, Step 2, above) selected from acid anhydrides, esters, acyl carbonates, and amides. The inventors have surprisingly found that these intermediates lead to high yields of the oxazoline product under milder conditions than can be employed using the acid fluoride taught in the above-mentioned '009 publication. In some embodiments of the present invention, it is preferred to carry out Step 2 wherein the "LG" portion of the acylating reagent (leaving group) preferably comprises an acid anhydride (—O—C(O)-alkyl) structure (wherein the "alkyl" portion of the structure may be substituted with an electron withdrawing group, for example, a halogen, an ester (—O-alkyl and —O-aryl) structure wherein the "alkyl" and "aryl" portions of the structure may be substituted as described above in the general definitions portion of the detailed description) and an amide (N-alkyl, N-benzyl, and N-aryl) structure (wherein the "alkyl", "benzyl" and "aryl" portions of the structure may be substituted as described above in the general definitions portion of the detailed description). It will be appreciated that other leaving groups suitable for nucleophilic displacement can also be employed. In some embodiments, when the LG portion of the structure comprises a second acyl carbon, for example, where the acylating reagent is an acid anhydride, it is preferred to select substituents which are stearically bulky to prevent attack on the LG acyl group. For example, with reference to the compound of Formula VIaz in Step 2, above, in some embodiments where an acid anhydride acylating reagent is employed, for example, wherein $R^{49}$ is

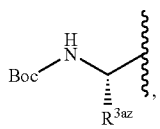

and $R^{3az}$ is hydrogen or a tertiary butoxy substituent, preferably LG is

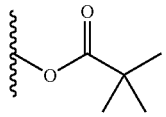

(a stearically bulky group), thus promoting nucleophilic attack on the acyl carbon of the acylating reagent by preventing facile attack on the acyl carbon of the t-butoxy substituent.

In some embodiments, alternatively to, or in addition to selecting bulky substituents on the acylating reagent, deactivating heteroatoms can be selected to protect the acyl group of anhydride leaving groups from attack, for example, the alkylestercarbonicacid anhydride of Formula IIIs (above), which deactivates the leaving group acyl carbon to nucleophilic attack. In some embodiments, alternatively, or in addition, the acyl carbon atom of the acylating reagent can be activated toward nucleophilic attack, for example, activated esters, for example, esters having the structure of the compound of Formula IIIr, above, and N-alkoxyamide compounds of the structure of Formula IIIq, above, activate the acyl carbon of the acylating reagent to nucleophilic attack. In some embodiments, preferably the acylating reagent leaving group is the compound having the structure of Formula IIIa1 (above), where $R^{46}$ is a t-butyl group.

In some embodiments of the present invention, the $R^{49}$ portion of the acylating reagent preferably comprises a structure selected from the Structure of Formula IIIa,

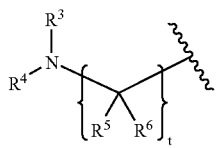

Formula IIIa wherein $R^3$, $R^4$, $R^5$, $R^6$ and "t" are as defined herein, and the structure of Formula IIIb,

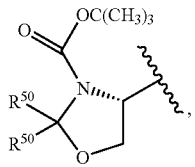

Formula IIIb wherein each of $R^{50}$ is a linear, branched, or cyclic alkyl each selected independently, or both of $R^{50}$ are taken together to form a cycloalkylspirocycle. In some embodiments utilizing an $R^{49}$ substituent of the compound of Formula IIIb, preferably each $R^{50}$ is selected to be a methyl ($H_3C$—) group.

In some embodiments where the $R^{49}$ portion of the acylating reagent has the structure of Formula IIIa, preferably, $R^3$, $R^4$, $R^5$, $R^6$ and "t" are selected to give a structure of Formula IIIc or IIIcz.

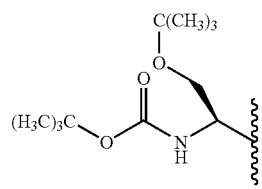

Formula IIIc

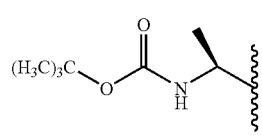

Formula IIIcz

It will be appreciated that other structures, for example differently substituted amino structures providing other compounds of Formula I, as defined herein and in the '009 publication, may alternatively be employed in place of the structures defined for $R^{49}$ above.

Preferably, $R^1$, $R^9$, $R^{10}$, $R^{11}$, and $R^{13}$ are selected to provide a quinoline portion of the VIII intermediate having the structure of 8-Methoxy-2-trifluoromethyl-quinoline, Formula VIIIa

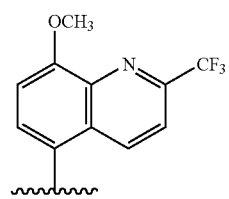

Formula VIIIa

Preparation of Acylating Reagents

Suitable acylating reagents wherein "LG" is an acid anhydride may be prepared, for example, from a salt of the corresponding acid. Accordingly, acid anhydrides can be prepared by treating the corresponding acid with a mild base, for example, potassium carbonate and ammonium dicyclohexyl amine (DCHA) to form the corresponding salt, which is then treated with an acid chloride, for example, as shown below in Scheme VII

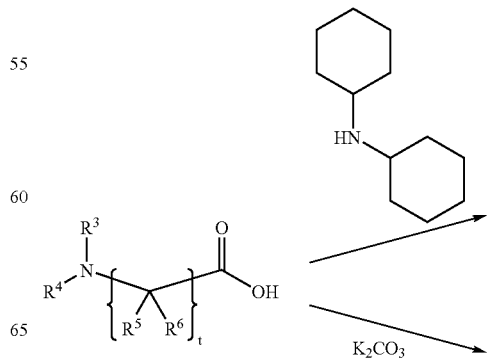

Scheme VII

-continued

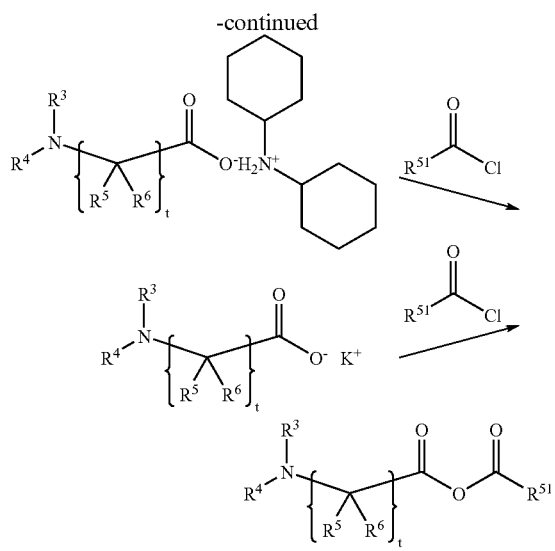

wherein $R^{51}$ is $-O-R^{46}$ as defined above or a linear, branched or cyclic alkyl, optionally substituted, and $R^3$, $R^4$, $R^5$, and $R^6$ are as defined herein. It will be appreciated that the oxazoline ring formation reaction of the present invention can be carried out utilizing any suitable acid anhydride provided by any means and still be within the scope of the present invention process.

In some embodiments of the present invention, preferably $R^{51}$ is a t-butyl group ($(CH_3)_3C-$), preferably "t"=1, preferably one of $R^5$ and $R^6$ is hydrogen and the other is a t-butoxy group ($(CH_3)_3C-O-$), preferably one of $R^3$ and $R^4$ is hydrogen and the other is selected from t-butoxy carbonyl group ($(CH_3)_3C-O-C(O)-$) and H, to give respectively, acylating reagents having the structure of Formulae VIIa and VIIaz.

Formula VIIa

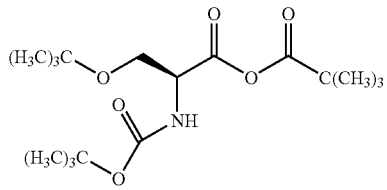

Formula VIIaz

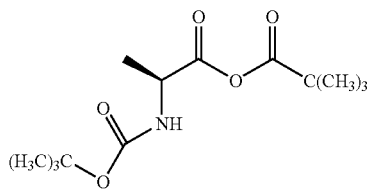

Acylating reagents for use in the present invention wherein "LG" is an ester can be prepared, for example, from the corresponding acid anhydride by treatment with an alcohol in the presence of a base suitable to deprotonate the alcohol, for example, 4-dimethyl aminopyridine (DMAP) in accordance with Scheme VIIb.

Scheme VIIb

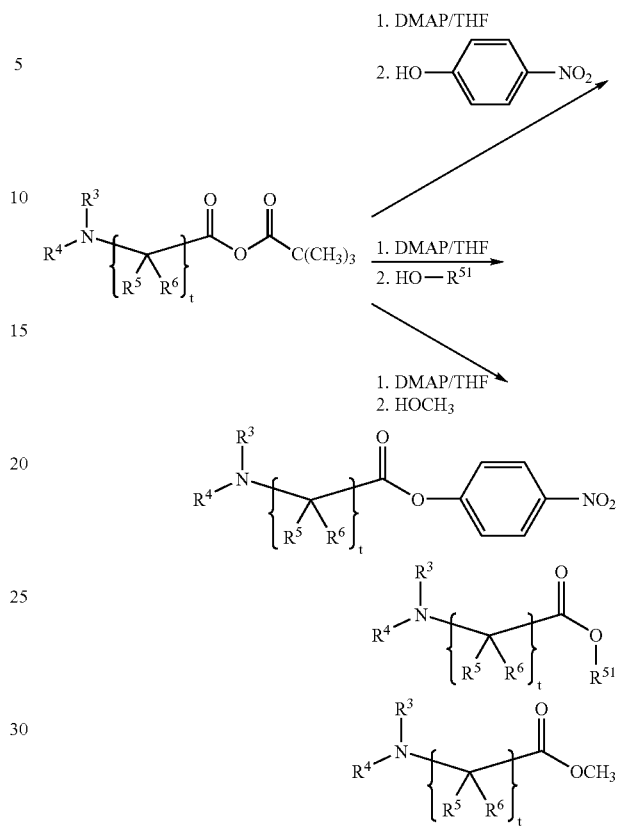

wherein $R^3$, $R^4$, $R^5$, $R^6$, and $R^{51}$ are as defined above.

Suitable acylating reagents wherein "LG" is an N-alkoxy amide can be prepared, for example, from the corresponding anhydride by treating the anhydride with a suitable N-alkoxy amine or N-alkoxy ammonium salt in the presence of a base in accordance with Scheme VII c, below.

VIIc

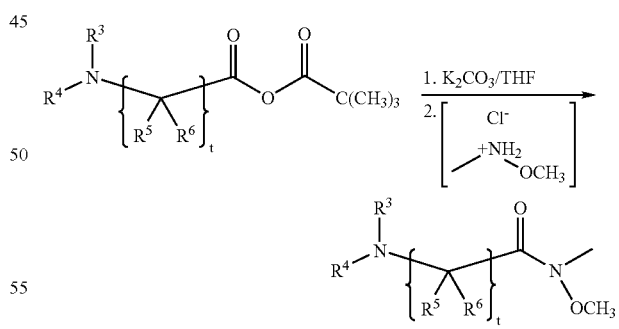

In general, suitable ammonium salts are commercially available or their preparation is known.

With reference to Scheme VII, in some embodiments of the present invention, preferably "t"=1, preferably one of $R^5$ and $R^6$ is hydrogen and the other is a t-butoxy substituent ($(CH_3)_3C-O-$), and preferably one of $R^3$ and $R^4$ is hydrogen and the other is a t-butoxy carbonyl substituent ($(CH_3)_3C-O-C(O)-$), yielding an acylating reagent having the structure of Formula VIIc.

Formula VIIc

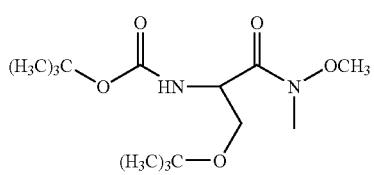

It will be appreciated that in accordance with the foregoing description, starting materials representing other combinations of variables can be selected to provide the corresponding acylating reagent and still be within the scope of the present invention.

Surprisingly, when the oxazoline ring is formed in accordance with the foregoing, the reaction provides an oxazoline-substituted quinolyl intermediate (A3) with a cleaner mix of isomers, a yield of at least about 79% based on the starting sulfanyl intermediate (A2), and in high enantiomer excess than is available from the oxazoline ring-forming process described in the '009 publication. It will be appreciated that the oxazoline ring-forming reaction of the present invention can be used in place of the oxazoline ring-forming process described in the '009 publication without further modification of the steps described therein to provide an improved method of preparing compounds of Formula I, or it may be used in conjunction with one or more other improvements described herein to provide an improved method of preparing the compounds of Formula I.

Step 3—Amidation

In some embodiments of the present invention, after oxazoline ring formation, the resulting product is converted to the corresponding amide through the intermediate anhydride (for example, $R^{2a}$ is an acyl group), ester (for example, $R^{2a}$ is an alkyl group), or acid ($R^{2a}$ is hydrogen) in accordance with Scheme IId, below,

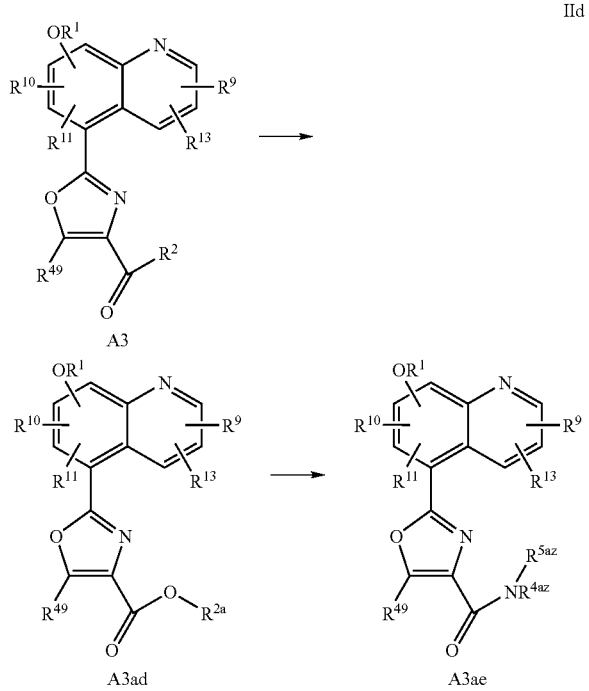

wherein the amide produced is either a secondary amide (thus $R^{4az}$ is hydrogen and $R^{5az}$ is a hydrocarbon moiety as defined herein) or a tertiary amine, for example, a heterocycle (wherein $R^{4az}$ forms a ring with $R^{5az}$). In this manner the reaction can be run as a "one-pot" synthesis without the need for intermediate isolation of the acid. With reference to Reaction Scheme II, above, further details of Step 3 are described next, as illustrated in Schemes IIee and IIef.

Scheme IIee, Step 3-Secondary Amidation

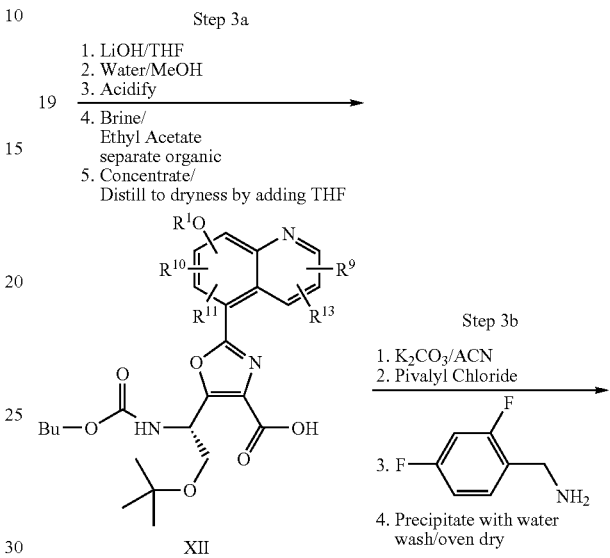

With reference to Scheme VII, intermediate 19 (Scheme III, step 3, above) is converted to the corresponding amide by means of first removing the ethyl ester protecting group to form the corresponding acid (XII), which is then converted to the anhydride intermediate through the intermediate potassium salt of the acid by treatment of the salt with pivalyl chloride. Treatment of the pivalyl anhydride with a primary amine, for example, 2,4 difluorobenzyl amine in Step 3b provides the corresponding secondary amide. The inventors have been the first to recognize that the process of converting first to the acid, then to the anhydride, and finally to the amide permits a secondary amidation reaction to be carried out as a one-pot reaction. The inventors are also the first to recognize that by selecting to proceed through the acid salt in a mixed THF/Acetonitrile solvent, the resulting amide product is provided as a crystalline solid in a form suitably pure that chromatographic isolation and/or further purification of the product is unnecessary. Moreover, the method of the present invention surprisingly permits the amidation reaction in some embodiments of the present invention to be carried out without the need for an amide coupling reagent, for example, HATU, CDI, EDC, DCC, PyBOP, polymer supported CDI, polymer supported EDC and the like, as they are defined in the general definition portion of the detailed description and described in the above-mentioned '009 publication.

Accordingly, in step 3 the oxazoline-substituted quinolinyl ethyl ester intermediate (19) is treated with a base (LiOH) and then acidified to liberate the corresponding acid compound of Formula XII, which is then isolated as an organic solution. The acid compound of Formula XII is converted to a salt by treatment of the solution containing it with potassium bicarbonate. The salt is treated in situ with pivalyl chloride to provide the corresponding acid anhydride. Amidation is then carried out by treating the anhydride with a primary amine to provide a compound of Formula X. Preferably, Preferably, $R^1$, $R^9$, $R^{10}$, $R^{11}$, and $R^{13}$ are selected to provide a quinoline portion of the X intermediate having the structure of 8-Methoxy-2-trifluoromethyl-quinoline, the structure of Formula XIa, discussed above.

Scheme IIef, Step 3-Tertiary Amidation

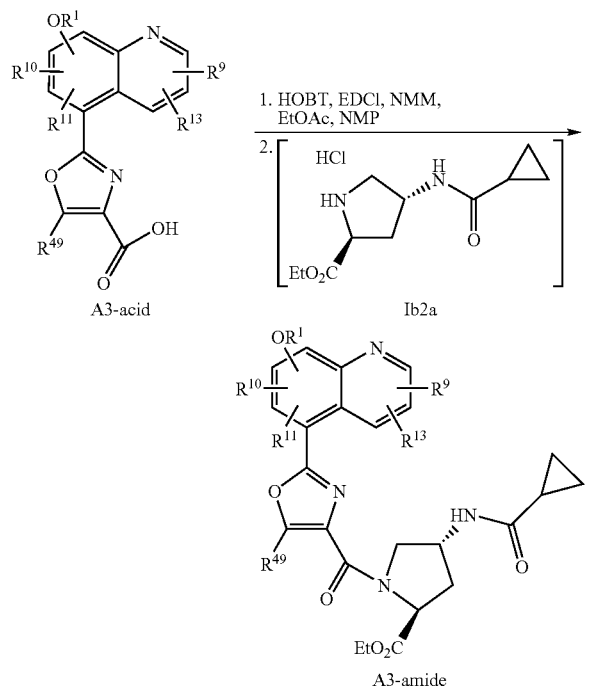

With reference to Scheme IIIef, a tertiary amide can be prepared directly from the acid using an amide coupling reagent comprising HOBT and EDCl in the presence of N-methyl morpholine by reacting the acid form of the oxazoline (A3-acid) with a secondary amine salt, for example, the hydrochloride salt of the cyclic secondary amine compound of Formula Ib2a. Although Scheme IIIef illustrates the reaction using the secondary amine of Formula Ib2a, it will be appreciated that other amines can also be used, for example, those shown in the '062 publication mentioned above, for example, in columns 122 to 288.

The inventors have been the first to recognize that a cleaner tertiary amide product is provided by utilizing the acid (A3-acid) directly in the amidization reaction and employing the amine salt in conjunction with a coupling reagent. In some embodiments of the invention it is preferred to employ a mixed solvent in which to carry out the reaction, preferably ethylacetate and N-methylpyrrolidine.

For use in the tertiary amidation reaction shown in Scheme IIef, in some embodiments it is preferred to supply the amine salt used in the amidation reaction, for example, the proline salt of Formula Ib2a, by direct treatment of a solution containing the amine, or by treatment of a solution containing a protected form of the amine, with an acid to precipitate the salt, which is then isolated for use in the oxazoline-forming reaction described above. Accordingly, in some embodiments of the invention it is preferred to use a protected proline derivative having the structure of the compound of Formula Ib2a2 (wherein, "PG" is an acid labile protecting group), for example, the compound of Formula Ib2a2, dissolved in a suitable solvent, for example, ethyl acetate, and treated with a suitable acid, for example HCl gas, to precipitate the corresponding amine salt, for example, the compound of Formula Ib2a.

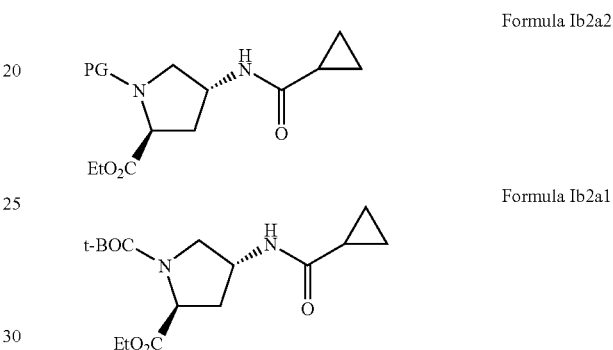

It will be appreciated that any other means of providing a suitable amine salt, including use of alternative acids to form the salt, can be employed to provide an amine salt for use in the reaction described above without departing from the scope of the present invention.

Step 4—Deprotection

With reference to Scheme II above, a compound of Formula I is prepared after amidation by removing any protecting groups present. Thus in accordance with Scheme IIIee-Step 4, and Scheme IIIef-Step 4, below, where R1, R9, R10, R11, R13, and R49 have been selected to provide compounds Xa, Xb, and Ica2, treatment with an acid, for example, trifluoroacetic acid (Xa and Xb) and HCl (Ica2) as shown, provides a compound of Formula I (Xaa and Xab respectively).

Scheme IIIee-Step 4

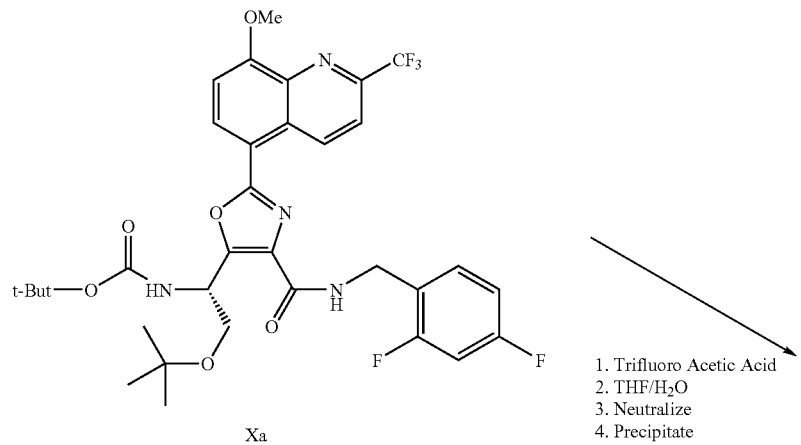

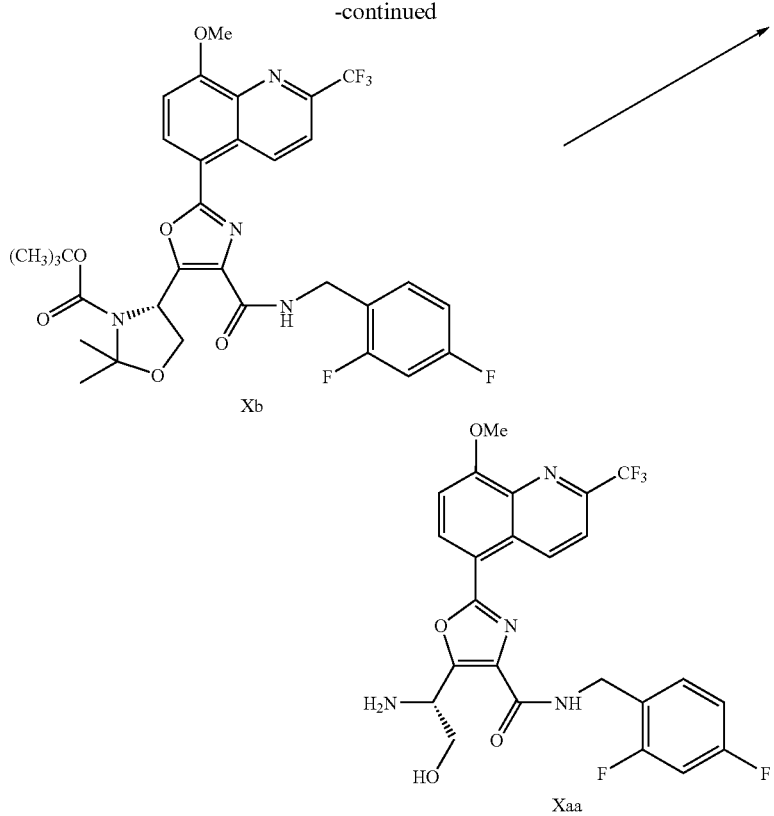
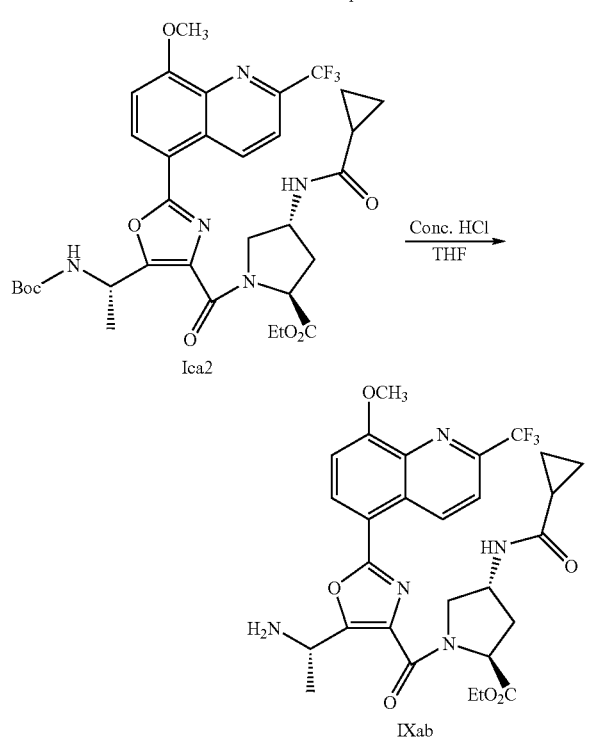
trifluoromethyl-quinolin-5-yl)-oxazole-4-carboxylic acid 2,4-difluoro-benzyl-amide (the Compound of Formula IX) in accordance with Scheme VIII.
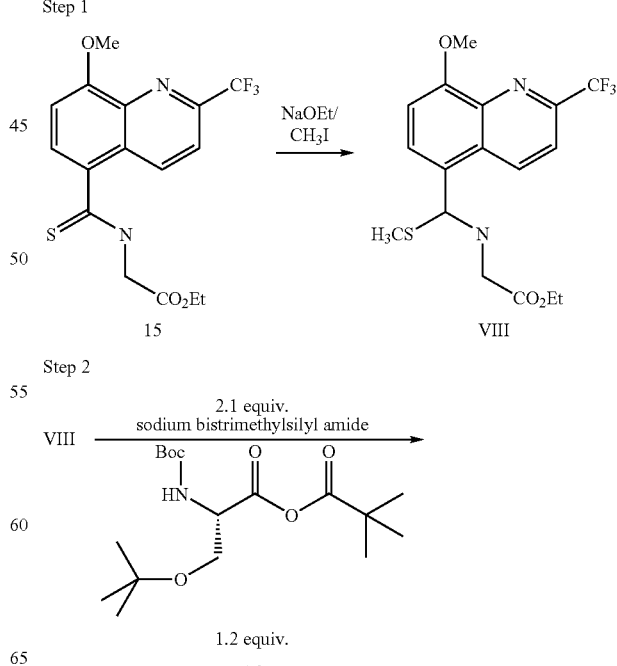
It is believed that various features of the present synthetic scheme can be advantageously combined to provide a synthetic scheme scalable to the preparation of commercial quantities of 5-(1-amino-2-hydroxy-ethyl)-2-(8-methoxy-2-

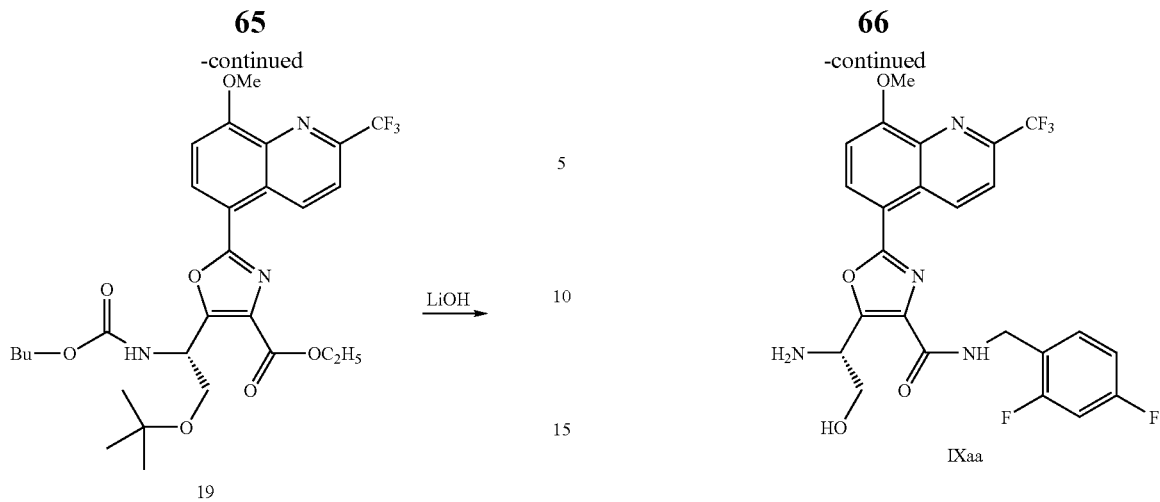

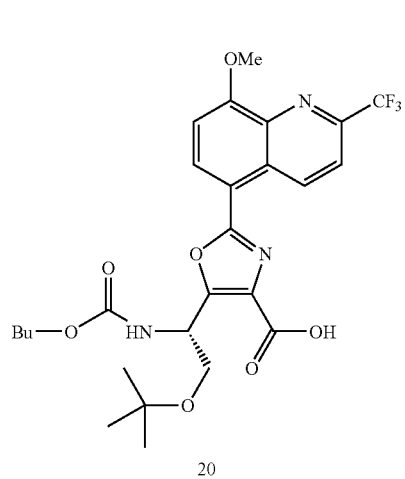

Step 3

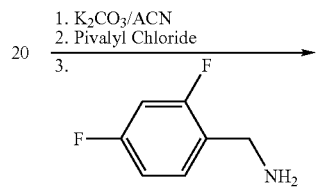

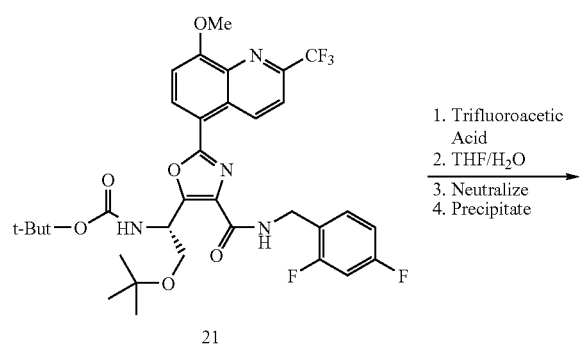

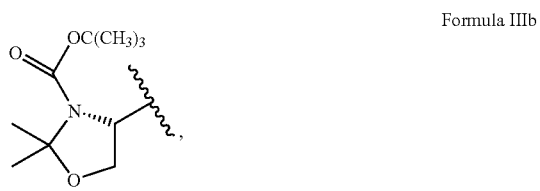

With reference to the details provided above in discussion of steps 1 to 4 in the provision of compounds of Formula I in accordance with the improvements of the invention, the compound of Formula IXaa can be prepared by selecting starting material having a quinolinyl portion in which, with reference to the compound of Formula I, $R^1$ is attached to carbon 8 of the quinoline ring and is methyl, $R^{10}$ and $R^{11}$ are hydrogen, $R^9$ is attached to carbon 2 of the quinoline ring and is trifluoromethyl, and $R^{13}$ is hydrogen. Moreover, when forming the oxazoline ring in step 2, the compound of Formula IX is provided by using an acylation reagent in which, with reference to the discussion of Step II in the detailed description above, the $R^{49}$ portion of the acylating reagent has the structure of Formula IIIc, above, wherein, one of $R^3$ and $R^4$ is t-butoxycarbonyl and the other is hydrogen, one of $R^5$ and $R^6$ is t-butoxy and the other is hydrogen, and "t"=1.

Alternatively, the $R^{49}$ portion can be selected to give the structure of Formula IIIb.

and be utilized in the process in the same manner as shown for the acylating reagent of Formula 16.

In the same manner, the compound of Formula VIII can be prepared and reacted with an acylating reagent of the structure of the compound of Formula Ib1a to give the oxazoline compound having the structure of Formula IBa2-ester, which, after conversion to the corresponding acid, can be amidated and deprotected to give the compound of the structure of Formula IXab, in accordance with steps Alt-2 and Alt-3 of Alternative Scheme VIII shown below.

Alternative Scheme VIII

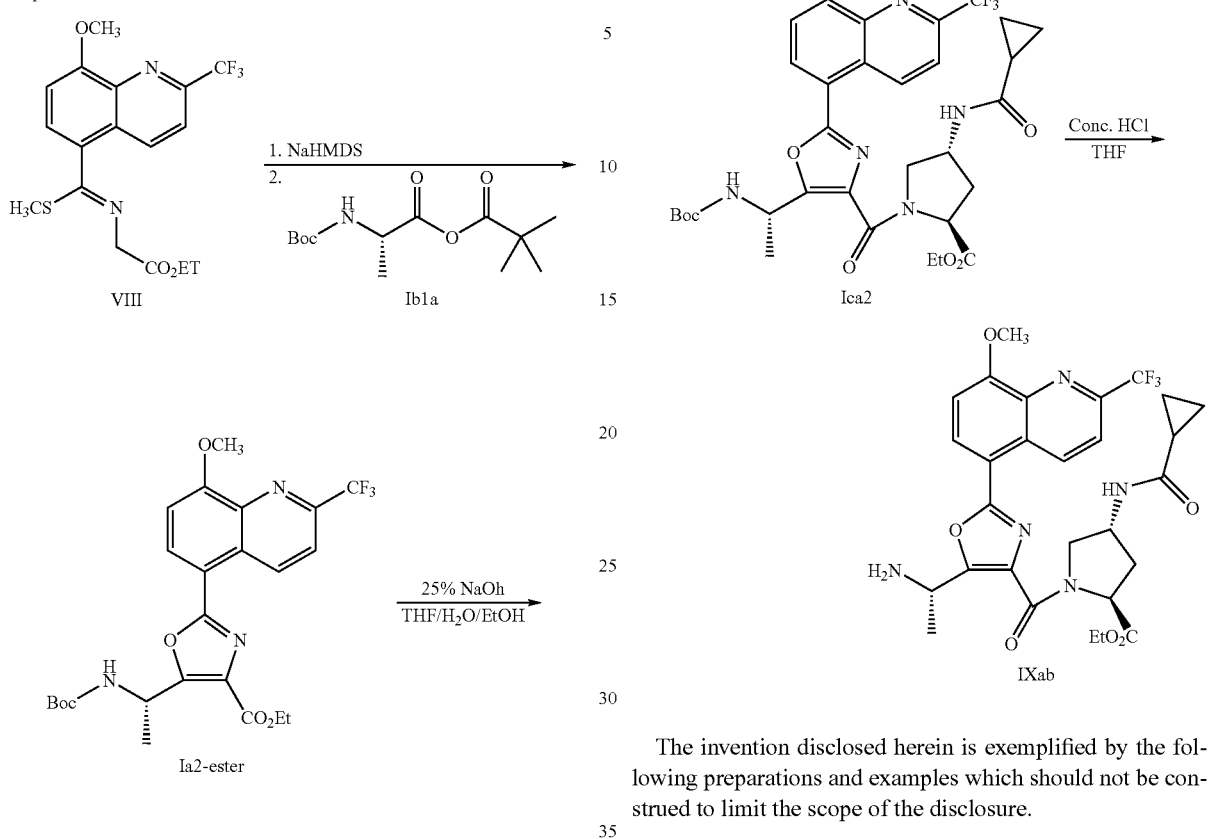

The invention disclosed herein is exemplified by the following preparations and examples which should not be construed to limit the scope of the disclosure.

EXAMPLES

The following solvents and reagents may be referred to by their abbreviations:

acetic acid: HOAc
dichloromethane: DCM
1-[3-(dimethylamino)propyl-3-ethylcarbodiimide monohydrochloride—EDCl
ethanol: EtOH
ethylacetate—EtOAc
1-Hydroxybenzotriazole—HOBT
N-methyl-pyrrolidine—NMP
N-methyl-morpholine—NMM
potassium t-butoxide: t-BuOK
sodium bistrimethylsilylamide: NaHMDS
triethyl amine: TEA
trifluoro acetic acid: TFA
tertiary-butoxycarbonyl: t-BOC
tetrahydrofuran: THF
liter: L
milliliters: mL
grams: g
room temperature or rt (ambient): about 25° C.
mole: mol.

Step Alt-3

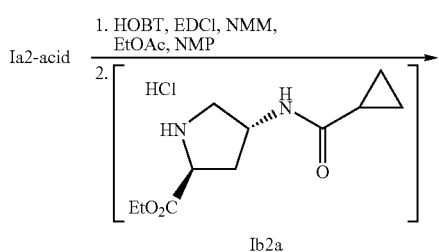

Example 1

Preparation of 5-(2-tert-Butoxy-1-tert-butoxycarbonylamino-ethyl)-2-(8-methoxy-2-trifluoromethyl-quinolin-5-yl)-oxazole-4-carboxylic acid ethyl ester [Compound 19] by treatment of [{(8-Methoxy-2-trifluoromethyl-quinolin-5-yl)-methylsulfanyl-methylene]-amino}-acetic acid ethyl ester [Compound VIII] with 3-tert-Butoxy-2-tert-butoxycarbonylamino-propionic acid 4-[(2,2 dimethyl)pronionic acid]anhydride [Compound 16]

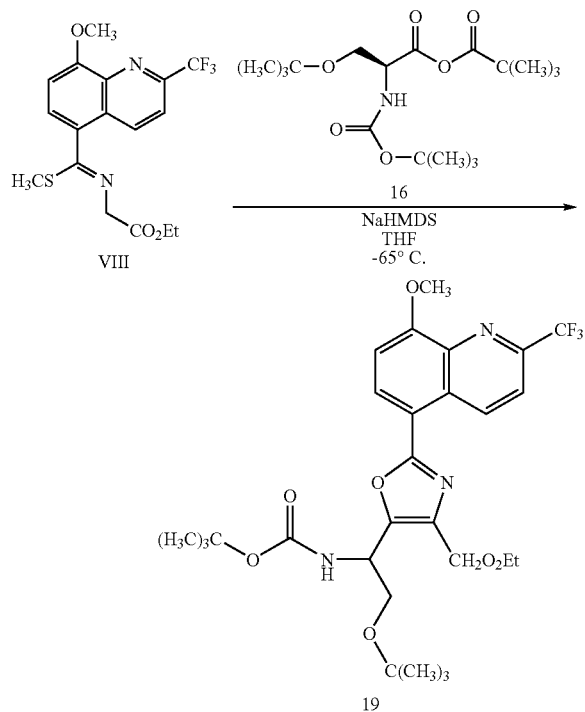

Into a 200 gallon glass lined reactor equipped with a thermocouple, $N_2$ inlet and feed tank was placed 16.5 kg (1.0×) of the compound Formula VIII under a nitrogen purge. Into the reaction vessel, with continued $N_2$ purge, was added 217 liters (13×) tetrahydrofuran (THF, dried, as determined by Karl Fischer titration, to residual water content of <0.05%). The THF was maintained at a temperature of from about 20° C. to about 25° C. until all of the compound of Formula VIII was dissolved. After the compound of Formula VIII had dissolved, the solution was allowed to evaporate at 1 atmosphere until the batch volume was concentrated to about 140 liters (8.5×). When the reaction mixture had reached the desired concentration the temperature of the reaction mixture was reduced and maintained in the range of from about −60° C. to about −70° C. After the reaction mixture had equilibrated in the desired temperature range, the reaction vessel was charged with an aliquot of NaHMDS (as a 2M solution in THF equal to 4.85 kg of NaHMDS, 0.292×) over about 15 minutes. While maintaining the reaction mixture within a temperature range of from about −60° C. to about −70° C. the reaction vessel was charged over about 15 minutes with a solution aliquot of the compound Formula 16 in THF (equal to 2.06 kg of the compound of Formula 16, 0.125×), maintaining the reaction mixture at a temperature of from about −60° C. to about −70° C. After addition of the entire aliquot of the compound of Formula 16, the reaction mixture was agitated for 10 minutes while maintaining the temperature in a range of from about −60° C. to about −70° C.

The sequence of the addition of an aliquot of NaHMDS followed by the addition of a solution aliquot of the compound of Formula 16 and a period of agitation was repeated eight additional times using 0.125 equivalent of the compound of Formula 16 and 0.292 eq. of NaHMDS in each cycle (nine cycles in total). At the end of 9 cycles 92% of the compound of Formula VIII had been converted to a compound of Formula 16 based on HPLC analysis.

At the end of the reaction period the reaction mixture was transferred over a period of about 15 minutes to a vessel containing an aqueous solution consisting of 23.1 kg (1.4×) $KH_2PO_4$ dissolved in 140 liters (8.5×) $H_2O$. During the transfer the reaction mixture was maintained at a temperature below 30° C. To the combined reaction mixture and potassium dihydrogen phosphate solution was added 62 liters (4.3×) ethyl acetate. The mixture was agitated for about 15 minutes and the layers permitted to settle. The layers were separated and the aqueous layer was extracted with 62 liters (4.7×) ethylacetate. The extract was combined with the organic layer and washed with two aliquots of 93 liters (5.6×) 10% aqueous w/v NaCl. The washed combined organic layers were concentrated at 1 atmosphere to a batch volume of 99 liters. Isopropanol, 198 liters, was added into the washed organic layer and the mixture concentrated at 1 atmosphere to a volume of about 149 liters. Heptane, 198 liters (12.0×), was added to the concentrated mixture with the temperature of the mixture maintained at a temperature of between 65° C. and 75° C. After all of the heptane was added the temperature of the mixture was adjusted to and maintained at a temperature between 60° C. and 65° C. and agitated for about 30 minutes. At the end of 30 minutes, with continued agitation the temperature of the mixture was adjusted to a temperature between −5° C. and 5° C., over a 3 hour period, causing solids to form. When the mixture had attained the end temperature range it was agitated for an additional 30 minutes, then the solids were collected by filtration. The filter cake thus prepared was washed with 33% v/v ethylacetate in heptane and dried in a vacuum oven for 12 hours maintained at a temperature of from about 55° C. to about 65° C. Yield 79% based on amount of Compound VIII initially employed, ee purity >99%.

The solids thus obtained were analyzed by proton NMR ($^1$HNMR in CDCl$_3$) with the following results (chemical shift relative to TMS, multiplicity).

9.89 (1H, d); 8.56 (1H, d); 7.94 (1H, d); 7.22 (1H, d); 5.91 (1H, s, b); 5.58 (1H, s, b); 4.47 (2H, q); 4.43 (3H, s); 3.75 (2H, t); 1.47 (9H, s); 1.19 (9H, s).

Preparation of 3-tert-Butoxy-2-tert-butoxycarbonylamino-propionic acid 4-(2,2 dimethyl)propionic acid anhydride [Compound 16]

For use in the examples, Compound 16 was prepared in accordance with the following procedure.

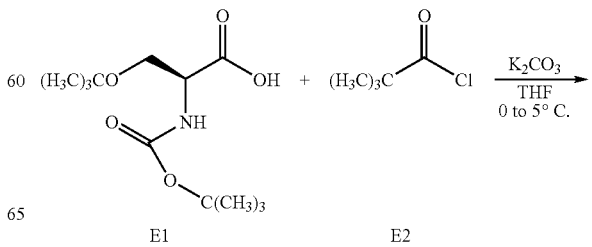

-continued

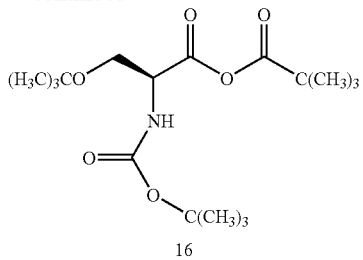

16

-continued

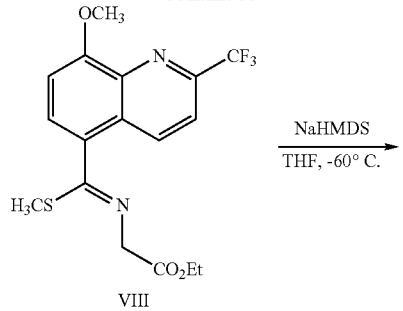

VIII

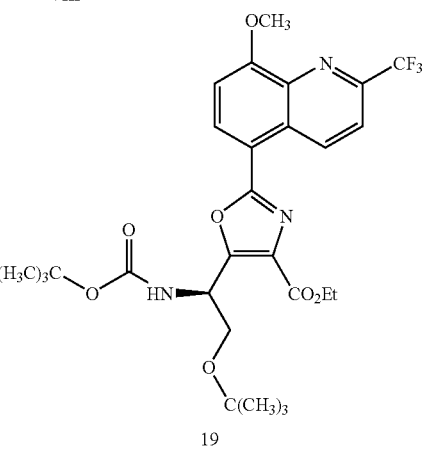

19

Under a nitrogen purge, a 500 ml 3 neck round bottom flask equipped with a thermometer, N₂ inlet and addition funnel was charged with 20.5 g (1.0×, 78.45 mmol) of 3-tert-Butoxy-2-tert-butoxycarbonylamino-propionic acid (the compound Formula E1) in 250 ml (10×) dry THF. To the reaction flask was added 23 g (1.1×166.7 mmol, 325 mesh) K₂CO₃. The temperature of the reaction mixture was adjusted to a temperature between 0° C. and 5° C. Into the cold reaction mixture, with agitation, was added 9.27 g (0.45×, 76.88 mmol) of 2,2-Dimethyl-propionyl chloride (the compound Formula E2) over a period of about 15 minutes while maintaining the reaction mixture at a temperature between 0° C. and 5° C. After all of the compound of formula E2 was added, agitation was continued for about 2 hours while maintaining the reaction mixture at a temperature between 0° C. and 5° C. The reaction was monitored by ¹HNMR until it indicated that no more starting material remained. At the end of the reaction period, 4.0 g (0.2×) celite was added to the reaction mixture and the reaction mixture was filtered through a filter line charged with 1.0 g (0.1×) of additional celite. The collected filter cake was washed with one 50 ml aliquot (2.4×) of dry THF. The collected filtrate and wash were combined and concentrated under vacuum to about 40 ml (2 X). Additional aliquots of dry THF were added and vacuum distillation was carried out on the concentrated filtrate until the water content of the filtrate (determined by Karl Fischer titration) indicated a water content of less than about 0.07%. The resultant anhydride (compound 16) concentrated THF solution is used as obtained.

Example 2

Preparation of Compound (19) by Treatment of Compound (VIII) with 2-tert-Butoxy-1-(methoxy-methyl-carbamoyl)-ethyl]-carbamic acid tert-butyl ester [Compound E3]

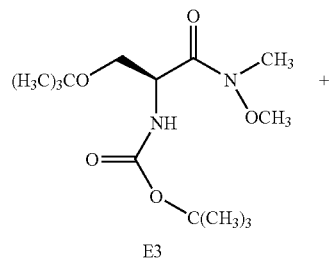

E3

Into a 250 ml 3 neck round bottom flask equipped with a thermometer, N₂ inlet and two addition funnels was added, under nitrogen purge, 5.0 g (1.0×, 12.9 mmole) of the compound Formula VIII. Dry tetrahydrofuran (THF), 25 mls (5×), with the temperature maintained at 20° C. to 30° C. was added to the flask to dissolve the compound Formula VIII. After all of the compound of Formula VIII was dissolved, the temperature of the reaction mixture was adjusted to a temperature between −80° C. and −70° C. To the reaction flask was added NaHMDS (2M in THF, 1.6 ml, 0.32×, 3.23 mmol) under nitrogen purge over a period of about 15 minutes with the temperature of the reaction mixture maintained at a temperature between −60° C. and −70° C. When all of the NaHMDS solution had been added the reaction mixture was agitated with the temperature maintained between −70° C. and −60° C. for a period of 10 minutes. At the end of the initial agitation period a solution of the compound Formula E3 in THF (0.61 g of E3, 0.12×, 2.0 mmol) was added to the reaction mixture under nitrogen purge over 15 minutes with the temperature of the reaction mixture maintained at a temperature between −60° C. and −70° C. After addition of the solution of the compound of Formula E3, the reaction mixture was agitated while maintaining it at a temperature of from about −70° C. to about −60° C. for a period of 10 minutes. The procedure of adding a solution of NaHMDS, agitating, then adding a solution of the compound of Formula E3 was repeated seven additional times (eight interations of NaHMDS/Formula E3 addition total), at which point ¹HNMR analysis of the reaction mixture indicated that more than 70 mole % of the starting quinoline (Formula VIII) was converted. Two additional aliquots of N MS THF solution to give 0.32 equivalents based on the remaining starting material, followed by the same agitation schedule and addition of the compound of Formula E3 to give 0.12 equivalents, based on the remaining starting material, were added following the same addition/agitation schedule (10 addition/agitation cycles total). At the end of these addition/agitation cycles $^1$HNMR analysis of the reaction mixture indicated that only about 7% of the compound of Formula VIII remained in solution. The compound of Formula 19 was found to have an enantiomeric purity of 97.5% ee.

At the end of the reaction period the reaction mixture was added, over a period of 15 minutes, to 70 ml of a solution comprising 10% aqueous w/v $KH_2PO_4$ at 10° C. with vigorous agitation. After the mixture was stirred for additional 10 minutes at 10° C., 50 mls of ethyl acetate was added. The organic layer was separated in a separation funnel. The organic layer was then washed with 30 ml of 5% aqueous w/v $KH_2PO_4$, followed by $H_2O$. The solution was distilled under atmospheric pressure until it attained a volume of 70 ml. The solution was mixed with 50 ml of isopropanol at 60° C. and the mixture was again distilled under atmospheric pressure to volume of 50 ml. The compound of Formula 19 was crystallize from the concentrated solution by adding 70 ml heptane while maintaining the mixture at a temperature of 60° C. followed by cooling the mixture to a temperature of between 10° C. and 0° C. over a period of 3 hours. Crystals of the product were recovered by filtration. It was found that the isolated material yield was about 63% based upon the amount of starting quinoline used and the product (compound of Formula 19) had an enantiomeric purity of 98.3% ee.

Preparation of 2-tert-Butoxy-1-(methoxy-methyl-carbamoyl)-ethyl]-carbamic acid tert-butyl ester [Compound E3]

For use in Example 2, 2-tert-Butoxy-1-(methoxy-methyl-carbamoyl)-ethyl]-carbamic acid tert-butyl ester (compound E3) was prepared in accordance with the following scheme:

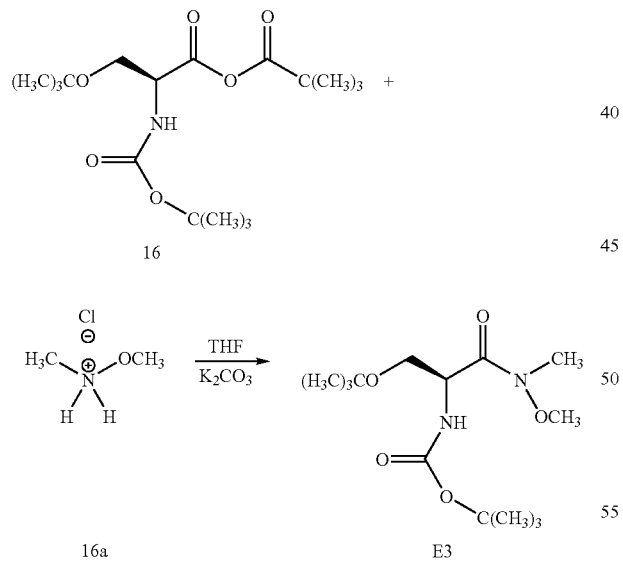

Into a 100 ml 3 neck round bottom flask equipped with a thermometer and an $N_2$ inlet was placed 4.6 g (13.4 mmol) of the compound Formula 16 dissolved in 50 ml anhydrous Methyltertbutylether (MTBE) at ambient temperature (20° C. to 25° C.). Into the reaction mixture was placed 1.4 g (14.7 mmol) of the compound Formula 16a, followed by 3.7 ml (26.4 mmol) of triethylamine. The reaction mixture was agitated for 12 hours at ambient temperature. The solution was then mixed with 30 ml of methyl t-butylether and 40 ml of water. The organic layer was separated and washed with 30 ml of 1N HCl solution followed by 30 ml of water. The solution was concentrated under vacuum to 3.2 g of oil containing 2.87 g active (70.4%) E3. This oil was used in the reaction of Example 2 to prepare the compound of Formula 19.

The oil was also analyzed by proton NMR ($^1$HNMR in $CDCl_3$) with the following results (chemical shift relative to TMS, multiplicity).

5.28 (1H, d); 4.92 (1H, d); 3.87 (3H, s); 3.54 (1H, d); 3.15 (3H, s); 1.23 (9H, s); (1.08 (9H, s)

Example 3

Preparation of Compound [19] by Treatment of Compound [VIII] with 3-tert-Butoxy-2-tert-butoxycarbonylamino-propionic acid 4-nitro-phenyl ester [E4]

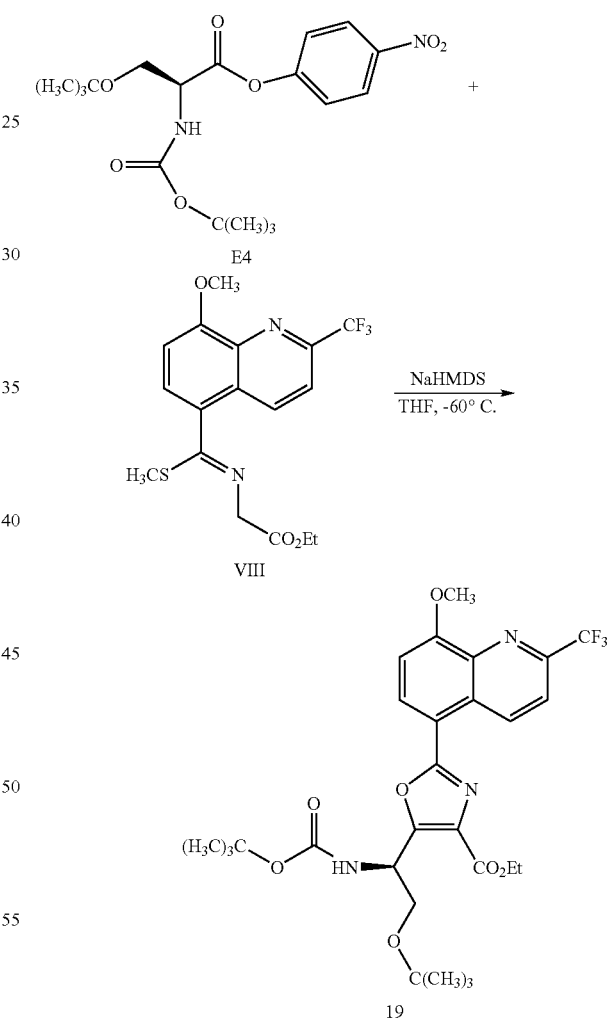

Into a 125 ml 3 neck round bottom flask equipped with a thermometer, $N_2$ inlet and two addition funnels was placed 0.386 g (1.0 mmole) of the compound Formula VIII, and 0.483 g (1.26 mmoles) of the compound Formula E3. To the flask was added 5 mls of dry THF at ambient temperature (20° C. to 30° C.) to dissolve the solids in the flask. The reaction solution was cooled and maintained at a temperature between -70° C. and -80° C. To the reaction mixture was added 2.6 equivalents (based on the compound of Formula VIII) of NaHMDS as a 2M solution in THF (1.3 ml, 2.6 mmol) over a period of 15 minutes while maintaining the reaction mixture between -60° C. and -70° C. The reaction mixture was agitated for 10 minutes while the temperature was maintained between -60° C. and -70° C. Four additional aliquots of NaHMDS (total of 5 additions of NaHMDS) were added with a 10 minute period of agitation following each addition. Each aliquot was calculated to be 2.6 equivalents based upon the remaining amount of the compound of Formula VIII in the reaction mixture, as determined by NMR. After the last addition, NMR determined that 86.6% of the compound of Formula VIII had been converted to the compound of Formula 19. The reaction mixture was transferred over 15 minutes from the reaction flask to a vessel containing 15 ml of 10% wt./vol. $KH_2PO_4$, and was left in contact for a period of 15 minutes. At the end of the period, the layers were separated and the aqueous layer was extracted with ethyl acetate. The organic layers were combined and washed with 10 ml of saturated sodium chloride solution.

Preparation of
3-tert-Butoxy-2-tert-butoxycarbonylamino-propionic
acid 4-nitro-phenyl ester [Compound E4]

Compound E4 was prepared for use in Example 3 in accordance with the following procedure.

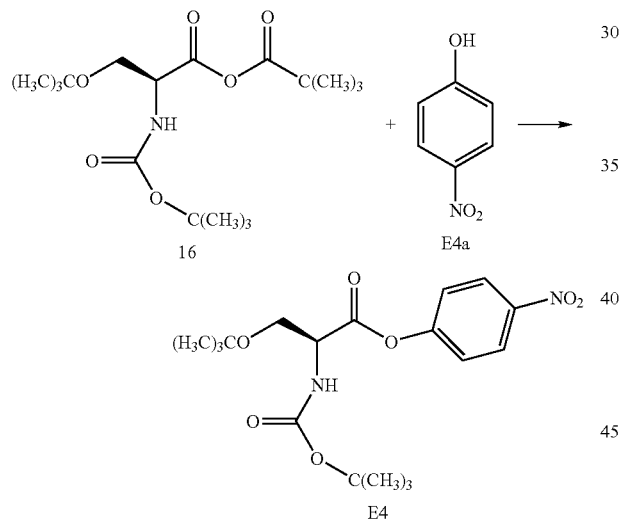

Into a 100 ml 3 neck round bottom flask equipped with a thermometer and an $N_2$ inlet was placed 0.27 g, (0.78 mmol) of the compound Formula 16 dissolved in 2 ml anhydrous THF at ambient temperature (20° C. and 25° C.). Into the reaction solution was placed 0.13 g (0.94 mmol) of the compound Formula E4a, followed by 2.0 g (1.49 mmol) of Dimethylaminopyridine. The reaction mixture was agitated for 2 hours while maintaining it at ambient temperature. Methyl-tertiary butyl ether (MTBE), 20 ml, was added to dissolve the residue. The reaction mixture was washed with 10 ml of a 10% w/v aqueous $K_2CO_3$ solution followed by 10 ml of $H_2O$. The organic layer was separated and concentrated under vacuum to yield 0.25 g of an oil (84% yield) for use in the preparation of Compound 19 in accordance with Example 3.

The oil thus obtained was analyzed by proton NMR ($^1$HNMR in $CDCl_3$) with the following results (chemical shift relative to TMS, multiplicity).

8.23 (2H, d); 7.22 (2H, d); 5.38 (1H, d); 4.61 (1H, d); 3.95 (1H, d); 1.36 (9H, s); 1.15 (9H, s)

Example 4

Preparation of Compound [19] by Treatment of
Compound [VIII] with
3-tert-Butoxy-2-tert-butoxycarbonylamino-propionic
acid methyl ester [Compound E5]

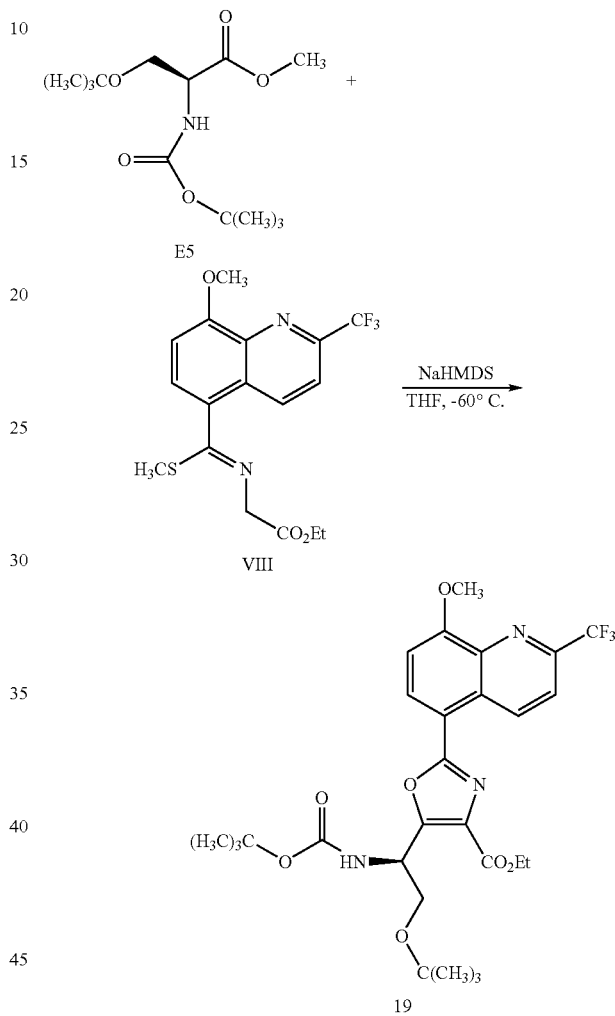

Into a 125 ml 3 neck round bottom flask equipped with a thermometer, $N_2$ inlet and two addition funnels was placed 0.5 g (1.0 eq, 1.29 mmole) of the compound Formula VIII and 0.448 g (1.12 eq, 1.63 mmoles) of the compound Formula E5. To the reaction mixture was added 5 mls (10×) of dry THF at ambient temperature (20° C. to 30° C.). When the solids had dissolved, the reaction mixture was cooled and maintained within a temperature range of -70° C. to -80° C. To the reaction mixture was added 2.6 mM of NaHMDS as a 2M THF solution (1.3 ml, 2.6 eq) over a period of 15 minutes while maintaining the temperature within a range of -60° C. to -70° C. After the addition period the reaction mixture was agitated for 10 minutes. Three additional cycles of adding aliquots of a 2.0 M THF solution of NaHMDS in an amount equal to 2.6 equivalents of the compound of Formula VIII remaining in the reaction mixture followed by a 10 minute period of agitation were continued. At the end of the last agitation period, proton NMR indicated that 10% of the compound of Formula VIII had been converted to product.

Preparation of 3-tert-Butoxy-2-tert-butoxycarbonylamino-propionic acid 4-nitro-phenyl ester [Compound E5]

For use in Example 4, compound E5 was prepared in accordance with the following procedure.

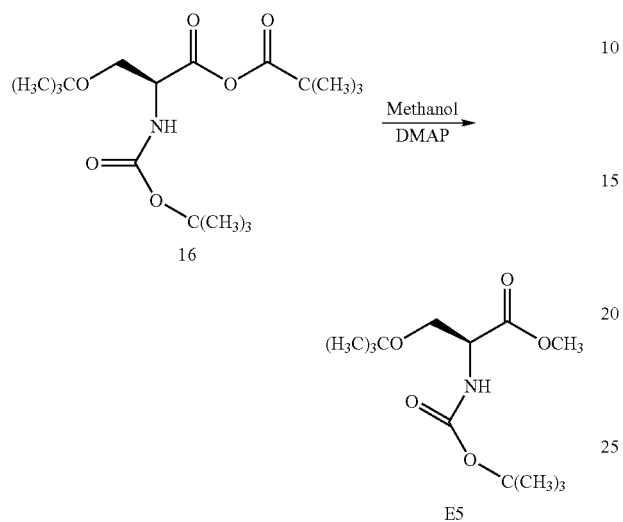

Into a 25 ml round bottom flask equipped with an $N_2$ inlet, at ambient temperature (20° C. to 25° C.) was placed 4.6 g (1.0 eq, 13.4 mmol) of the compound Formula 16, prepared in accordance with Example I, dissolved in 2 ml anhydrous THF. To the reaction vessel was added 2 mg of dimethylaminopyridine (DMAP). The reaction mixture was agitated at ambient temperature for 2 hours. At the end of 2 hours, 20 ml of methyl t-butyl ether (MTBE) was added to the mixture. The resultant solution was washed with 10% w/v aqueous potassium carbonate (30 ml) followed by a water wash. The organic solution was filtered and concentrated under vacuum to provide 2.95 g of an oil which was used directly in the preparation of compound 19 in accordance with Example 4. $^1$H NMR indicates the product is 95% pure (yield of 76%).

Example 5

Preparation of Compound [XVI] by Treatment of Compound [VIII] with 4-tert-Butoxycarbonyloxycarbonyl-2,2-dimethyl-oxazolidine-3-carboxylic acid methyl ester [Compound 19a]

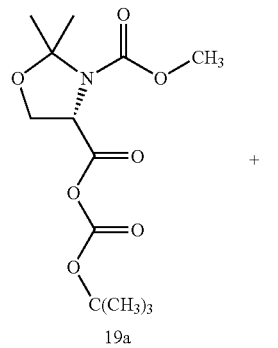

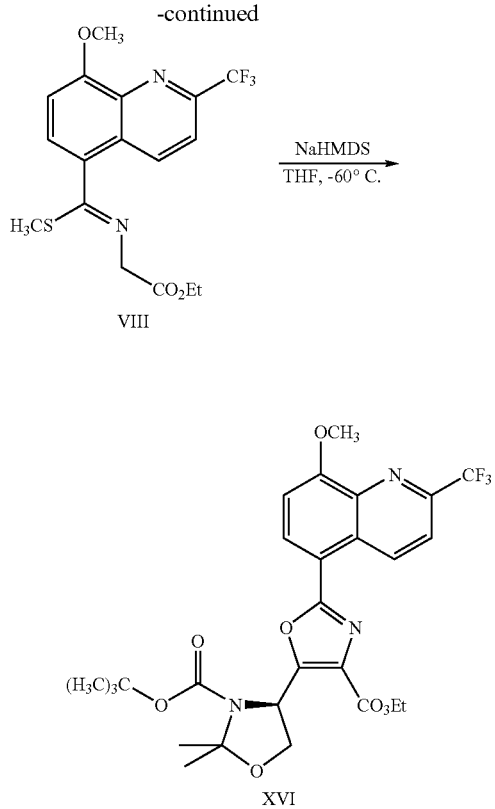

Into a round bottom 3-neck flask fitted with a thermometer, a nitrogen inlet and two addition funnels was placed 4 mls. of dry tetrahydrofuran (THF) and 0.5 g (1.29 mmole) of the compound formula IV, under $N_2$ purge. The THF was warmed to dissolve the solids, then the solution was cooled to and maintained at a temperature between −70° C. and −80° C. At the completion of the third cycle, agitation of the reaction mixture was continued for an additional 20 minutes while maintaining the reaction mixture at a temperature between −60° C. and −70° C. The reaction mixture was quenched with 10 mL of 5 wt % aqueous $KH_2PO_4$ at −60° C. The mixture was warmed to room temperature and agitated for 10 minutes, followed by the addition of 20 ml of ethyl acetate. The aqueous and organic layers were separated, the aqueous layer was extracted with an additional 20 ml aliquot of ethyl acetate and the organic layers were combined. The combined organic layers were washed with an additional 10 ml of water (twice). The organic solvent was stripped and the residue was extracted with two 10 ml aliquots of isopropanol. The isopropanol extract was stripped and the residue redissolved in 4 mls of isopropanol. The compound of Formula XVI (0.177 g, 24% yield based on the amount of the compound of Formula VIII used).

The solids thus obtained were analyzed by proton NMR ($^1$HNMR in $CDCl_3$) with the following results (chemical shift relative to TMS, multiplicity).

9.84 (1H, d); 8.15 (1H, d); 7.79 (1H, d); 7.05 (1H, d); 5.62 and 5.59 (1H, d, rotomers); 4.34 (2H, q); 4.24 (1H, dd); 4.02 (3H, s); 3.92 (1H, dd); 1.30 (3H, t); 1.11 (9H, s).

Preparation of 4-tert-Butoxycarbonyloxycarbonyl-2,2-dimethyl-oxazolidine-3-carboxylic acid methyl ester [Compound 19a]

For use in Example 5, the compound of Formula 19a was prepared in accordance with the following reaction scheme.

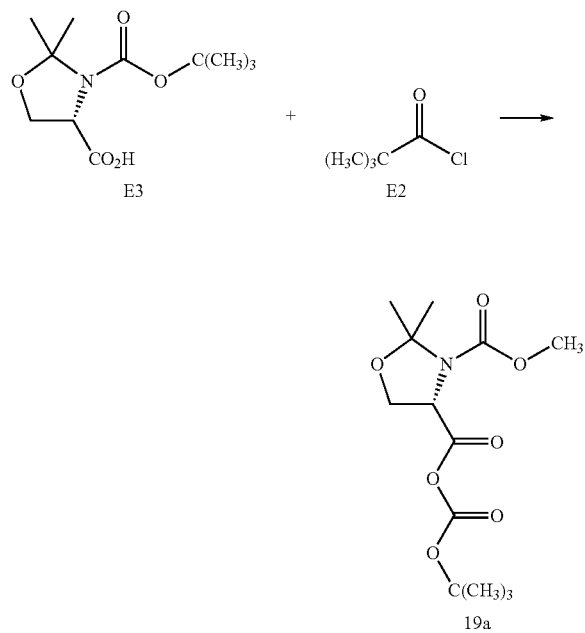

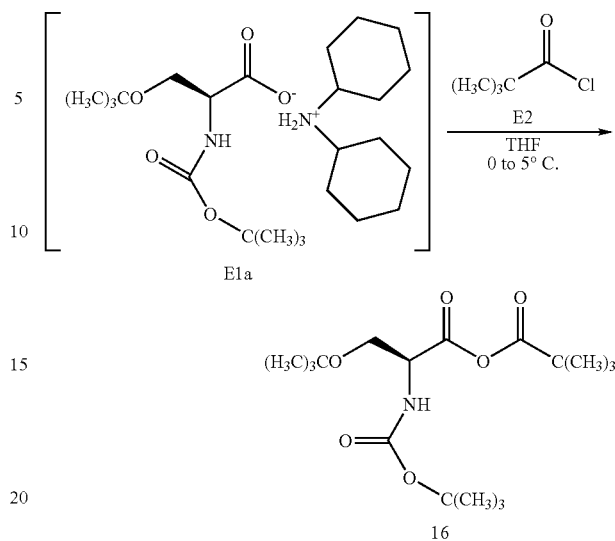

Into a round bottom 3-neck flask fitted with a thermometer and a nitrogen inlet was placed 1.84 g (7.54 mM) of compound E3 and 55 ml of dry THF under nitrogen purge. The reaction mixture was cooled and maintained at a temperature of between 0° C. and +5° C. The cold reaction mixture was charged with 2.95 g of potassium carbonate and agitated from 5 minutes. At the end of the agitation period, 0.93 g (7.7 mM) of compound E2 was added while maintaining the reaction temperature. The reaction mixture was agitated for 1 hour at 0° C. The reaction mixture was mixed with 3.0 g of Celite and the resulting suspension was filtered. The filter cake was washed with two 20 mL aliquots of dry THF. The wash and filtrate were combined and concentrated by distilling off the organics under vacuum to a volume of 3.6 mL. Dry THF was added to the residue and the concentration/redilution cycle was continued until the water content of the batch was determined by Karl Fischer titration to be less than about 0.07 wt %. GC of the dry extract indicates that the reaction yielded 2.87 g, about 87%.

Example 6

Alternative Means to Prepare the Compound of Formula 16

Compound 16 can be prepared in accordance with the procedure described above in Example 1, or alternatively, may be prepared from the salt of the precursor acid as shown below.

Into a 100 gallon glass lined reactor equipped with a thermocouple, $N_2$ inlet and feed tank was charged 26.4 kg of the compound Formula E1a. Tetrahydrofuran (THF) dried to a Karl Fischer titration of less than 0.05% water (202 liters,) was charged at ambient temperature (20° C. to 25° C.) into the reaction vessel to dissolve the charge of compound E1a. When dissolution was complete, the batch was concentrated at 1 atmosphere to a volume of about 140 liters and the temperature was maintained between 20° C. and 30° C. The batch was cooled and maintained at a temperature of between −5° C. and +5° C. Over a period of 30 minutes, 7.3 kg of the compound Formula E2 was charged while maintaining the batch temperature between −5° C. and +5° C. After addition, while maintaining the same temperature, the batch was agitated for 90 minutes. At the end of the agitation period the reactor was charged with 7.8 kg supercel, followed by 54 liters of heptane. The batch was filtered under $N_2$, and the filter cake was washed with 30% v/v THF in heptane. The filtrate and washes were combined and concentrated under vacuum to a batch volume of about 71 liters. The concentrate was warmed to ambient temperature and can be used to prepare the compound of Formula 19 or other amines in accordance with Examples 1 to 5.

The concentrate thus obtained was analyzed by proton NMR ($^1$HNMR in $CDCl_3$) with the following results (chemical shift relative to TMS, multiplicity).

5.33 (1H, d); 4.41 (1H, d); 3.51 (1H, dd); 1.36 (9H, s), 1.22 (9H, s); 1.02 (9H, s)

Alternative Preparation Example 6

To a stirred suspension of 60.0 g (0.136 mol) of E1a in 420 ml of THF was charged under nitrogen 16.6 g (0.138 mol, 1.0 eq.) of compound E2 dropwise at 0° C. over 15 minutes. The resulting mixture was stirred for 2 hours at 0° C. After addition of 18 g of supercel and 120 ml of heptane at 0° C., the mixture was filtered under $N_2$, and the filter cake was washed with 120 ml of 30% v/v THF in heptane. The filtrate and washes were combined and concentrated under vacuum to about 150 ml. The NMR analysis showed it contained 43.3 g (92.5%) of active compound 16. The solution was stored in a refrigerator and could be used to prepare the compound of Formula 19 or other amines in accordance with Examples 1 to 5. $^1$HNMR in $CDCl_3$: 5.33 (1H, d); 4.41 (1H, d); 3.51 (1H, dd); 1.36 (9H, s), 1.22 (9H, s); 1.02 (9H, s)

Example 7

Preparation of Compound [19] by Treatment of Compound [VIII] with Carbonic Acid Methyl Ester Anhydride Compound E6

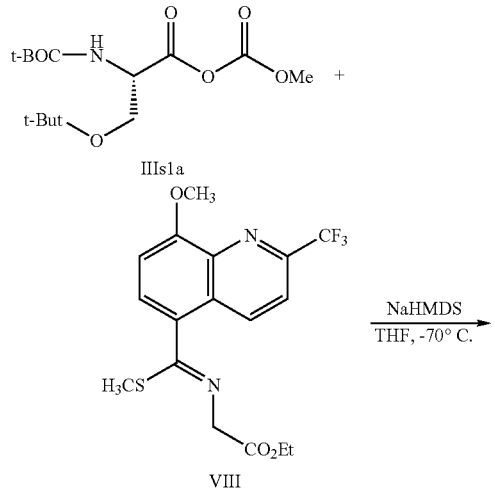

For use in Example 7, compound IIIs1a was prepared in accordance with the dicyclohexylamine procedure described above. Accordingly, to a suspension of 10.0 g of the compound of Formula IIIb1 was added 2.14 g of methylcholorformate in one portion at 0° C. The mixture was stirred for 2 hours at 5° C. followed by addition of 20 ml of heptane and 2 g of Celite. The suspension was filtered and the cake was washed with 30 ml of a solvent comprising 2:1 v/v THF and heptane. The solution was concentrated under vacuum to yield 14.8 g of an oil. The oil was analyzed by $^1$H NMR which indicated that it contained 6.7 g (93%) of the compound of Formula IIIs1a. $^1$H NMR (CDCl$_3$): 5.4 (d, 1H); 4.6 (d, 1H); 3.8 (s, 3H); 3.7 (m, 1H); 3.5 (m, 1H); 1.6 (s, 9H); 1.1 (s, 9H)

Example 8

Preparation of the Compound of Formula IXaa

The compound of Formula IXaa was prepared in accordance with the following 4-step scheme:

Step 1

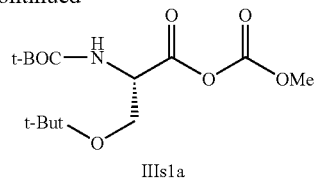

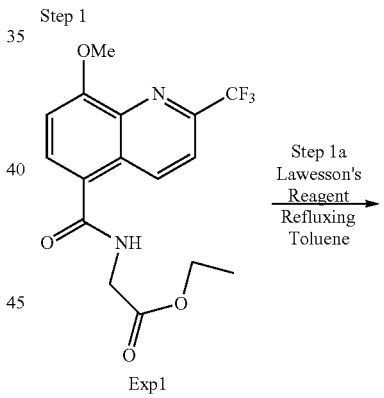

Into a 125 ml 3 neck round bottom flask equipped with a thermometer, N$_2$ inlet and two addition funnels was placed 2.0 g of the compound of Formula VIII in 20 ml of THF. Into the solution was added 1.3 ml of 2M NaHMDS in THF (0.5 eq) at −70° C. The solution was stirred for 5 minutes at temperature and a solution of 1.1 g of the compound of Formula IIIs1a was added in one portion. After 10 minutes of stirring at temperature, the sequential addition of NaHMDS and compound IIIs1a was repeated. The formation of 19 was confirmed by HPLC.

Preparation of Compound IIIs1a

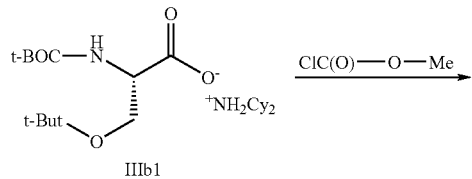

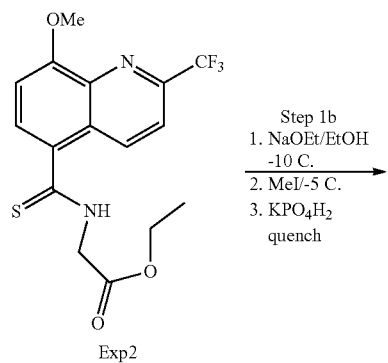

-continued

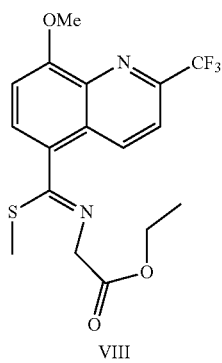

VIII

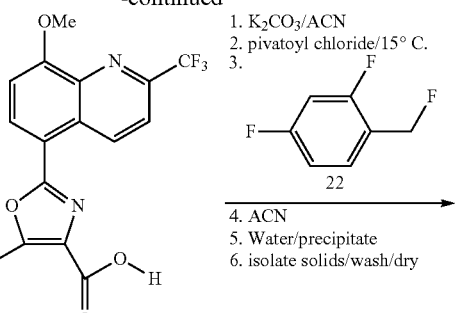

VII

Step 2

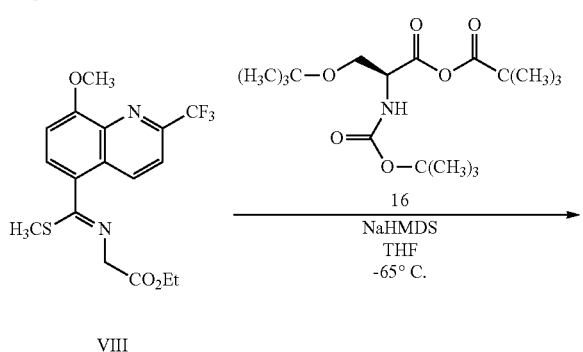

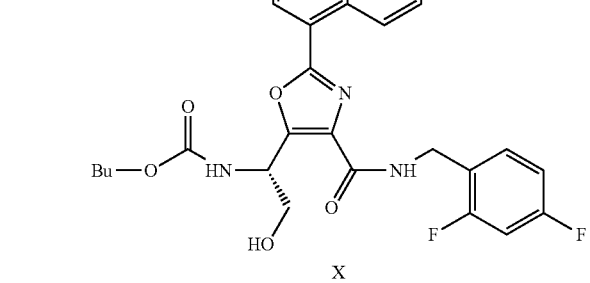

X

Step 4
1. 0° C./Trifluoro Acetic Acid (TFA)/ H₂O
2. 25 degrees C.
3. Concentrate/THF
4. Concentrate/ THF/H₂O
5. 10 C./aq K₂CO₃ water - preciptate
6. Collect solids/Wash

X →

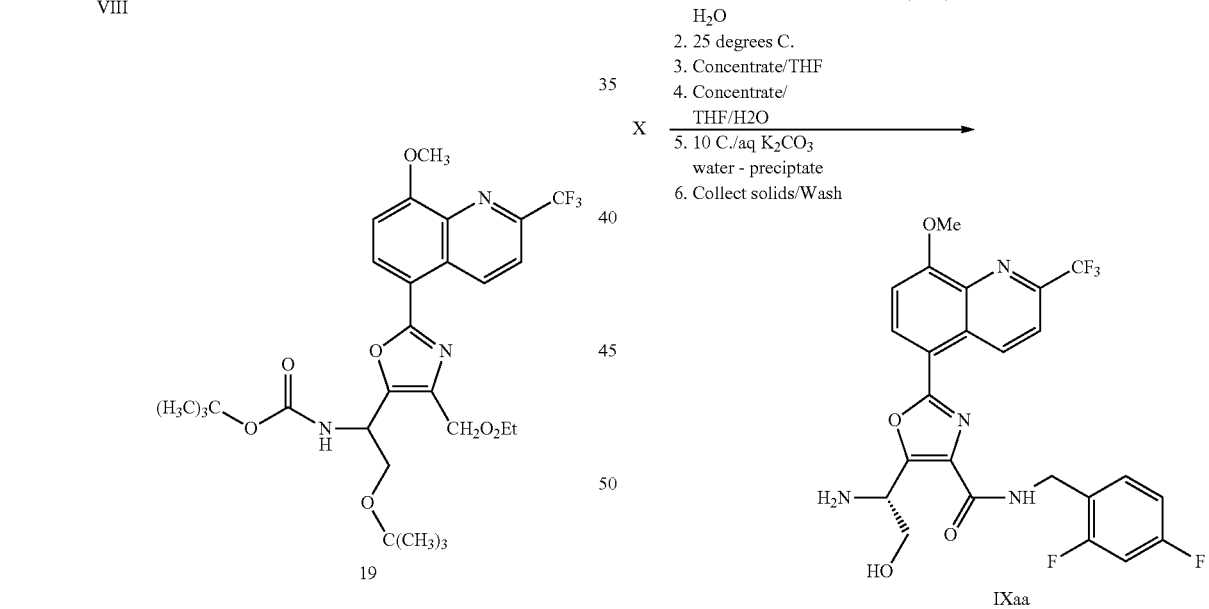

IXaa

Step 3
1. LiOH/THF
2. Water
3. MeOH
4. HCl
5. aq NaCl/ ethyl acetate
6. Isolate/ strip with THF
7. Concentrate

19 →

Step 1a—Preparation of [(8-Methoxy-2-trifluoromethyl-quinoline-5-carbothioyl)-amino]-acetic acid ethyl ester [compound Exp2] from [(8-Methoxy-2-trifluoromethyl-quinoline-5-carbonyl)-amino]-acetic acid ethyl ester [compound Exp1]

Into a 1 L round bottom flask was placed 28.2 g of Lawesson's reagent (0.62 eq), obtained from Aldrich and used as received, and 40 g of compound Exp1 (112.4 mmol, 1 eq) followed by 480 ml of toluene. The mixture was heated to 85-90° C. and agitated for 1 h. At the end of one hour, the reaction mixture was cooled to 60° C. and 12 ml of ethanol was added, the reaction mixture was agitated for 15 minutes thereafter then cooled to 40° C. The reaction mixture was concentrated under vacuum to 20% of the initial volume. When the desired volume was achieved, the reaction mixture was cooled to 0-5° C., held 10 min at this temperature to precipitate the product, Exp2, which was collected by filtration. The solid thus obtained was washed with 1 equivalent volume of toluene and vacuum was applied until the cake was visually dry, yielding a pale yellow solid: $^1$H NMR (400 MHz, CDCl$_3$) δ 8.99 (bs, 1H), 8.70 (d, J=8.7 Hz, 1H), 7.54 (d, J=7.8 Hz, 1H), 7.52 (d, J=7.9 Hz, 1H), 6.75 (d, J=8.6 Hz, 1H); 4.74 (d, J=5.4 Hz, 2H), 4.36 (q, J=7.1 Hz, 2H), 4.01 (s, 3H), 1.39 (t, J=7.1 Hz, 3H); $^{13}$C NMR (100 MHz, CDCl$_3$) δ 198.8, 168.6, 155.8, 138.0, 136.6, 133.5, 127.7, 126.5, 125.8, 120.3, 118.4, 108.2, 62.3, 56.6, 47.8, 14.6; MSES+m/z (relative intensity) 373 (M+H).

Step 1b—Preparation of {[(8-Methoxy-2-trifluoromethyl-quinolin-5-yl)-methylsulfanyl-methylene]-amino}-acetic acid ethyl ester [compound VIII]

The mostly-dried wet cake of Exp2 prepared in Step 1a was placed in a fresh 1L flask, followed by 200 ml of ethanol. The mixture was cooled to −10-0° C. and a solution of NaOEt (21% in EtOH, 46 ml) was added over 15 min via addition funnel. The mixture was held 30 min at this temperature then cooled to between −20° C. to −10° C. Iodomethane (14 ml) was added over about 15 min via addition funnel and the batch was warmed over 2.5 hours to a temperature between −5° C. to 5° C. The reaction was quenched by adding to the flask 200 ml of a 3 wt % aqueous solution of K$_2$HPO$_4$ (6 g total). After addition the reaction mixture was agitated for 15 min, and extracted successively with a mixture comprising 200 ml ethyl acetate and 100 ml of heptane, followed by a mixture comprising 150 ml of ethyl acetate and 40 ml of heptane. The extracts were combined and washed with 200 ml 10% NaCl solution. The extracts were concentrated to 50 ml by vacuum distillation. Isopropanol (80 ml) was added and the batch was concentrated again to 50 ml. Heptane (120 ml) was added and the batch was heated to 50-60° C. to dissolve the precipitated solid, held for 15 min at this temperature, then cooled to 40° C., and then slowly cooled to a temperature between −10 and 0° C. The resulting solids were collected by filtration and the cake washed with 1× of 10% isopropanol in heptane. The collected solids (Exp3) were dried in vacuum oven at 60° C. 6 h and the dry cake was obtained as an off-white solid (34.13 g, 79% overall yield of steps 1a and 1b): $^1$H NMR (400 MHz, CDCl$_3$) E thioimidate isomer, δ 8.31 (d, J=8.7 Hz, 1H), 7.80 (d, J=8.7 Hz, 1H), 7.52 (d, J=8.0 Hz, 1H), 7.15 (d, J=8.2 Hz, 1H), 4.13 (s, 2H), 4.12 (m, 3H), 3.93 (q, J=7.2 Hz, 2H), 2.57 (s, 3H), 1.19 (t, J=7.2 Hz, 3H); Z thioimidate isomer, δ 8.84 (d, J=8.8 Hz, 1H), 7.81 (d, J=8.8 Hz, 1H), 7.63 (d, J=8.1 Hz, 1H), 7.17 (d, J=8.5 Hz, 1H), 4.55 (s, 2H), 4.30 (q, J=7.1 Hz, 2H), 4.10 (m, 3H), 1.94 (s, 3H), 1.35 (t, J=7.1 Hz, 3H); $^{13}$C NMR (100 MHz, CDCl$_3$) Mixture of E/Z isomers δ 172.0, 171.5, 170.7, 169.6, 158.6, 158.4, 149.2, 149.0, 148.9, 148.7, 140.7, 140.7, 137.7, 137.5, 131.2, 130.8, 129.8, 128.6, 128.5, 127.4, 124.6, 121.9, 120.2, 120.2, 110.0, 109.7, 63.1, 62.8, 56.9, 56.8, 17.7, 16.1, 15.9, 15.8; MSES+m/z (relative intensity) 387 (M+H). The solid compound of Formula VIII was found to be stable when stored as a solid powder under inert conditions.

Step 2—Formation of the Oxazole ring (Compound 19) by reaction of the compound of Formula VIII with the anhydride compound of Formula [16]

Under nitrogen, a solution of 17. g (44 mmol) of compound Formula VIII in 220 ml of dry THF was concentrated by distillation under normal pressure to a volume of 90 ml. The solution was cooled to about −70° C. and aliquot of NaHMDS (as a 2M solution in THF equal to 5.25 g, 0.25 eq. of NaHMDS was charged from an additional funnel over about 15 minutes while maintaining the reaction mixture within a temperature range at −60 to −70° C. After the reaction mixture was stirred for 5 minutes at below −65° C., a solution aliquot of the compound Formula 16 in THF (equal to 0.13 eq. of the compound 16) was charged from an additional funnel dropwise over 10 minutes while maintaining the reaction mixture at a temperature between −60° C. and −70° C. The reaction mixture was agitated for 10 minutes while maintaining the temperature between −60° C. and −70° C.

The sequence of the addition of an aliquot of NaHMDS followed by the addition of a solution aliquot of 16 and a period of agitation was repeated seven additional times using the same amount of the reagents in each cycle. The addition of NaHMDS and compound 16 was repeated two more times in a same way as described above except that the amounts of NaHMDS and compound 16 to be charged were reduced to 0.12 eq. and 0.06 eq. respectively. At the end of 10 cycles 95% of VIII had been converted to 19 (by HPLC analysis).

The reaction mixture was transferred over a few minutes to a vessel containing 170 ml of 15% KH$_2$PO$_4$ solution with vigorous agitation. The mixture was stirred for 5 minutes and 100 ml of ethyl acetate was charged. The mixture was agitated for about 15 minutes and the layers permitted to settle. The layers were separated and the aqueous layer was extracted with 85 ml of ethylacetate. The extract was combined with the organic layer and washed with two aliquots of 100 ml 10% NaCl solution. The solution was concentrated at 1 atmosphere to a volume of about 120 ml. Isopropanol (230 ml) was added and the mixture concentrated at 1 atmosphere to a volume of 120 ml. Additional amount of isopropanol (34 ml) and heptane (230 ml) were added to the concentrated mixture slowly with the temperature of the mixture maintained at 65° C. The resulting suspension was slowly cooled to 0° C. over 3 hours. The mixture was agitated for about 30 minutes at this temperature, then the solids were collected by filtration. The filter cake thus prepared was washed with 33% v/v ethylacetate in heptane and dried in a vacuum oven for at least 12 hours at 60° C., to give 20.2 g (79%) of white solids with 99.7% ee. $^1$H NMR (CDCl$_3$): 9.89 (1H, d); 8.56 (1H, d); 7.94 (1H, d); 7.22 (1H, d); 5.91 (1H, s, b); 5.58 (1H, s, b); 4.47 (2H, q); 4.43 (3H, s); 3.75 (2H, t); 1.47 (9H, s); 1.19 (9H, s). Elemental Anal. Calcd. for C$_{28}$H$_{34}$F$_3$N$_3$O$_7$: C, 57.83; H, 5.89; N, 7.23. Found: C, 58.37; H, 6.09; N, 6.95.

Step 3—Preparation of {1-[4-(2,4-Difluoro-benzyl-carbamoyl)-2-(8-methoxy-2-trifluoromethyl-quinolin-5-yl)-oxazol-5-yl]-2-hydroxy-ethyl}-carbamic acid butyl ester Into a round bottom flask was placed 8.0 g of the compound of Formula 19 prepared in Step II (13.8 mmol) and 1.0 g LiOH.H$_2$O in 90 ml of THF was agitated for 15 minutes at room temperature. The mixture was cooled with an ice batch and 32 ml of water was added dropwise from an addition funnel over 20 minutes followed by addition of 25 ml of methanol over 5 minutes. The reaction mixture was then warmed up to room temperature and stirred over night. The mixture was then acidified by addition of 2N HCl solution until pH reached about 3. The mixture was mixed with 15 ml of saturated NaCl solution and 40 ml of ethyl acetate. The organic layer was separated and the aqueous layer was extracted with 25 ml of ethyl acetate. The organic layer was combined with the extracts and the combination was washed with 5% sodium chloride solution. The solution was concentrated by distillation at normal pressure until the batch reached 50 ml volume. THF (100 ml) was charged and the batch was concentrated again to 50 ml. The water content was assayed by Karl Fischer titration and found to be less than 0.05%. To the resulting solution was added 3.0 g extra fine powder $K_2CO_3$ and 30 ml of acetonitrile. The mixture was stirred for 30 minutes at room temperature. The resulting suspension was cooled to 15° C. and 2.1 ml (17.1 mmol) of trimethylacetyl chloride was added. After the mixture was stirred for one hour, a sample was taken for HPLC analysis. When a complete conversion of the acid to mixed anhydride was observed, 2.2 ml (18.5 mmol) of 2,4-difluorobenzylamine was then added at 15° C. followed by 50 ml of acetonitrile. The mixture was then stirred for 45 minutes at room temperature. Water (160 ml) was added slowly over one hour at room temperature, resulting in the precipitation of a crystalline product. The solids were corrected by filtration and the cake was washed 40 ml mixture of acetonitrile and water (1:1 mixture) followed by 25 ml of water. The cake was dried in oven at 60° C., to give 8.7 g (92.9%) white solids. $^1$H NMR (CDCl$_3$): 9.77 (d, 1H), 8.32 (d, 1H), 7.93 (d, 1H), 7.56 (br, 1H), 7.43 (m, 1H), 7.20 (d, 1H), 6.90 (m, 2H), 6.75 (br, 1H), 5.46 (br, 1H), 4.72 (m, 2H), 4.19 (s, 3H), 3.76 (s, 2H) 1.46 (s, 9H), 1.11 (s, 9H). $^{13}$C NMR (CDCl$_3$): ). Anal. Calcd: $C_{33}H_{35}F_5N_4O_6$: C, 58.44; H, 5.20; N, 8.25. Found: C, 58.33; H, 5.15; N, 8.24.

Step 4—Deprotection of Compound X to Form Compound IXaa

Into a 1 liter flask was placed 113.86 g of compound X from Step 3. The flask was cooled to 0-10° C. and trifluoroacetic acid (445 ml, 4×) and water (45 ml) were added. After 15 min, the temperature was allowed to rise to a temperature between 20° C. and 25° C. and the mixture was held at this temperature for 12 h. After this time, the batch was vacuum concentrated to 2× and fresh trifluoroacetic acid (2×) was added and the batch held for an additional 1 h. At this time the batch was vacuum concentrated to 1× and the resulting slurry was dissolved with THF (400 ml) and water (113 ml). The batch was cooled to a temperature between 0° C. and 10° C. A solution of 10% potassium carbonate solution (2.6×) was added and more 10% potassium carbonate solution (375 ml) was added by titration with a pH meter. The solution was titrated until the pH meter indicated a pH between pH 6.5 and pH 7.5. When the desired pH was achieved 2 L of water was added to the batch to further precipitate the product. At the end of the water charge, the batch was cooled to 0-10° C. and the solid collected by filtration. The cake was washed with 10% THF in water (5×) and the wet cake was dried for 12 h at 50° C. in a vacuum oven, after which time the dry cake was obtained (91.743 g, 95% yield) as a white solid: $^1$H NMR (400 MHz, CDCl$_3$) δ 10.19 (d, J=9.0 Hz, 1H), 9.42 (t, J=6.1 Hz, 1H), 8.54 (d, J=8.5 Hz, 1H), 8.54 (bs, 2H), 8.11 (d, J=9.0 Hz, 1H), 7.57 (d, J=8.7 Hz, 1H), 7.47 (q, J=6.9 Hz, 1H), 7.25 (m, J=Hz, 1H), 7.10 (m, J=Hz, 1H), 5.72 (bs, 1H), 5.13 (t, J=5.8 Hz, 1H), 4.57 (m, J=5.2 Hz, 2H), 4.14 (s, 3H), 3.93 (m, 2H); $^{13}$C NMR (100 MHz, CDCl$_3$) δ 163.0, 160.4, 160.3, 151.2, 140.7, 140.1, 134.6, 134.5, 129.0, 125.1, 124.5, 121.0, 115.9, 113.8, 113.6, 111.5, 106.2, 106.0, 105.7, 75.0, 63.1, 58.8, 50.5, 37.7; MSES+m/z (relative intensity) 523 (M+H)

Example 9

Preparation of the Compound of Formula Ixab

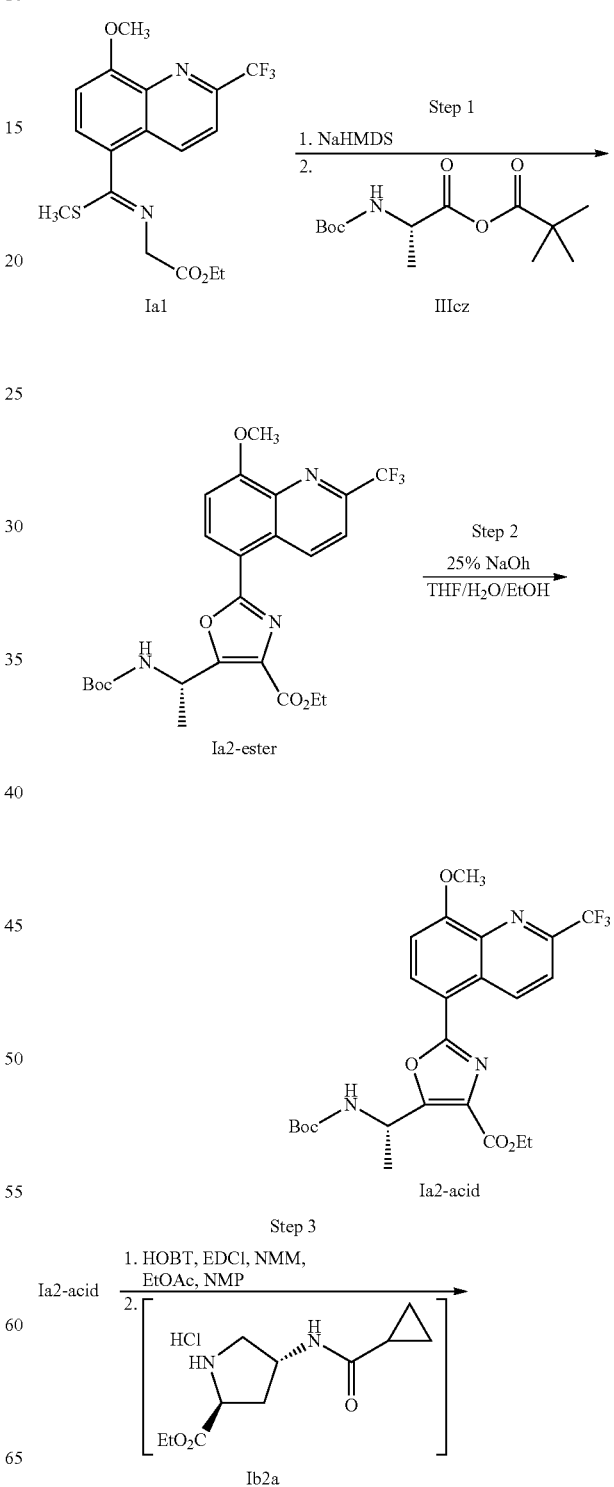

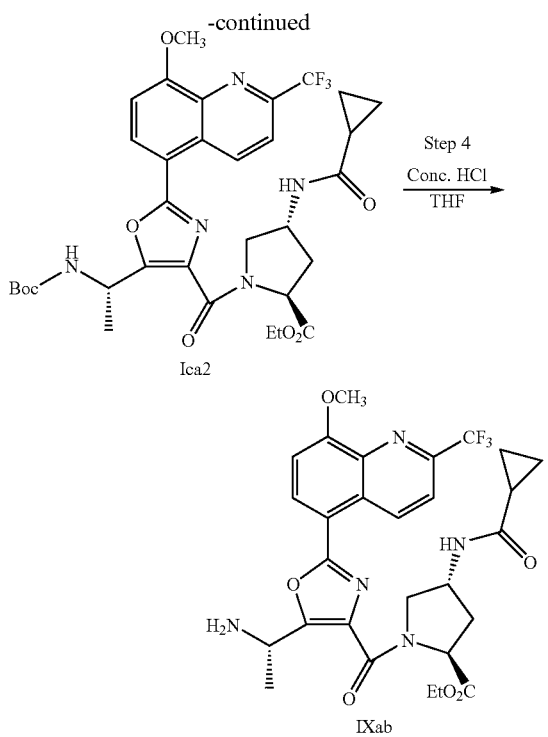

Step 1:

Into a 50 L Hastelloy reactor equipped with a thermocouple, $N_2$ inlet and feed tank was charged 8.8 kg (46.5 moles, 2 eq) of (S)-2-tert-butoxycarbonylamino-propionic acid which was then dissolved in 90 liters dry tetrahydrofuran (THF, KF <0.05%). Into the reactor solution was slowly charged 8.5 kg (46.9 moles, 2 eq) of dicyclohexylamine over 30 minutes while maintaining the temperature of the solution between −5° C. and +5° C. The mixture was agitated for 15 minutes maintaining the temperature between −5° C. and +5° C., then 5.7 kg (47.3 moles, 2 eq) of trimethylacetylchloride was added to the reaction mixture over 30 minutes maintaining the temperature of the reaction mixture between −5° C. and +5° C., followed by 3 hours of agitation while maintaining the reaction mixture temperature. Following the agitation period, 27 liters of heptane, followed by 4.5 kg of celite was added to the reaction mixture, and it was filtered under $N_2$. The filter cake thus obtained was washed with 30% v/v THF in heptane. The filtrate and washes were combined and concentrated under vacuum to a batch volume of 36 liters. To the concentrated reaction mixture was added 27 liters of THF and the temperature of the reaction mixture was adjusted to a temperature between 20° C. and 30° C. The residual water in the reaction mixture was determined by Karl Fischer titration to be less than 0.06 ppm, and the resulting mixed anhydride THF solution was employed in the next step of the synthesis without further purification.

Into a 50 gallon glass lined reactor equipped with a thermocouple, $N_2$ inlet and feed tank was charged 9.0 kg (23.3 moles, 1 eq) of the compound of Formula Ia1, which was then dissolved in 126 liters dry tetrahydrofuran (THF, KF <0.05%). The solution was concentrated at 1 atmosphere to a batch volume of 81 liters. The temperature of the solution was adjusted and maintained at a temperature between −60° C. and −70° C. To the solution was added NaHMDS (2M in THF, 2.70 kg, 5.9 moles, 0.25 eq) over 15 minutes while maintaining the reaction mixture at a temperature between −60° C. and −70° C. The mixture was agitated for 5 minutes while maintaining the temperature between −60° C. and −70° C. The mixed anhydride in THF solution previously prepared (0.83 kg active, 3.2 moles, 0.14 eq) was added to the reaction mixture over a 15 minute period while maintaining the temperature of the reaction mixture between −60° C. and −70° C., then agitated for 10 minutes after the addition was complete. This sequence of adding a charge of (NaHMDS 2M in THF) and then a charge of the mixed anhydride was repeated seven (7) more times for a total of eight (8) sets of charges. After the last charge it was determined that the conversion of the compound of Formula Ia1 exceeded 70%. Aliquots of NaHMDS (2M in THF) followed by mixed anhydride in the same ratio based on the amount of starting material remaining were continued until the conversion of the compound of Formula Ia1 exceeded 94%. The reaction mixture was then transferred over a 15 minute period to an aqueous solution of 13.5 kg $KH_2PO_4$ dissolved in 90 liters $H_2O$ while maintaining the batch temperature below 30° C. Ethyl acetate (59 liters) was added to the mixture and the mixture was agitated for 15 minutes. The layers were separated and the resulting aqueous layer was extracted with 45 liters ethyl acetate and combined with the separated organic layer. The combined organic layers were washed two times with 32 liters 10% aqueous w/v NaCl and concentrate at 1 atmosphere to a batch volume of 45 liters. To the concentrated reaction mixture was added 90 liters methyltertbutylether (MTBE), and the mixture was concentrated at 1 atmosphere to a batch volume of 54 liters. A second aliquot of 45 liters methyltertbutylether was added while maintaining the temperature of the reaction mixture between 55° C. and 65° C., followed by the addition of 108 liters heptane while maintaining the reaction mixture at a temperature between 55° C. and 65° C. The temperature of the reaction mixture was then adjusted and maintained between 45° C. and 55° C. and agitated for 30 minutes. The temperature of the reaction mixture was then adjusted and maintained at a temperature between −5° C. and 5° C. for 1 hour, quiescent, and then agitated while maintaining the temperature for an additional 30 minutes. The resulting precipates were collected by filtration, washed with 33% v/v methyltertbutylether in heptane, and dried in a vacuum oven for 12 hours at 45 to 55° C. affording 8.4 kg (72.2%) of (2) as a solid with an ee of >99.0%.

$^1$H NMR (400 MHz, $CDCl_3$); 9.89 (1H, d); 8.56 (1H, d); 7.94 (1H, d); 7.22 (1H, d); 5.91 (1H, s, b); 5.58 (1H, s, b); 4.47 (2H, q); 4.43 (3H, s); 3.75 (2H, t); 1.47 (9H, s); 1.19 (9H, s).

Step 2:

Into a 500 mL three-neck round bottom flask fitted with a mechanical stirrer, an additional funnel and a thermocouple was charged 20 g (39.3 mmol, 1 eq) of the compound of Formula (Ia2-ester), 60 ml of THF, 20 mL of EtOH, and 100 mL of water. To the mixture was added 8 mL of 25% sodium hydroxide solution. The mixture was agitated while maintaining the temperature of the mixture at 40° C. for 4 hours. HPLC was performed to ascertain that the reaction complete. To the reaction mixture was added 100 ml of water and it was heated to 50° C. While maintaining the reaction mixture at 50° C., 30 ml of 1N HCl solution was added over 30 minutes with stirring, and the reaction mixture was stirred for an additional 30 minutes while maintaining the temperature. After 30 minutes and additional 24 ml 1N HCl solution was added over 30 minutes, followed by 60 ml of water added over 30 minutes while continuing to maintain the reaction mixture at 50° C. throughout these additions. Following the addition of water, the reaction mixture was cooled to room temperature over 1 hour. The resulting precipitate was collected by suction filtration and washed with 40 ml solvent mixture of ethanol and water (1/5, v/v). The solids were dried under vacuum at 60° C. for 12 h affording 16.8 g (90%) of compound (Ia2-acid) as an off white solid.

$^1$H NMR (400 MHz, $d_6$-DMSO): 9.97 (1H, d), 8.42 (1H, d), 8.20 (1H, d), 7.48 (1H, d), 5.40 (1H, m), 4.07 (3H, s), 1.45 (3H, d), 1.30 (9H, s)

Step 3:

Part A

The compound ((2R,4S)-4(cyclopropanecarbonyl-amino)-pyrrolidine-1,2-dicarboxylicacid-1-tert-butyl ester 2-ethyl ester, (60 g, 184 mmol, 1 eq) dissolved in EtOAc (1.2 L) was cooled to 20-35° C. was infused with HCl(gas) until (36 g, 980 mmol, 5.3 eq) had been infused into the solution while maintaining the reaction mixture at a temperature between 20° C. and 35° C. The HCl salt of product began forming during the infusion as the reaction proceeded. At end of HCl infusion, the reaction mixture was heated and maintained at a temperature between 20° C. and 30° C. and agitate for 1 h. After 1 h, the reaction mixture was evaluated by HPLC and determined that complete conversion had been achieved. The reaction mixture was concentrated under vacuum at 35-45° C. to a volume of 600 mL, forming a thick slurry, containing a precipitate of the compound of Formula Ib2a. NMP (280 mL) was then added to the reaction mixture and the mixture was concentrated under vacuum at 35-45° C. to a volume of 560 mL to form a clear solution. This solution was used directly in the coupling step in Part B.

Part B:

Into a 1 L 3-neck RBF was dissolve the compound of Formula (Ica2-acid) (80 g, 166 mmol, 1 eq), HOBT-H$_2$O (28 g, 182 mmol, 1.1 eq) and EDCI.HCl (48 g, 250 mmol, 1.4 eq) in NMP (320 mL) and EtOAc (320 mL). The reaction mixture was stirred while maintaining the temperature at 25° C. for 40 min. The solution of the compound of Formula Ib2a formed in Part A was added to the reaction mixture and stirred for 10 min while maintaining the temperature. N-methyl morpholine (80 mL, 724 mmol, 4.4 eq) was added to the reaction mixture at a rate that maintained the temperature below 35° C. Once the reaction was complete, EtOAc (320) and water (800 mL) were added to the reaction mixture. The resultant mixture was stirred 15 min and the layers were separated. The organic layer was washed with 1M HCl (400 mL), then 10% K$_2$CO$_3$ (400 mL) and water (400 mL), and concentrated to a volume of 160 mL. Acetone (800 mL) was added to the reaction mixture and it was concentrated again to 240 mL at a temperature of between 40° C. and 50° C. under reduced pressure. The reaction mixture was diluted with another 800 mL aliquot of acetone and concentrated again the batch to 240 mL at a temperature of between 40° C. and 50° C. under reduced pressure. While maintaining the reaction mixture temperature at 40° C., 800 mL of heptanes was slowly added to the batch, precipitating the compound of Formula (Ica2). The product solids were collected by filtration and dried under vacuum at 50° C. for 12 h to afford (103 g, 90%) of (4) as an off white solid.

NMR (400 MHz, $d_6$-DMSO): 9.55, 9.03, 8.18, 7.90, 7.77, 7.66, 7.10, 7.04, 6.70, 6.66, 6.10, 5.76, 5.36, 4.91, 4.80, 4.4-3.5, 2.58, 2.30, 1.82, 1.56, 1.47, 1.31, 1.07, 1.00 1.84, 0.74. Note: due to the presence of rotomers, the observed peaks are listed as observed only.

Step 4:

The compound of Formula (Ica2) (20 g, 29 mmol, 1 eq) was charged to a flask and dissolved in THF (60 ml). The solution was cooled to a temperature of between 0° C. and 10° C. Concentrated HCl (20 ml) was added slowly to maintain the temperature between 0° C. and 20° C. At the end of the charge, the solution was warmed and maintained at a temperature of between 20° C. and 30° C., and agitated for 4 h at which time the reaction was determined to be complete by HPLC analysis. The batch was diluted with 2-Me-THF (120 ml) and THF (40 ml) and the reaction was quenched with 20% K$_2$CO$_3$ (110 ml) to achieve a pH of 8-8.5. After adjusting pH, more water (80 ml) was added and the batch was heated to 30° C. to achieve a clean phase split. The batch was settled for 15 min, the lower aqueous layer separated, and the organic layer was washed with water (80 ml). The organic phase was diluted with 2-Me-THF (200 ml) and then concentrated under reflux at atmospheric pressure to 100 ml. The solid product (compound of Formula IXab) was observed at this volume. The batch was then cooled to 0-10° C. and filtered. The wet cake was washed 2 times with 2-Me-THF (40 ml each time). The wet cake was dried for at least 12 h at 60° C. under vacuum affording 13.50 g (79%) of compound of Formula (IXab) as a white solid.

$^1$H NMR (spectrum indicates rotomers, only chemical shift is reported, not integration or peak multiplicity; 400 MHz, $d_6$-DMSO) δ 9.82, 9.62, 8.51, 8.38, 8.07, 7.45, 5.46, 4.69, 4.57, 4.33, 4.15, 4.08, 3.99, 3.83, 2.39, 2.26, 2.16, 1.56, 1.44, 1.22, 0.82, 0.69; MSES+m/z (relative intensity) 590 (M+H).

The above description of the invention is intended to be illustrative and not limiting. Various changes or modifications in the embodiments described herein may occur to those skilled in the art. These changes can be made without departing from the scope or spirit of the invention.

What is claimed is:

1. A process for preparing an oxazole compound of Formula ID

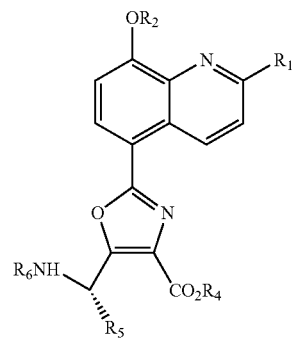

Formula ID wherein

R$_1$ is a haloalkyl;

R$_2$, R$_4$ are alkyl;

R$_5$ is selected from hydrogen, methyl alkyl, hydroxyalkyl, alkoxyalkyl, mercaptoalkyl, —CH$_2$F, —CHF$_2$, —CF$_3$, —C(O)O-alkyl and —C(O)NR$^{43a}$R$^{44a}$, where R$^{43a}$ and R$^{44a}$ are independently selected for each occurrence from the group of H, alkyl, and a nitrogen protecting group; and $R_6$ is selected from acid labile amino protecting groups;
the process comprising:
(a) providing a solution comprising the compound of Formula IDa,

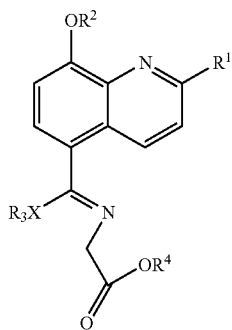

Formula IDa wherein,
$R_1$, $R_2$ and $R_4$ are defined above;
$R_3$ is selected from hydrogen and alkyl; and
X is selected from oxygen and sulfur;
(b) reacting the solution provided in Step "a" with an alkali metal amide base; and
(c) reacting the mixture provided in Step "b" with a compound of Formula IDb,

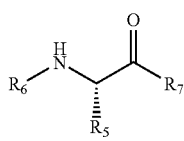

Formula IDb wherein
$R_5$ and $R_6$ are as defined above; and
$R_7$ represents an activated acid moiety.

2. The process of claim 1 wherein $R_7$ is an alkylcarbonyloxy moiety.

3. The process of claim 1 wherein $R_7$ is a halogen.

4. The process of claim 2 wherein, Step "b" is carried out by adding an aliquot of an Lewis base in an amount which is less than required to react with all of the compound Formula IDa in a reaction mixture, and Step "c" is carried out by adding an amount of the anhydride compound of Formula IDb equivalent to the amount of the compound of Formula IDa added, then repeating the addition of Lewis base followed by anhydride until substantially all of the compound of Formula IDa has been reacted.

5. A process for preparing the compound of Formula IXab,

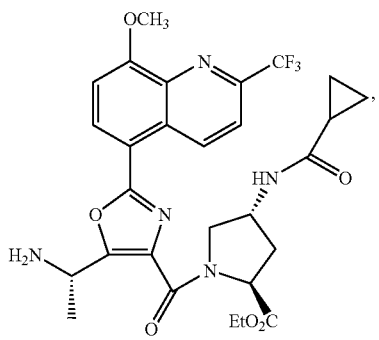

Formula IXab the process comprising:
(a) providing the anhydride of Formula Ib1a,

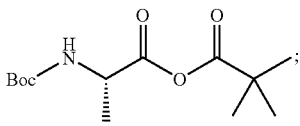

Formula Ib1a (b) reacting the compound of the Formula Ia1,

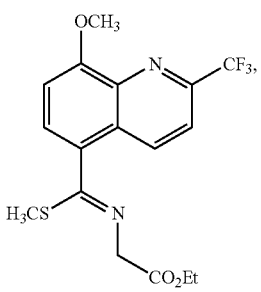

Formula Ia1 with a Lewis base to form an intermediate and reacting that intermediate with the anhydride provided in Step "a" to form the compound of Formula Ia2-ester,

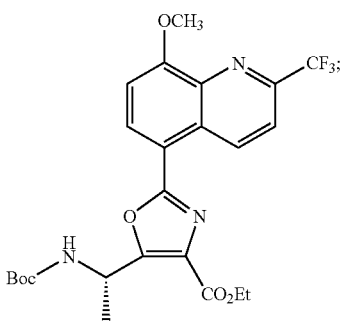

Formula Ia2-ester (c) converting the compound of Formula Ia2-ester to the acid of Formula Ia2-acid by treatment with aqueous base;

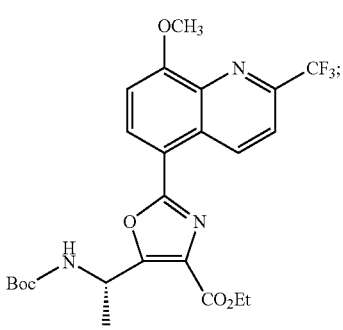

Formula Ia2-acid (d) reacting the compound of Formula Ia2-acid with the amino salt compound of the Formula Ib2a,

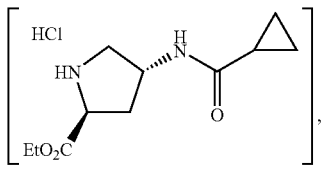

Formula Ib2a to form the compound of Formula Ic2a,

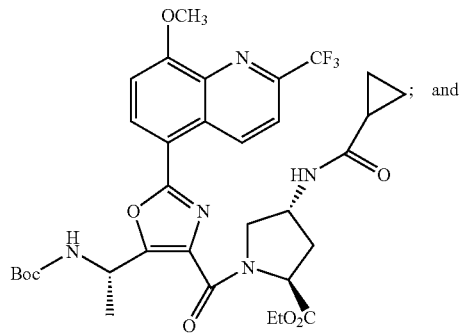

Formula Ic2a (e) deprotecting the compound of Formula Ic2a formed in Step "d" to form the compound of Formula IXab.

6. The process of claim 5, wherein the Lewis base is sodium bis(trimethylsilyl)amide (NaHMDS).

7. The process of claim 5 wherein, the aqueous base used in step "c" is 25% sodium hydroxide and hydrolysis is carried out in the presence of ethanol.

8. The process of claim 5 wherein the anhydride of Formula Ib1a in step "a" is prepared by a process comprising reacting the compound of Formula Ib1b (N-Boc-L-alanine),

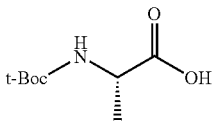

Formula Ib1b with trimethylacetylchloride in the presence of dicyclohexylamine.

9. The process of claim 5 wherein the compound of Formula Ib2a used in Step "d", amidation reaction step, is provided by treating a solution containing a proline derivative compound of the Formula IB2a2,

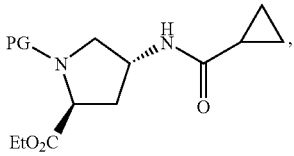

Formula IB2a2 wherein PG is an acid labile protecting group, with an acid.

10. The process of claim 6 wherein, the aqueous base used in step "c" is 25% sodium hydroxide and hydrolysis is carried out in the presence of ethanol.

11. The process of claim 6 wherein, Step "b" is carried out by placing the compound of Formula Ia1 in a reaction mixture, adding an aliquot of a Lewis base in an amount which is less than required to react with all of the compound of Formula Ia1 present, Step "c" is carried out by adding an amount of the anhydride compound of Formula Ib1 equivalent to the amount of Lewis base added in Step "b", and repeating the addition of Lewis base followed by anhydride until substantially all of the compound of Formula Ia1 has been reacted.

12. The process of claim 11 wherein the Lewis base is added in from about 5 to about 10 equal aliquots.

* * * * *